(12) United States Patent
Baran et al.

(10) Patent No.: US 9,409,931 B1
(45) Date of Patent: Aug. 9, 2016

(54) 3-O-ACYL-INGENOL ANALOGUES

(71) Applicant: LEO LABORATORIES LIMITED, Dublin (IE)

(72) Inventors: Phillippe S. Baran, La Jolla, CA (US); Jakob Felding, Ballerup (DK); Yehua Jin, La Jolla, CA (US); Chien-Hung Yeh, La Jolla, CA (US)

(73) Assignee: LEO LABORATORIES LIMITED, Dublin (IE)

( * ) Notice: Subject to any disclaimer, the term of this patent is extended or adjusted under 35 U.S.C. 154(b) by 0 days.

(21) Appl. No.: 14/739,731

(22) Filed: Jun. 15, 2015

(51) Int. Cl.
| | | |
|---|---|---|
| C07C 69/75 | (2006.01) | |
| A61K 31/215 | (2006.01) | |
| A61K 31/695 | (2006.01) | |
| C07F 7/08 | (2006.01) | |

(52) U.S. Cl.
CPC .............. *C07F 7/0834* (2013.01); *A61K 31/215* (2013.01); *A61K 31/695* (2013.01); *C07C 69/75* (2013.01)

(58) Field of Classification Search
None
See application file for complete search history.

(56) References Cited

FOREIGN PATENT DOCUMENTS

WO    WO 2012/083954 A1    6/2012

OTHER PUBLICATIONS

Liang et al. Bioorganic & Medicinal Chemistry Letters, 2013, 23, 5624-5629.*
Challacombe et al., "Neutrophils Are a Key Component of the Antitumor Efficacy of Topical Chemotherapy with Ingenol-3-Angelate", The Journal of Immunology, vol. 177, 2006, pp. 8123-8132.
Cozzi et al., "Induction of Senescence in Diterpene Ester-Treated Melanoma Cells via Protein Kinase C-Dependent Hyperactivation of the Mitogen-Activated Protein Kinase Pathway", Cancer Research, vol. 66, No. 20, Oct. 15, 2006, pp. 10083-10091.
Ersvaer et al., "The Protein Kinase C Agonist PEP005 (Ingenol 3-Angelate) in the Treatment of Human Cancer: A Balance between Efficacy and Toxicity", Toxins, vol. 2, Jan. 22, 2010, pp. 174-194.
Evans et al., "A New Ingenol Type Diterpene From the Irritant Fractions of Euphorbia Myrsinites and Euphorbia Biglandulosa" Phytochemistry, vol. 13, 1974, pp. 2324-2325.
Hampson et al., "PEP005, a selective small-molecule activator of protein kinase C, has potent antileukemic activity mediated via the delta isoform of PKC", Blood, vol. 106, No. 4, Aug. 15, 2005 (Prepublished online Apr. 21, 2005), pp. 1362-1368.
Hampson et al., "The anti-tumor agent, ingenol-3-angelate (PEP005), promotes the recruitment of cytotoxic neutrophils by activation of vascular endothelial cells in a PKC-σ dependent manner", Cancer Immunol Immunother, vol. 57, 2008 (Published online Feb. 12, 2008), pp. 1241-1251.
Jørgensen et al., "14-Step Synthesis of (+)-Ingenol from (+)-3-Carene", Sciencexpress, Aug. 1, 2013, pp. 1-7.
Le et al., "Immunostimulatory cancer chemotherapy using local ingenol-3-angelate and synergy with immunotherapies", Vaccine, vol. 27, 2009 (Available online Apr. 3, 2009), pp. 3053-3062.
Marco et al., "Ingenane and Lathyrane Diterpenes from the Latex of Euphorbia Canariensis", Phytochemistry, vol. 45, No. 3, 1997, pp. 563-570.
Ogbourne et al., "Antitumor Activity of 3-Ingenyl Angelate: Plasma Membrane and Mitochondrial Disruption and Necrotic Cell Death", Cancer Research, vol. 64, Apr. 15, 2004, pp. 2833-2839.
Paquette et al., "Regioselective Routes to Nucleophilic Optically Active 2- and 3-Carene Systems", J. Org. Chem., vol. 55, No. 5, 1990, pp. 1589-1598.
Rosen et al., "Dual mechanism of action of ingenol mebutate gel for topical treatment of actinic keratoses: Rapid lesion necrosis followed by lesion-specific immune response", J. Am Acad. Dermatol., vol. 66, No. 3, Mar. 2012, pp. 486-493.
Upadhyay et al., "Presence of Ingenol and a New Diterpene 4-Deoxy Ingenol in the Latex of Euphorbia Megalantha (BOISS)", Current Science, vol. 56, No. 20, Oct. 20, 1987, pp. 1058-1059.

* cited by examiner

*Primary Examiner* — Yevegeny Valenrod
(74) *Attorney, Agent, or Firm* — Birch, Stewart, Kolasch & Birch, LLP

(57) ABSTRACT

The present invention relates to a compound according to formula I

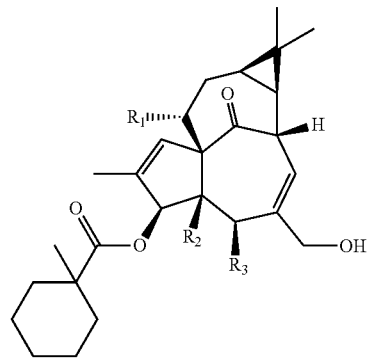

wherein $R_1$ represents hydrogen, $R_2$ represents hydroxyl and $R_3$ represents hydroxyl;
or $R_1$ represents methyl, $R_2$ represents hydroxyl and $R_3$ represents hydrogen;
or $R_1$ represents methyl, $R_2$ represents hydrogen and $R_3$ represents hydroxyl;
or $R_1$ represents methyl, $R_2$ represents hydrogen and $R_3$ represents hydrogen;
or pharmaceutically acceptable hydrates or solvates thereof.
The invention further relates to said compounds for use as a medicament, to pharmaceutical compositions comprising said compounds, to methods of treating diseases with said compounds and to intermediates for the preparation of said compounds.

13 Claims, No Drawings

3-O-ACYL-INGENOL ANALOGUES

FIELD OF THE INVENTION

This invention relates to novel analogues of 3-O-acyl-ingenol and their use as a medicament. The invention also provides pharmaceutical compositions comprising said compounds, methods of treating diseases with said compounds and intermediates for the preparation of said compounds.

BACKGROUND OF THE INVENTION

Ingenol-3-angelate (PEP005, ingenol mebutate, Picato®) is a diterpene-ester of the ingenol family which is isolated from various *Euphorbia* species, particularly from *Euphorbia peplus*. Picato® is marketed for treatment of actinic keratosis and is presently subject for clinical development for the treatment of non-melanoma skin cancer.

Ingenol-3-angelate is believed to have a dual mode of action: 1) Induction of cell death by direct cytoxicity or induction of apoptosis and 2) an immunostimulatory effect dominated by neutrophil recruitment and activation (Rosen, R. H., et al., *J Am Acad Dermatol* (2012); 66:486-93; Ersvaer, E., et al., *Toxins*, (2010), 2, 174-194). Nanomolar concentrations of the agent cause activation and modulation of protein kinase C (PKC) classical and novel isoforms, with particular importance of PKCdelta. Through activation of PKCdelta the agent induces apoptosis in susceptible cells (Hampson, P., et al., *Blood*, (2005), 106, 1362-1368; Cozzi, S. J., et al., *Cancer Res*, (2006), 66, 10083-10091). Rapid cytotoxicity on cancer cells is observed at high micromolar concentrations (Ogbourne, S. M., et al., *Cancer Res* (2004), 64, 2833-2839). Through activation of various PKC isoforms the agent also induces pro-inflammatory effects, including release of pro-inflammatory mediators (Challacombe, J. M., et al., *J Immunol* (2006), 177, 8123-8132); activation of vascular endothelium (Hampson, P., et al., *Cancer Immunol Immunother*, (2008), 57, 1241-1251); chemoattraction of neutrophils through induction of interleukin 8 in keratinocytes and development of specific anti-cancer immune responses by CD8+ cells through adjuvant properties in animal models (Le, T. T., et al., *Vaccine*, (2009), 27, 3053-3062).

Compounds exerting dual mode of action by induction of cell death by direct cytoxicity or induction of apoptosis, and by an immunostimulatory effect involving neutrophil recruitment and activation, may be useful for treatment of conditions associated with hyperplasia or neoplasia. Compounds inducing cell death by primary and/or secondary necrosis and compounds exhibiting a pro-apoptotic effect may reduce unwanted cell growth and remove unwanted cells, and furthermore, stimulation of the innate immune response and adjuvant effects may augment the biological response against aberrant or transformed cells.

WO2012083954 disclose carbocyclic 3-O-acyl ingenol derivatives.

Marco, J. A. et. al.; *Phytochemistry*, (1997) 45, 563-70; and Evans, F. J.; Phytochemical Reports, (1974), 13, 2324-25, disclose 5-deoxy-ingenol derivatives.

Upadhyay, R. R. et. al; Curr. Science (1987), 56, 1058-1059 disclose 4-deoxy-ingenol derivatives.

There is a need to find new ingenol derivatives which induce cell death by cytotoxicity or apoptosis and/or induce an immunostimulatory effect.

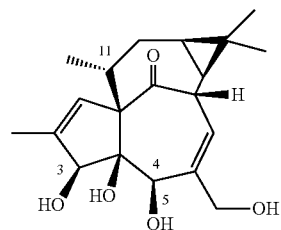

Ingenol

The present invention discloses a method of preparing 3-O-acyl ingenol analogues wherein the substituents at C-4, C-5 and C-11 of the ingenol skeleton have been modified.

Synthetic routes leading to such analogues have not previously been disclosed.

It has surprisingly been found that carbocyclic 3-O-acyl ingenol analogues wherein the ingenol skeleton has been modified at the C-4, C-5 and C-11 positions exhibit properties which make them useful for treatment of conditions associated with the use of ingenol-3-angelate or useful for conditions which are affected by induction of cell death by cytoxicity or induction of apoptosis and/or by an immunostimulatory effect.

Compounds of the present invention stimulate neutrophil oxidative burst, which is part of the innate immune response.

Compounds of the present invention stimulate keratinocyte IL-8 release, thus inducing an immunostimulatory effect.

Compounds of the present invention are PKCδ activators.

Compounds of the present invention are PKCβ activators.

Some compounds of the present invention may induce rapid necrosis.

SUMMARY OF THE INVENTION

In an embodiment the invention provides a compound of the general formula I

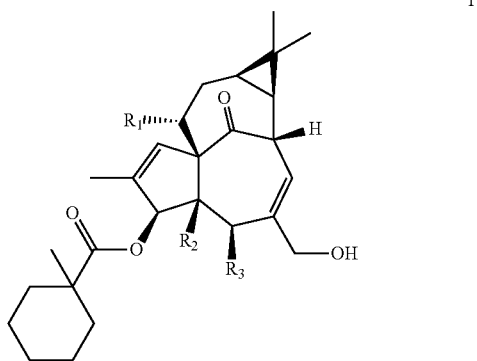

I wherein
$R_1$ represents hydrogen, $R_2$ represents hydroxyl and $R_3$ represents hydroxyl;
or
$R_1$ represents methyl, $R_2$ represents hydroxyl and $R_3$ represents hydrogen;
or
$R_1$ represents methyl, $R_2$ represents hydrogen and $R_3$ represents hydroxyl;
or
$R_1$ represents methyl, $R_2$ represents hydrogen and $R_3$ represents hydrogen;
or hydrates or solvates thereof.

In another aspect, the invention relates to compounds according to formula I for use as a medicament.

In yet another aspect, the invention relates to compounds according to formula I for use in treatment of physiological disorders or diseases associated with hyperplasia or neoplasia.

In yet another aspect, the invention relates to a pharmaceutical composition comprising a compound according to formula I together with a pharmaceutically acceptable vehicle or excipient or pharmaceutically acceptable carrier(s), optionally together with one or more other therapeutically active compound(s).

DETAILED DESCRIPTION OF THE INVENTION

Definitions

The term "alkyl" is intended to indicate a radical obtained when one hydrogen atom is removed from a branched or linear hydrocarbon. Said alkyl comprises 1-6, such as 1-4, such as 2-3, such as 1-2 carbon, such as 1 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl and n-hexyl.

In some instances, the number of carbon atoms in a hydrocarbon radical (e.g. alkyl) is indicated by the prefix "$(C_a-C_b)$", wherein a is the minimum number and b is the maximum number of carbons in the hydrocarbon radical. Thus, for example $(C_1-C_6)$alkyl is intended to indicate an alkyl radical comprising from 1 to 6 carbon atoms, The term "hydrocarbon radical" is intended to indicate a radical containing only hydrogen and carbon atoms. Said hydrocarbon comprises 1-6 carbon atoms, and preferably comprises e.g. 1-4, e.g. 1-2 carbon, e.g. 1 carbon atom. The term includes alkyl as indicated herein.

The term "cycloalkyl" is intended to indicate a saturated cycloalkane hydrocarbon radical, comprising 3-6 carbon atoms, such as 3-5 carbon atoms or such as 6 carbon atoms, e.g. cyclopropyl, cyclobutyl, cyclopentyl and cyclohexyl.

The term "hydroxyl" is intended to indicate an —OH group.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

The term "cancer" in the context of the present invention is intended to cover skin cancer such as non-melanoma skin cancer, malignant melanoma, Merkel cell carcinoma, squamous cell carcinoma, basal cell carcinoma. Basal cell carcinomas covers as well superficial basal cell carcinomas as nodular basal cell carcinoma. Squamous cell carcinoma covers squamous cell carcinoma in situ (Bowen's disease), invasive squamous cell carcinoma, cutaneous squamous cell carcinoma, mucosal squamous cell carcinoma, head and neck squamous cell carcinoma. Other cancer types includes haematological cancer such as myeloid cancers in particular such as acute myeloid leukemia and chronic myeloid leukemia; Cancer of the prostate and bladder including benign prostatic hyperplasia, prostatis intraepithelial carcinoma, carcinoma of the bladder, adenocarcinoma of the prostate and renal cell carcinoma. Other cancer include AIDS related cancer, acoustic neoma, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (bcc), bladder cancer, bone cancers, bowel cancer, brain stem glioma, brain and CNS cancers, breast cancer, CNS cancers, carcinoid cancers, cervical cancer, childhood brain cancers, childhood cancer, childhood soft tissue sarcoma, chondrosarcoma, choriocarcinoma, colorectal cancers, cutaneous T-Cell lymphoma, dermatof[iota]brosarcoma-protuberans, desmoplastic small round cell cancer, ductal carcinoma, endocrine cancers, endometrial cancer, ependymoma, esophageal cancer, Ewing's sarcoma, extra hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal carcinoid cancer, genitourinary cancers, germ cell cancers, gestational trophoblastic disease, glioma, gynecological cancers, hematological malignancies including acute myeloid leukemia, head and neck cancer, hepatocellular cancer, hereditary breast cancer, histiocytosis, Hodgkin's disease, human papillomavirus, hydatidiform mole, hypercalcemia, hypopharynx cancer, intra-ocular melanoma, isle T-cell cancer, Kaposi's sarcoma, kidney cancer, Langerhan's cell histiocytosis, laryngeal cancer, leiomyosarcoma, li-fraumeni syndrome, lip cancer, liposarcoma, liver cancer, lung cancer, lymphedema, lymphoma, Hodgkin's lymphoma, non-Hodgkin's lymphoma, male breast cancer, malignant rhabdoid cancer of kidney, medulloblastoma, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-small cell lung cancer (nscic), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral neuroectodermal cancers, pituitary cancer, polycythemia vera, prostate cancer, rare cancers and associated disorders, retinoblastoma, rhabdomyosarcoma, rothmund Thomson syndrome, salivary gland cancer, sarcoma, schwannoma, sezary syndrome, small cell lung cancer (scic), small intestine cancer, soft tissue sarcoma, spinal cord cancers, stomach cancer, synovial sarcoma, testicular cancer, thymus cancer, thyroid cancer, transitional cell cancer (bladder), transitional cell cancer (renal-pelvis–/– ureter), trophoblastic cancer, urethral cancer, urinary system cancer, uroplakins, uterine sarcoma, uterus cancer, vaginal Cancer, vulva cancer, Waldenstrom's macroglobulinemia and Wilms' Cancer. The solid cancer which is treated using the methods of the present invention may be a primary lesion or may be the result of metastasis of a primary cancer. Furthermore, if the solid cancer is a metastasis of a primary cancer, the primary cancer may be either a primary solid cancer as described above or may be a dispersed primary cancer.

Embodiments of the Invention

An embodiment of the invention is the compound of the formula

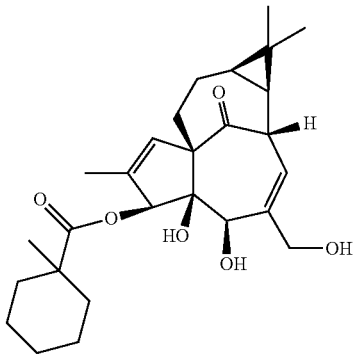 [SMILES: CC1=C[C@@]23CC[C@@H]4[C@H]([C@H](C=C(CO)[C@@H](O)[C@]2(O)[C@H]1OC(=O)C1(C)CCCCC1)C3=O)C4(C)C]

An embodiment of the invention is the compound according formula I, wherein R$_1$ represents hydrogen, R$_2$ represents hydroxyl and R$_3$ represents hydroxyl.

An embodiment of the invention is 11-desmethyl-ingenol 3-(1-methyl-cyclohexanecarboxylate).

An embodiment of the invention is the compound of the formula

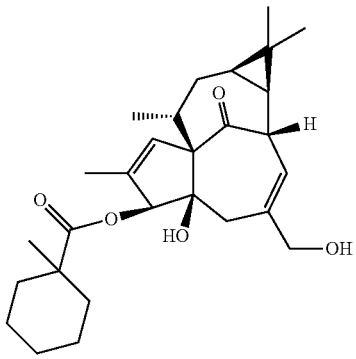 [SMILES: CC1=C[C@]23C(=O)[C@@H](C=C(CO)C[C@]2(O)[C@H]1OC(=O)C1(C)CCCCC1)[C@H]1[C@@H](C[C@H]3C)C1(C)C]

An embodiment of the invention is the compound according formula I, wherein R$_1$ represents methyl, R$_2$ represents hydroxyl and R$_3$ represents hydrogen.

An embodiment of the invention is 5-deoxyingenol 3-(1-methyl-cyclohexanecarboxylate).

An embodiment of the invention is the compound of the formula

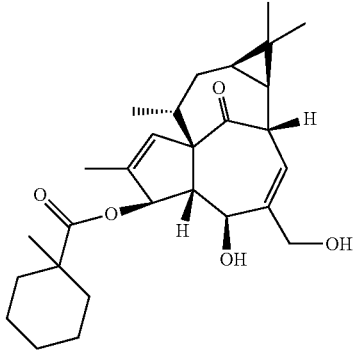 [SMILES: CC1=C[C@]23C(=O)[C@@H](C=C(CO)[C@@H](O)[C@@H]2[C@H]1OC(=O)C1(C)CCCCC1)[C@H]1[C@@H](C[C@H]3C)C1(C)C]

An embodiment of the invention is the compound according formula I, wherein R$_1$ represents methyl, R$_2$ represents hydrogen and R$_3$ represents hydroxyl.

An embodiment of the invention is 4-deoxyingenol 3-(1-methyl-cyclohexanecarboxylate).

An embodiment of the invention is the compound of the formula

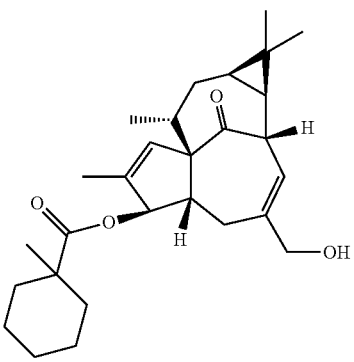 [SMILES: CC1=C[C@]23C(=O)[C@@H](C=C(CO)C[C@@H]2[C@H]1OC(=O)C1(C)CCCCC1)[C@H]1[C@@H](C[C@H]3C)C1(C)C]

An embodiment of the invention is the compound according formula I, wherein R$_1$ represents methyl, R$_2$ represents hydrogen and R$_3$ represents hydrogen.

An embodiment of the invention is 4,5-dideoxyingenol 3-(1-methyl-cyclohexanecarboxylate).

In an embodiment the invention relates to intermediates of the formulas:

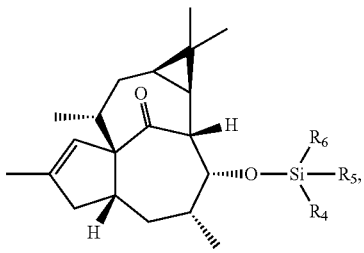

11a

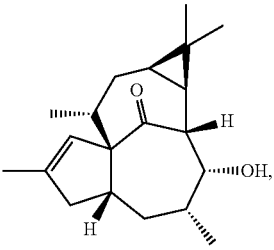

16

-continued
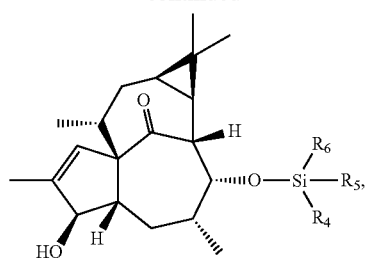
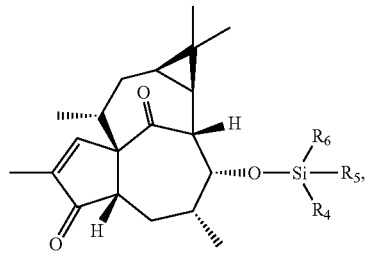
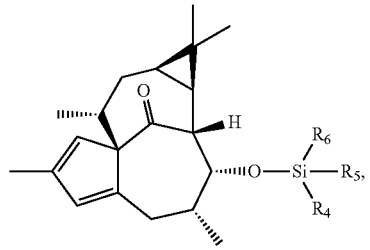
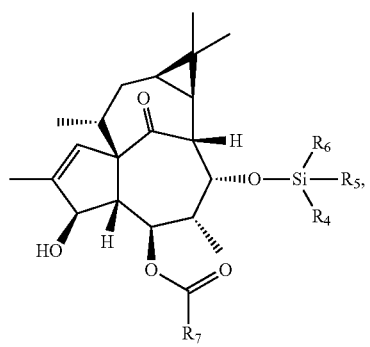
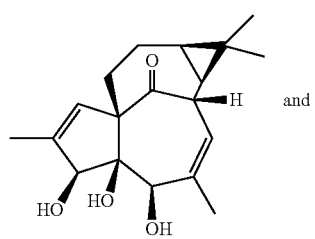
and
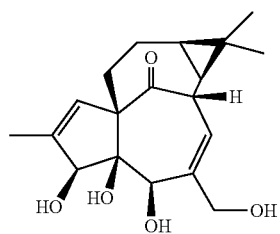
wherein $R_4$, $R_5$, $R_6$ and $R_7$ each independently are selected from the group consisting of $(C_1-C_6)$alkyl.
In yet an embodiment the invention relates to intermediates of the formulas:
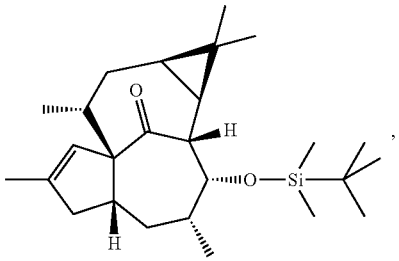
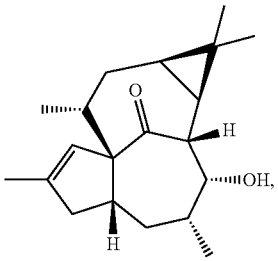
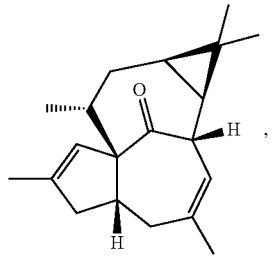
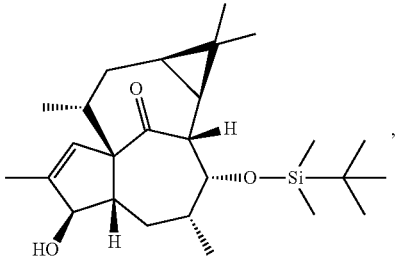
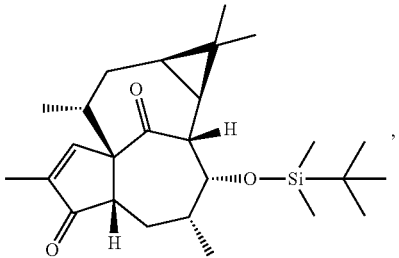
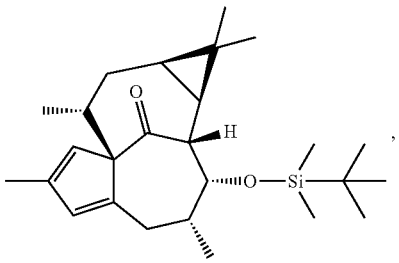

-continued

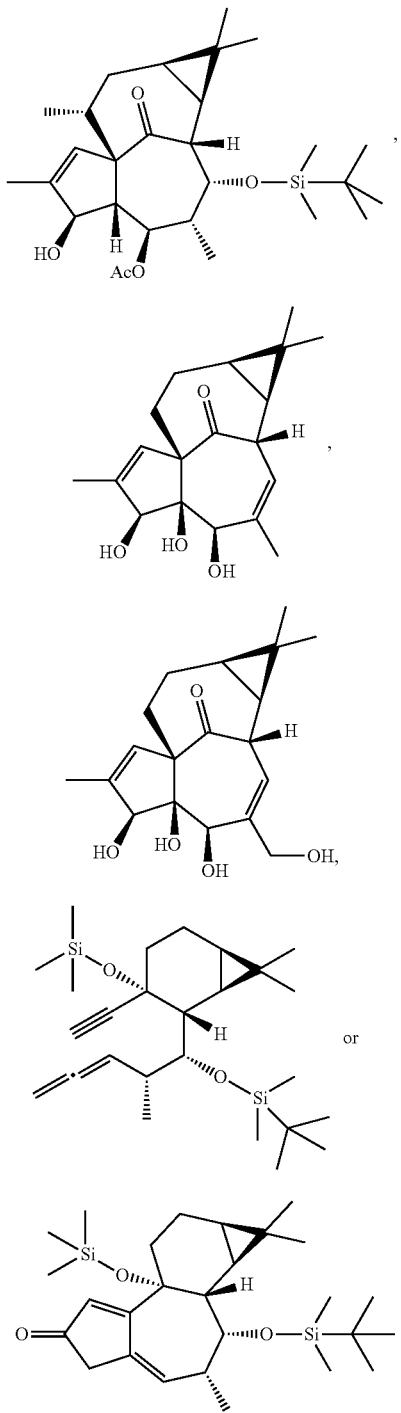

In an embodiment of the invention "cancer" is skin cancer.

In embodiments of the invention, skin cancer is non-melanoma skin cancer, malignant melanoma, Merkel cell carcinoma, squamous cell carcinoma, squamous cell carcinoma, basal cell carcinoma such as superficial basal cell carcinomas or nodular basal cell carcinoma.

The phrase "physiological disorders or diseases associated with hyperplasia or neoplasia" in the context of the present invention is intended to cover disorders or diseases such as cutaneous warts, including common warts (*Verruca vulgaris*), plantar warts (*Verruca plantaris*) and flat warts (*verruca plana*); Genital warts (*condyloma acuminatum*), Pyogenic granuloma, Haemangioma, Scleroderma; Cancers and precancerous lesions such as Actinic keratosis, Squamous cell carcinoma including squamous cell carcinoma in situ (Bowen's disease), invasive squamous cell carcinoma, cutaneous squamous cell carcinoma, mucosal squamous cell carcinoma, head and neck squamous cell carcinoma; Basal cell carcinoma including Superficial basal cell carcinoma and Nodular basal cell carcinoma; Bladder cancer, Lentigo maligna, Cervical dysplasia, Vulva dysplasia and anal dysplasia, Primary melanoma in situ, Head and neck cancer, Cutaneous metastases of any cancer, Kaposi's sarcoma, Keratoacanthoma, Merkel cell tumor, Prostate cancer, Mycosis fungoides, Intraepithelial neoplasias including anal, cervical, ductal, oral, perianal, prostatic, penile, vaginal and vulvar intraepithelial neoplasia.

The term "cosmetic indications" in the context of the present invention is intended to cover indications such as: Photodamaged skin, Seborrheic keratosis, Scars, Keloids, Melasma, Poikiloderma of Civatte, Tattoo removal, Naevi and Skin tags.

The term "photodamaged skin" in the context of the present invention is intended to cover fine lines, wrinkles and UV-ageing. UV ageing is often manifested by an increase in the epidermal thickness or epidermal atrophy and most notably by solar elastosis, the accumulation of elastin containing material just below the dermal-epidermal junction. Collagen and elastic fibres become fragmented and disorganised. At a cosmetic level this can be observed as a reddening and/or thickening of the skin resulting a lethery appearance, skin fragility and irregular pigmentation, loss of tone and elasticity, as well as wrinkling, dryness, sunspots and deep furrow formation.

The term "viral infections" in the context of the present invention is intended to cover HPV infections leading to formation of warts on the body, such as the skin, genitals and mouth. HPV refers to human papilloma virus. Other viruses are selected from adeno-, papova-, herpes- (such as simplex) varicella-zoster, Epstein-Barr-, CMV-, Pox- (such as small pox-) vaccinia-, hepatitis A-, hepatitis B-, hepatitis C-, Rhino-, polio-, rubella-, arbo-, rabies-, influenza-A and B, measles-, mumps-viruses, and HIV, HTLV I and II. In an embodiment of the invention HPV infection refers to common warts or genital warts.

The term "bacterial infections" in the context of the present invention is intended to cover prokaryotic and eukaryotic bacterial infections and Gram positive and Gram negative and Gram variable bacteria and intracellular bacteria. Examples of bacteries includes *Treponema, Borrelia, Neisseria, Legionella, Bordetella, Escherichia, Salmonella, Shigella, Klebsiella, Yersinia, Vibrio, Hemophilus, Rickettsia, Chlamydia, Mycoplasma, Staphylococcus, Streptococcus, Bacillus, Clostridium, Corynebacterium, Proprionibacterium, Mycobacterium, Ureaplasma* and *Listeria*. In particular the species: *Treponema pallidum, Borrelia Burgdorferi, Neisseria gonorrhoea, Legionella pneumophila, Bordetella pertussis, Escherichia coli, Salmonella typhi, salmonella typhimurium, Shigella dysenteriae, Klebsiella pneumoniae, Yersinia pestis, Vibrio cholerae, Hemophilus* influenza, *Rickettsia rickettsii, Chlamydia trachomatis, Mycoplasma* pneumonia, *Staphylococcus aureus, Streptococcus pneumoniae, Streptococcus pyogenes, Bacillus anthracis, Clostridium botulinum, Clostridium tetani, clostridium perfringens, Corynebacterium diphteriae,* Proprionibacterium acne, *Mycobacterium tuberculosis, Mycobacterium leprae* and *Listeriare monocytogenes*. Lower eukaryotic organism includes yeast and fungus such as *Pneumocystis nerinii, Candida albicans, Aspergillus, Histoplasma capsulatum, Blastomyces dermatitidis, Cryptococcus neoformans, Trichophyton* and *Microsporum*. Complex eukaryotic organism includes worms, insects, aracnids, nematodes, aemobe, *Entamoeba histolytica, Giardia lamblia, Trichonomonas vaginalis, Trypanosoma brucei gembiense, Trypanosoma cruzi, Blantidium coli, Toxoplasma gondii, Cryptosporidium* or *Leishmania*.

The compounds of the present invention are contemplated in the treatment of cancer, actinic keratosis, seborrheic keratosis, viral infections, bacterial infections, wound healing, and treatment of photodamaged skin.

In an embodiment of the invention the compounds of the invention are contemplated for use in the treatment of cutaneous warts, genital warts, actinic keratosis, squamous cell carcinoma (SCC), basal cell carcinoma (BCC), lentigo maligna, cervical intraepithelial neoplasia, anal intraepithelial neoplasia or vulva intraepithelial neoplasia.

In an embodiment of the invention the compounds of the invention are contemplated for use in the treatment of superficial basal cell carcinoma (BCC), nodular BCC, squamous cell carcinoma or squamous cell carcinoma in situ (SCCIS).

In an embodiment of the invention the compounds of the invention are contemplated for use in the treatment of actinic keratosis.

In an embodiment of the invention the compounds of the invention are contemplated for use in the treatment of Seborrheic keratosis.

In an embodiment of the invention the compounds of the invention are contemplated for use in the treatment of photodamaged skin.

In an embodiment of the invention the compounds of the invention are contemplated for use in the treatment of or lesions caused by HPV infection.

In an embodiment of the invention the lesions are common warts or genital warts.

In an embodiment of the invention the compounds of the invention are contemplated for use in the treatment of squamous cell carcinoma in situ or invasive squamous cell carcinoma.

In an embodiment of the invention the compounds of the invention are contemplated for use in the treatment of cutaneous squamous cell carcinoma, mucosal squamous cell carcinoma or head and neck squamous cell carcinoma.

In an embodiment of the invention the compounds of the invention are contemplated for use in the treatment of superficial basal cell carcinoma or nodular basal cell carcinoma.

In an embodiment of the invention the compounds of the invention are contemplated for use in the treatment of cutaneous warts or genital warts In an embodiment of the invention the compounds of the invention are contemplated for use in the treatment of common warts, plantar warts and flat warts.

In an embodiment of the invention the compounds of the invention are contemplated for use in the treatment of lentigo maligna.

In an embodiment of the invention the compounds of the invention are contemplated for use in the treatment of cervical intraepithelial neoplasia, anal intraepithelial neoplasia or vulva intraepithelial neoplasia.

In an embodiment of the invention the compounds of the invention are contemplated for use in the treatment of acute myeloid leukemia.

In an embodiment the invention provides a method of treatment of cancer, actinic keratosis, seborrheic keratosis, viral infections, bacterial infections, wound healing, and treatment of photodamaged skin by administration to a subject in need thereof a compound of formula I.

In an embodiment the invention provides a method of treatment actinic keratosis by administration to a subject in need thereof a compound of formula I.

In an embodiment the invention provides a method of treatment Seborrheic keratosis by administration to a subject in need thereof a compound of formula I.

In an embodiment the invention provides a method of treatment photodamaged skin by administration to a subject in need thereof a compound of formula I above.

In an embodiment the invention provides a method of treatment of lesions caused by HPV infection by administration to a subject in need thereof a compound of formula I.

In an embodiment the invention provides a method of treatment of common warts or genital warts by administration to a subject in need thereof a compound of formula I.

In an embodiment the invention provides a method of treatment of cutaneous squamous cell carcinoma, mucosal squamous cell carcinoma or head and neck squamous cell carcinoma by administration to a subject in need thereof a compound of formula I.

In an embodiment the invention provides a method of treatment of common warts, plantar warts and flat warts by administration to a subject in need thereof a compound of formula I.

In an embodiment the invention provides a method of treatment of lentigo maligna by administration to a subject in need thereof a compound of formula I.

In an embodiment the invention provides a method of treatment of cervical intraepithelial neoplasia, anal intraepithelial neoplasia or vulva intraepithelial neoplasia by administration to a subject in need thereof a compound of formula I.

Pharmaceutical Compositions of the Invention

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.01 mg and 100 mg, such as 0.1-50 mg of a compound of formula I. A suitable dosage of the compound of the invention will depend, inter alia, on the age and condition of the patient, the severity of the disease to be treated and other factors well known to the practising physician. The compound may be administered either orally, parenterally, topically, transdermally or interdermally+other routes according to different dosing schedules, e.g. daily, weekly or with monthly intervals. In general a single dose will be in the range from 0.001 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid, semisolid or liquid pharmaceutical diluents or carriers.

The term "usage unit" in connection with topical use means a unitary, i.e. a single dose, capable of being administered topically to a patient in an application per square centimeter of the treatment area of from 0.001 microgram to 1 mg and preferably from 0.05 microgram to 0.5 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or controlled release), rectal, parenteral (including subcutaneous, intraperitoneal, intramuscular, intraarticular and intravenous), transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, The Science and Practice of Pharmacy, 21ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifyring agents such as but not restricted to tragacanth, alginate, acacia, dextran, sodium carboxymethylcellulose, gelatin, methylcellulose, hydroxypropylmethylcellulose, hydroxypropylcellulose, carbomers, polyvinylpyrrolidone, polysorbates, sorbitan fatty acid esters. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Transdermal formulations may be in the form of a plaster, patch, microneedles, liposomal or nanoparticulate delivery systems or other cutaneous formulations applied to the skin.

Formulations suitable for topical, such as dermal, intradermal or ophthalmic administration include liquid or semisolid preparations such as liniments, lotions, gels, applicants, sprays, foams, filmforming systems, microneedles, micro- or nano-emulsions, oil-in-water or water-in-oil emulsions such as creams, ointments or pastes; or solutions or suspensions such as drops.

For topical administartion, the compound of formula I may typically be present in an amount of from 0.001 to 20% by weight of the composition, such as 0.01% to about 10%, but may also be present in an amount of up to about 100% of the composition.

In addition to the aforementioned ingredients, the formulations of a compound of formula I may include one or more additional ingredients such as diluents, buffers, flavouring agents, colourant, surface active agents, thickeners, penetration enhancing agents, solubility enhancing agents preservatives, e.g. methyl hydroxybenzoate (including anti-oxidants), emulsifying agents and the like.

Formulation of ingenol derivatives in a gel for topical application has been described in WO07/068963, which is incorporated by reference.

General Procedures, Preparations and Examples

All reactions were carried out under an argon atmosphere with dry solvents using anhydrous conditions unless otherwise stated. Dry diethyl ether (Et$_2$O), dichloromethane (CH$_2$Cl$_2$), acetonitrile (CH$_3$CN), toluene (PhMe), tetrahydrofuran (THF), methanol (MeOH), and triethylamine (Et$_3$N) were obtained by passing these previously degassed solvents through activated alumina columns. Reagents were purchased at the highest commercial quality and used without further purification, unless otherwise stated. Yields refer to chromatographically and spectroscopically ($^1$H NMR) homogeneous materials, unless otherwise stated. Reactions were monitored by thin layer chromatography (TLC) carried out on 0.25 mm E. Merck silica gel plates (60F-254) using UV light as visualizing agent and an acidic mixture of anisaldehyde, phosphomolybdic acid, or ceric ammonium molybdate, or basic aqueous potassium permanganate (KMnO$_4$), and heat as developing agents. E. Merck silica gel (60, particle size 0.0430-0.663 mm) was used for flash column chromatography. Preparative thin layer chromatography (PTLC) separations were carried out on 0.25 or 0.50 mm E. Merck silica gel plates (60F-254). Concentration of organic solvents was performed on a rotary evaporator under reduced pressure followed by further evacuation using a two-stage mechanical pump. NMR spectra were recorded on Bruker DRX-600, DRX-500 and AMX-400 instruments and calibrated using residual undeuterated solvent as an internal reference (CHCl$_3$ @ δ 7.26 ppm $^1$H NMR, δ 77.16 ppm $^{13}$C NMR; Benzene @ δ 7.16 ppm $^1$H NMR, δ 128.06 ppm $^{13}$C NMR). The following abbreviations (or combinations thereof) were used to explain $^1$H NMR multiplicities: s=singlet, d=doublet, t=triplet, q=quartet, p=quintet, m=multiplet, br=broad. High-resolution mass spectra (HRMS) were recorded on Agilent 6230 TOF LC/MS mass spectrometer by electrospray ionization time of flight reflectron experiments. IR spectra were recorded on a Perkin Elmer Spectrum BX FTIR spectrometer. Optical rotation were obtained on a Perkin-Elmer 341 polarimeter at 20° C., measured at 589 nm. Melting points were recorded on a Fisher-Johns 12-144 melting point apparatus and are reported uncorrected.

The following abbreviations have been used throughout:
DABCO 1,4-diazabicyclo[2.2.2]octane
DCE 1,2-dichloroethane
DCM dichloromethane
DMAP 4-dimethylaminopyridine
DMF N,N-Dimethylformamide
DMSO dimethyl sulfoxide
Et ethyl
EtOAc ethyl acetate
h hour(s)
HPLC High pressure liquid chromatography
HRMS High resolution mass spectroscopy
IR Infrared spectroscopy
L liter
m milli
Me methyl
MS Mass spectrometry
NIS N-iodosuccinimide
NMR nuclear magnetic resonance
PTLC preparative thin-layer chromatography
rt room temperature
RT Retention Time
TBS tert-butyl-dimethylsilyl
TFA trifluoroacetic acid
TMS Trimethylsilyl
TMSCI Trimethylsilyl chloride
TMSOTf Trimethylsilyl trifluoromethanesulfonate
THF tetrahydrofuran
v volume Preparations and Examples Intermediate 9

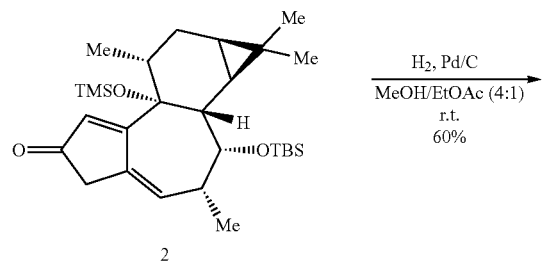

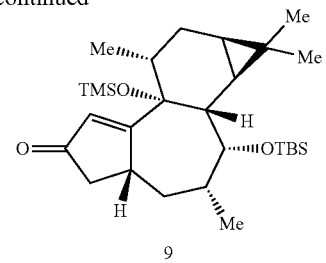

To a solution of 2 (obtained as described in Jørgensen, L.; McKerrall, S. J.; Kuttruff, C. A.; Ungeheuer, F.; Felding J.; Baran, P. S. *Science* 2013, 341, 878-882) (2.5 g, 5.12 mmol, 1.0 equiv) in MeOH (40 mL) and EtOAc (10 mL) was added 10% Pd/C (542 mg, 0.51 mmol, 0.1 equiv). Through the solution was bubbled H$_2$(g) at room temperature. The reaction mixture was stirred at room temperature for 30 minutes. Then the solvent was concentrated under reduced pressure. Purification of the crude product by flash column chromatography (silica gel, hexanes/EtOAc=10:1→5:1) afforded 9 (1.5 g, 60%) as colorless crystal.

Physical state: colorless crystal

R$_f$=0.5 (Hex/EtOAc=5:1; anisaldehyde)

HRMS (m/z): calcd for C$_{28}$H$_{51}$O$_3$Si$_2$, [M+H]$^+$, 491.3377. found, 491.3376.

[α]$_D$=+43.9° (c=0.8, EtOAc)

$^1$H NMR (400 MHz, Chloroform-d) δ 6.03 (s, 1H), 3.77 (s, 1H), 2.75-2.62 (m, 2H), 2.12 (d, J=17.0 Hz, 1H), 1.76-1.32 (m, 7H), 1.10 (s, 3H), 0.96 (s, 3H), 0.93 (d, J=6.7 Hz, 3H), 0.87 (s, 9H), 0.84-0.72 (m, 2H), 0.62 (d, J=6.9 Hz, 3H), 0.25 (s, 9H), 0.15 (s, 3H), 0.06 (s, 3H).

$^{13}$C NMR (101 MHz, Chloroform-d) δ 208.4, 192.1, 128.5, 83.0, 80.0, 52.0, 47.3, 44.0, 42.6, 41.9, 41.2, 28.9, 27.0, 26.9, 26.1, 21.9, 21.5, 19.2, 18.9, 17.6, 15.9, 5.1, −0.8, −4.1.

Intermediate 11

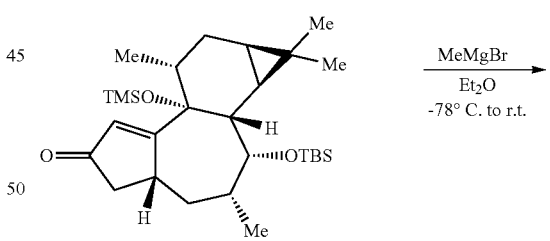

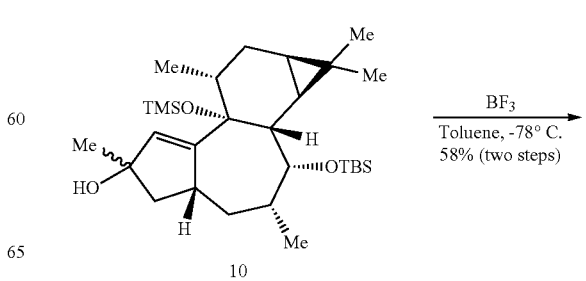

17

-continued

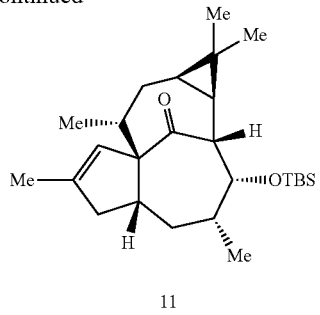

11

18

-continued

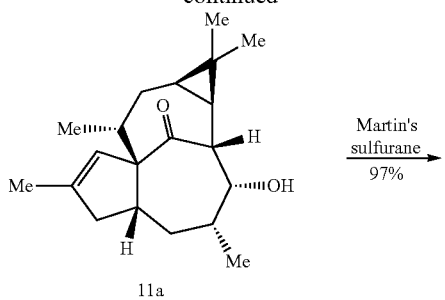

11a

To a solution of 9 (1.5 g, 3.06 mmol, 1.0 equiv) in Et₂O (50 mL) was added methylmagnesium bromide (3 M in Et₂O, 1.53 mL, 4.59 mmol, 1.5 equiv) over 5 minutes at −78° C. The reaction mixture was stirred at this temperature for 15 minutes before being warmed to 0° C. After 30 minutes, the reaction mixture was carefully quenched with water (100 mL). The mixture was extracted with Et₂O (3×100 mL) and the combined organic layers were dried over MgSO₄, filtered and concentrated under reduced pressure afforded crude 10 (1.5 g) as a light yellow foam. To a solution of crude 10 (1.5 g) in toluene (50 mL) was added BF₃·Et₂O (3.76 mL, 29.6 mmol, 9.7 equiv) over 5 minutes at −78° C. After 15 min, a 1:1 mixture of Et₃N/MeOH (24.6 mL) was slowly added, then the solution was allowed warm to room temperature. The solvent was concentrated under reduced pressure. Purification of the crude product by flash column chromatography (silica gel, hexanes/EtOAc=50:1→30:1) afforded 11 (745.4 mg, 58%, two steps) as a white foam.

Physical state: white foam $R_f$=0.22 (Hex/EtOAc=50:1; anisaldehyde)

HRMS (m/z): calcd for $C_{26}H_{45}O_2Si$, [M+H]⁺, 417.3189. found, 417.3185.

$[\alpha]_D$=+21.2° (c=0.65, EtOAc)

¹H NMR (400 MHz, Chloroform-d) δ 5.61 (s, 1H), 3.83 (d, J=3.8 Hz, 1H), 2.72 (dd, J=16.2, 7.3 Hz, 1H), 2.51 (d, J=12.2 Hz, 1H), 2.21 (dd, J=10.6, 7.4 Hz, 1H), 1.90-1.74 (m, 3H), 1.70 (d, J=1.4 Hz 3H), 1.72-1.64 (m, 3H), 1.11 (d, J=15.0 Hz, 1H), 1.08 (s, 3H), 1.04 (s, 3H), 0.94 (s, 9H), 0.90 (d, J=7.0 Hz, 3H), 0.89-0.83 (m, 1H), 0.86 (d, J=6.6 Hz, 3H), 0.67 (td, J=8.8, 5.9 Hz, 1H), 0.15 (s, 3H), 0.03 (s, 3H).

¹³C NMR (151 MHz, Chloroform-d) δ 208.0, 139.2, 125.0, 76.4, 73.6, 52.1, 45.6, 45.2, 45.1, 40.7, 38.7, 29.9, 28.8, 26.2, 24.4, 23.6, 23.3, 19.8, 18.5, 17.3, 16.6, 15.8, −3.7, −4.6.

Intermediate 16

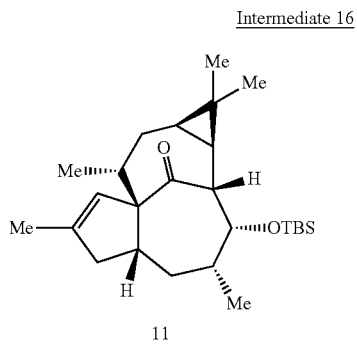

11

TBAF
——→
50%

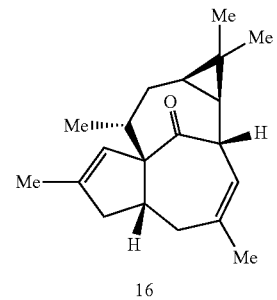

16

To a solution of 11 (496 mg, 1.19 mmol, 1.0 equiv) in THF (5 mL) was added TBAF (1 M, 5.95 mL, 5.95 mmol, 5.0 equiv) and H₂O (53 mg, 2.94 mmol, 2.5 equiv) at room temperature. The flask was sealed with a plastic cap and the reaction mixture was heated to 60° C. After 2 days, the reaction mixture was cooled to room temperature then water (5 mL) was added. The mixture was extracted with Et₂O (3×10 mL) and the combined organic layers were dried over MgSO₄, filtered and concentrated under reduced pressure. Purification of the crude product by flash column chromatography (silica gel, hexanes/EtOAc=10:1) afforded 11a (178.3 mg, 50%).

To a solution of 11a (178.3 mg, 0.59 mmol, 1.0 equiv) in CHCl₃ (3 mL) was added Martin's sulfurane (540 mg, 0.80 mmol, 1.4 equiv) at room temperature. The reaction mixture was stirred at room temperature for 30 minutes. Then CHCl₃ was removed under reduced pressure. Purification of the crude product by flash column chromatography (silica gel, hexanes/EtOAc=30:1→20:1) afforded 16 (162.6 mg, 97%) as a pale yellow oil.

Physical state: pale yellow oil $R_f$=0.5 (Hex/EtOAc=10:1; anisaldehyde)

HRMS (m/z): calcd for $C_{20}H_{29}O$, [M+H]⁺, 285.2218. found, 285.2211.

$[\alpha]_D$=+0.7° (c=0.42, EtOAc)

¹H NMR (400 MHz, Chloroform-d) δ 5.62 (s, 1H), 5.58 (s, 1H), 3.63 (d, J=10.2 Hz, 1H), 2.69-2.60 (m, 2H), 2.11-2.08 (m, 2H), 2.05-1.96 (m, 1H), 1.84 (dt, J=15.7, 5.6 Hz, 1H), 1.76-1.69 (m, 1H), 1.74 (s, 3H), 1.61 (d, J=14.9 Hz, 1H), 1.58 (s, 3H), 1.09 (s, 3H), 1.05 (s, 3H), 0.95 (d, J=7.1 Hz, 3H), 0.86 (dd, J=12.1, 8.4 Hz, 1H), 0.70 (td, J=8.6, 6.2 Hz, 1H).

¹³C NMR (151 MHz, Chloroform-d) δ 209.8, 140.4, 137.9, 122.6, 122.0, 76.6, 45.3, 43.4, 42.4, 38.4, 30.7, 28.8, 24.5, 23.6, 23.5, 23.1, 17.5, 16.9, 15.6.

Intermediate 17

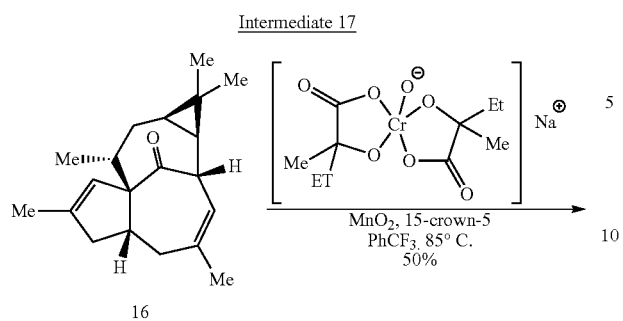 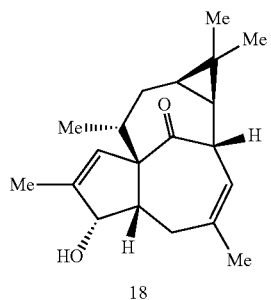

To a flame-dried 25 mL flask equipped with a stir bar were added 16 (21.3 mg, 0.075 mmol, 1.0 equiv), Cr(V) reagent (124.1 mg, 0.384 mmol, 5.0 equiv) and manganese (IV) oxide (324.6 mg, 49.8 equiv). The flask was evacuated and filled back with argon, followed by adding α,α,α-trifluorotoluene (5 mL) and 15-crown-5 (74 μL). The vial was sealed with a septum cap and heated to 80° C. for 24 hours. The reaction mixture was filtered through a two-layered plug of silica and celite (hexanes/EtOAc=1:1) to give a clear yellow solution, which was concentrated to yellow oil. Purification of the crude product by flash column chromatography (silica gel, hexanes/EtOAc=20:1→10:1) afforded 17 (11.1 mg, 50%) as a pale yellow oil.

Physical state: pale yellow oil $R_f$=0.4 (Hex/EtOAc=5:1; anisaldehyde)

HRMS (m/z): calcd for $C_{20}H_{27}O_2$, $[M+H]^+$, 299.2011. found, 299.2011.

$[\alpha]_D$=+74.6° (c=0.26, $CH_2Cl_2$)

$^1$H NMR (600 MHz, Chloroform-d) δ 7.51 (s, 1H), 5.67 (s, 1H), 3.61 (d, J=10.1 Hz, 1H), 2.71 (dd, J=12.4, 4.0 Hz, 1H), 2.43 (dd, J=18.3, 3.8 Hz, 1H), 1.98 (ddt, J=9.4, 6.6, 2.6 Hz, 1H), 1.95-1.85 (m, 2H), 1.85-1.74 (m, 1H), 1.81 (d, J=1.5 Hz, 3H), 1.61 (s, 3H), 1.11 (s, 3H), 1.07 (s, 3H), 0.99 (d, J=6.9 Hz, 3H), 0.96 (dd, J=11.9, 8.5 Hz, 1H), 0.78-0.73 (m, 1H).

$^{13}$C NMR (151 MHz, Chloroform-d) δ 207.8, 206.2, 155.4, 140.7, 136.0, 122.1, 70.5, 52.8, 45.6, 42.9, 39.5, 31.6, 28.8, 24.2, 23.8, 23.5, 23.3, 17.8, 15.5, 10.7.

To a solution of 17 (11.1 mg, 0.037 mmol, 1.0 equiv) in MeOH (1 mL) at 0° C., was slowly added $NaBH_4$ (7.1 mg, 0.187 mmol, 5.0 equiv). The reaction mixture was stirred at 0° C. for 5 minutes before quenched with $H_2O$ (2 mL). The mixture was extracted with $Et_2O$ (3×5 mL) and the combined organic layers were dried over $MgSO_4$, filtered and concentrated under reduced pressure. Purification of the crude product by flash column chromatography (silica gel, hexanes/EtOAc=5:1) afforded 18 (10.1 mg, 90%) as a colorless crystal.

Physical state: colorless crystal $R_f$=0.2 (Hex/EtOAc=5:1; anisaldehyde)

HRMS (m/z): calcd for $C_{20}H_{29}O_2$, $[M+H]^+$, 301.2168. found, 301.2168.

$[\alpha]_D$=−5.6° (c=0.18, $CH_2Cl_2$)

$^1$H NMR (600 MHz, Chloroform-d) δ 5.77-5.70 (m, 1H), 5.66 (dq, J=4.8, 1.5 Hz, 1H), 4.72-4.65 (m, 1H), 3.67 (d, J=11.8 Hz, 1H), 2.75 (ddd, J=10.3, 6.2, 3.9 Hz, 1H), 2.53 (dd, J=17.9, 3.7 Hz, 1H), 2.11 (td, J=6.8, 3.1 Hz, 1H), 1.95 (dd, J=17.8, 10.6 Hz, 2H), 1.85 (dt, J=15.8, 6.3 Hz, 1H), 1.82-1.76 (m, 1H), 1.79 (t, J=1.3 Hz, 3H), 1.66 (s, 3H), 1.12 (s, 3H), 1.04 (s, 3H), 0.94 (dd, J=11.8, 8.5 Hz, 2H), 0.89 (d, J=7.0 Hz, 3H), 0.68 (q, J=7.4 Hz, 1H).

$^{13}$C NMR (151 MHz, Chloroform-d) δ 210.1, 142.5, 137.9, 125.0, 122.2, 78.6, 73.1, 48.3, 45.0, 37.5, 33.7, 31.3, 28.8, 24.9, 23.9, 23.34, 23.26, 17.2, 15.6, 13.9.

Intermediate 18

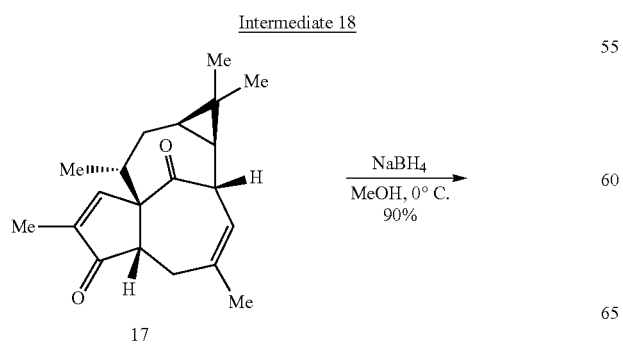

Intermediate 19

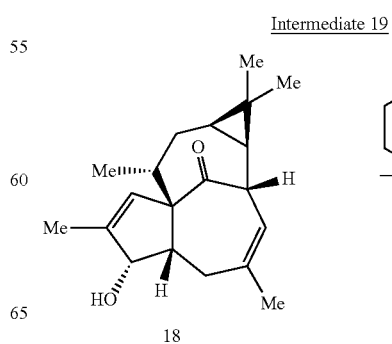

-continued

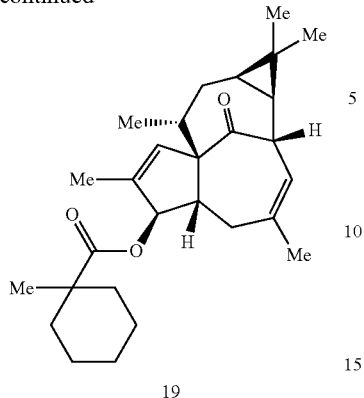

19

To a solution of 18 (7.0 mg, 0.023 mmol, 1.0 equiv) in THF (1 mL) was added 1-methylcyclohexanecarboxylic acid (16.6 mg, 0.116 mmol, 5.0 equiv) and triphenylphosphane (30.6 mg, 0.116 mmol, 5.0 equiv) at room temperature. Then DIAD (23 μL, 0.116 mmol, 5.0 equiv) was slowly added during 1 minute. The reaction mixture was stirred at room temperature for 5 minutes before water (5 mL) was added. The mixture was extracted with Et$_2$O (3×10 mL) and the combined organic layers were dried over MgSO$_4$, filtered and concentrated under reduced pressure. Purification of the crude product by flash column chromatography (silica gel, hexanes/EtOAc=50:1→30:1) afforded 19 (4.4 mg, 45%) as a colorless oil.

Physical state: colorless oil
R$_f$=0.2 (Hex/EtOAc=20:1; anisaldehyde)
HRMS (m/z): calcd for C$_{28}$H$_{40}$NaO$_3$, [M+Na]$^+$, 447.2875. found, 447.2884.
[α]$_D$=+16.4° (c=0.44, CH$_2$Cl$_2$)
$^1$H NMR (600 MHz, Chloroform-d) δ 6.04 (s, 1H), 5.62 (s, 1H), 4.82 (s, 1H), 3.51 (d, J=11.7 Hz, 1H), 2.47 (s, 1H), 2.45 (dd, J=15.9, 3.4 Hz, 1H), 2.18-2.08 (m, 1H), 2.01 (d, J=12.3 Hz, 2H), 1.96-1.87 (m, 1H), 1.82 (dt, J=15.7, 5.8 Hz, 1H), 1.77 (d, J=1.3 Hz, 3H), 1.67 (ddd, J=15.7, 9.1, 2.6 Hz, 1H), 1.59 (s, 4H), 1.58-1.51 (m, 2H), 1.38-1.19 (m, 6H), 1.14 (s, 3H), 1.07 (s, 3H), 1.04 (s, 3H), 1.01 (d, J=7.1 Hz, 3H), 0.85 (dd, J=12.1, 8.4 Hz, 1H), 0.69 (td, J=8.8, 6.3 Hz, 1H).
$^{13}$C NMR (151 MHz, Chloroform-d) δ 208.3, 178.1, 138.0, 136.9, 131.8, 122.2, 85.9, 75.4, 49.3, 45.4, 43.4, 41.4, 40.0, 35.7, 30.5, 28.8, 25.8, 24.3, 23.5, 23.4, 23.4, 22.9, 16.7, 15.6, 15.3.

Example 5

4,5-dideoxyingenol 3-(1-methyl-cyclohexanecarboxylate) (Compound 5)

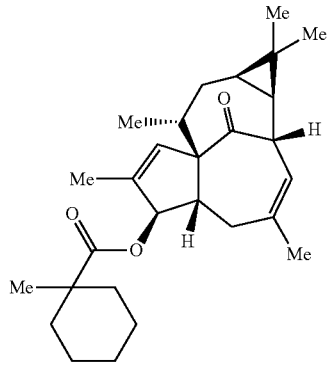

19

-continued

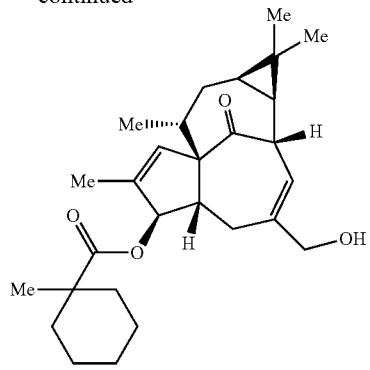

5

To a solution of 19 (4.0 mg, 0.0094 mmol, 1.0 equiv) in THF (1 mL) was added SeO$_2$ (5.2 mg, 0.0465 mmol, 4.9 equiv) at room temperature. The flask was sealed with a plastic cap and the suspension was heated to 60° C. for 1 hour. After cooled to room temperature, the reaction mixture was filtered through a plug of silica gel (hexanes/EtOAc=1:1) to give a clear yellow solution, which was concentrated to yellow oil that was dissolved into MeOH (1 mL) at −78° C. The solution was added CeCl$_3$.7H$_2$O (17.6 mg, in 0.5 mL MeOH, 0.0472 mmol, 5.0 equiv), immediately after the addition, the solid NaBH$_4$ (1.8 mg, 0.0474 mmol, 5.0 equiv) was slow added to the flask. After 10 minutes at −78° C., H$_2$O (5 mL) was carefully added to quench this reaction which was diluted with Et$_2$O (5 mL). The mixture was extracted with Et$_2$O (3×5 mL) and the combined organic layers were dried over MgSO$_4$, filtered and concentrated under reduced pressure. Purification of the crude product by flash column chromatography (silica gel, hexanes/EtOAc=2:1) afforded 5 (2.1 mg, 51%) as a colorless oil.

Physical state: colorless oil
R$_f$=0.25 (Hex/EtOAc=2:1; anisaldehyde)
HRMS (m/z): calcd for C$_{28}$H$_{40}$NaO$_4$, [M+Na]$^+$, 463.2824. found, 463.2822.
[α]$_D$=+20.0° (c=0.21, CH$_2$Cl$_2$)
$^1$H NMR (600 MHz, Chloroform-d) δ 6.02 (s, 1H), 5.94 (s, 1H), 4.89 (s, 1H), 3.91 (s, 2H), 3.56 (d, J=11.6 Hz, OH), 2.58 (dd, J=18.1, 3.0 Hz, 1H), 2.47 (dd, J=12.5, 3.3 Hz, 1H), 2.20-2.13 (m, 1H), 2.04-1.97 (m, 3H), 1.85 (dt, J=15.8, 5.8 Hz, 1H), 1.77 (d, J=1.3 Hz, 3H), 1.69 (ddd, J=16.0, 8.9, 2.7 Hz, 1H), 1.60-1.55 (m, 2H), 1.39-1.19 (m, 6H), 1.15 (s, 3H), 1.08 (s, 3H), 1.05 (s, 3H), 1.01 (d, J=7.1 Hz, 3H), 0.90 (dd, J=12.0, 8.4 Hz, 1H), 0.73 (td, J=8.5, 6.3 Hz, 1H).
$^{13}$C NMR (151 MHz, Chloroform-d) δ 207.9, 140.3, 138.4, 131.4, 123.7, 85.6, 75.3, 67.1, 49.2, 45.2, 43.4, 41.3, 35.6, 35.2, 30.6, 28.7, 25.8, 23.6, 23.5, 23.4, 22.8, 16.8, 15.6, 15.3.

Intermediate 20 and 21

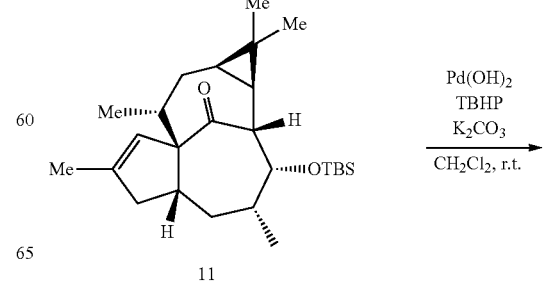

11

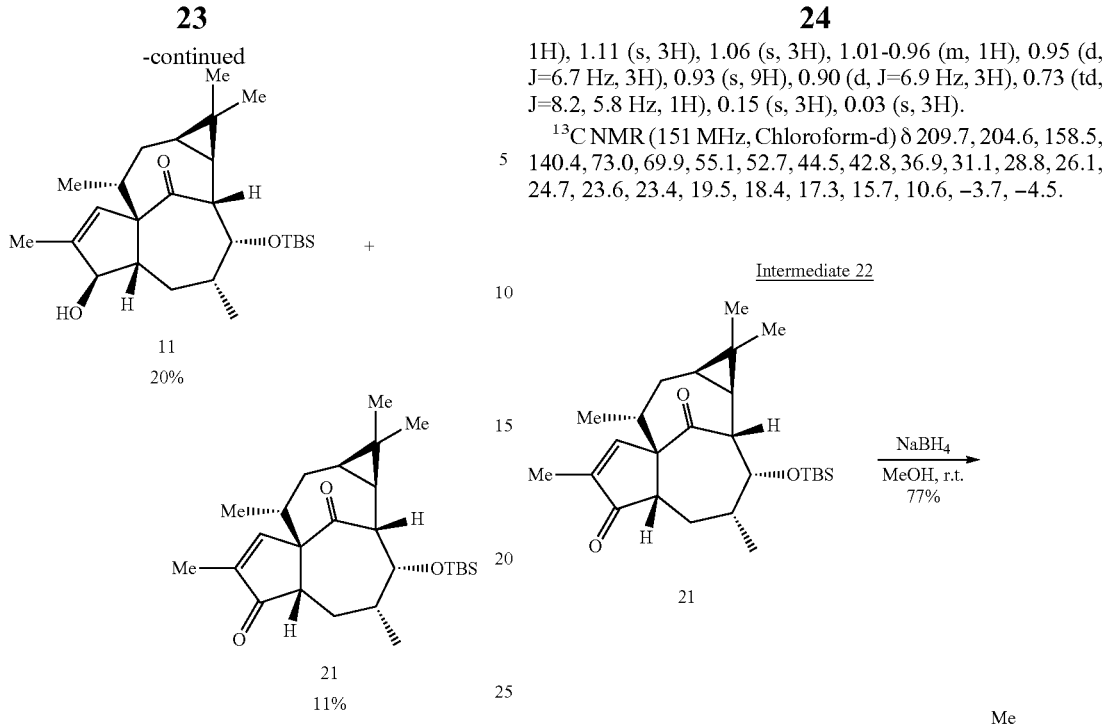

To a solution of 11 (519.0 mg, 1.247 mmol, 1.0 equiv) in CH$_2$Cl$_2$ (8 mL) was added 20% Pd(OH)$_2$ on carbon (66 mg, 0.125 mmol, 0.1 equiv) and K$_2$CO$_3$ (43 mg, 0.312 mmol, 0.25 equiv) at room temperature. The mixture was cooled to 4° C., and TBHP (5.5 M in decane, 1.13 mL, 6.215 mmol, 5.0 equiv) was added with vigorous stirring. Then the reaction mixture was allowed to warm up to room temperature. After 24 hours, the reaction mixture was filtered through a plug of silica gel (washed with CH$_2$Cl$_2$). The solvent was removed under reduced pressure. Purification of the crude product by flash column chromatography (silica gel, hexanes/EtOAc=20: 1→5:1) afforded 20 (105.1 mg, 20%) and 21 (60 mg, 11%).

Spectroscopic data for 20:
Physical state: colorless oil
R$_f$=0.25 (Hex/EtOAc=5:1; anisaldehyde)
HRMS (m/z): calcd for C$_{26}$H$_{44}$NaO$_3$Si, [M+Na]$^+$, 455.2957. found, 455.2959.
[α]$_D$=+49.4° (c=0.34, CH$_2$Cl$_2$)
$^1$H NMR (600 MHz, Chloroform-d) δ 5.98 (d, J=1.7 Hz, 1H), 3.96 (s, 1H), 3.85 (d, J=3.9 Hz, 1H), 2.51 (d, J=12.2 Hz, 1H), 2.15 (dd, J=10.6, 1.8 Hz, 1H), 2.09-2.02 (m, 1H), 1.87-1.80 (m, 2H), 1.80 (d, J=1.5 Hz, 3H), 1.78-1.73 (m, 1H), 1.35-1.29 (m, 1H), 1.27 (dd, J=15.6, 3.4 Hz, 1H), 1.09 (s, 3H), 1.04 (s, 3H), 0.97 (d, J=7.1 Hz, 3H), 0.93 (s, 9H), 0.88 (d, J=6.9 Hz, 3H), 0.86 (dd, J=12.2, 8.6 Hz, 1H), 0.67 (td, J=9.2, 6.2 Hz, 1H), 0.14 (s, 3H), 0.03 (s, 3H).
$^{13}$C NMR (151 MHz, Chloroform-d) δ 206.6, 140.5, 132.0, 87.9, 75.0, 73.7, 54.1, 52.2, 44.9, 42.1, 38.2, 30.0, 28.7, 26.2, 24.3, 23.6, 23.0, 19.8, 18.4, 16.3, 15.7, 14.9, −3.7, −4.6.

Spectroscopic data for 21:
Physical state: colorless crystal
R$_f$=0.33 (Hex/EtOAc=10:1; anisaldehyde)
HRMS (m/z): calcd for C$_{26}$H$_{42}$NaO$_3$Si, [M+Na]$^+$, 453.2801. found, 453.2809.
[α]$_D$=+98.2° (c=0.17, CH$_2$Cl$_2$)
$^1$H NMR (600 MHz, Chloroform-d) δ 7.59 (s, 1H), 3.87 (d, J=3.6 Hz, 1H), 2.57 (d, J=12.1 Hz, 1H), 2.38 (d, J=10.8 Hz, 1H), 1.92-1.81 (m, 3H), 1.79-1.76 (m, 1H) 1.77 (d, J=1.5 Hz, 3H), 1.59 (dq, J=15.2, 1.6 Hz, 1H), 1.27 (dt, J=15.0, 11.4 Hz, 1H), 1.11 (s, 3H), 1.06 (s, 3H), 1.01-0.96 (m, 1H), 0.95 (d, J=6.7 Hz, 3H), 0.93 (s, 9H), 0.90 (d, J=6.9 Hz, 3H), 0.73 (td, J=8.2, 5.8 Hz, 1H), 0.15 (s, 3H), 0.03 (s, 3H).
$^{13}$C NMR (151 MHz, Chloroform-d) δ 209.7, 204.6, 158.5, 140.4, 73.0, 69.9, 55.1, 52.7, 44.5, 42.8, 36.9, 31.1, 28.8, 26.1, 24.7, 23.6, 23.4, 19.5, 18.4, 17.3, 15.7, 10.6, −3.7, −4.5.

To a solution of 21 (60.0 mg, 0.14 mmol, 1.0 equiv) in MeOH (2 mL) at room temperature, was slowly added NaBH$_4$ (26.5 mg, 0.70 mmol, 5.0 equiv). The reaction mixture was stirred at room temperature for 5 minutes, and diluted with Et$_2$O (5 mL), then quenched with H$_2$O (5 mL). The mixture was extracted with Et$_2$O (3×5 mL) and the combined organic layers were dried over MgSO$_4$, filtered and concentrated under reduced pressure. Purification of the crude product by flash column chromatography (silica gel, hexanes/EtOAc=5:1) afforded 22 (47.2 mg, 77%) as a white foam.

Physical state: white foam
R$_f$=0.4 (Hex/EtOAc=4:1; anisaldehyde)
HRMS (m/z): calcd for C$_{26}$H$_{44}$NaO$_3$Si, [M+Na]$^+$, 455.2957. found, 455.2956.
[α]$_D$=+20.5° (c=0.2, CH$_2$Cl$_2$)
$^1$H NMR (600 MHz, Chloroform-d) δ 5.86 (t, J=1.8 Hz, 1H), 4.77 (s, 1H), 3.88 (d, J=3.9 Hz, 1H), 2.52 (d, J=12.2 Hz, 1H), 2.43 (dd, J=10.9, 6.7 Hz, 1H), 1.88 (ddd, J=7.1, 4.5, 2.8 Hz, 1H), 1.82 (ddd, J=15.6, 6.0, 4.5 Hz, 1H), 1.75-1.68 (m, 3H), 1.72 (t, J=1.5 Hz, 3H), 1.34-1.23 (m, 2H), 1.09 (s, 3H), 1.04 (s, 3H), 0.94 (s, 9H), 0.92 (d, J=6.8 Hz, 3H), 0.89 (d, J=7.3 Hz, 3H), 0.88-0.85 (m, 1H), 0.66 (ddd, J=9.7, 8.6, 6.1 Hz, 1H), 0.15 (s, 3H), 0.03 (s, 3H).
$^{13}$C NMR (151 MHz, Chloroform-d) δ 206.5, 140.6, 127.3, 77.5, 73.8, 73.0, 52.2, 49.9, 45.0, 38.2, 30.2, 28.7, 28.4, 26.2, 24.4, 23.8, 23.1, 19.9, 18.4, 16.8, 15.8, 13.6, −3.7, −4.6.

Intermediate 23

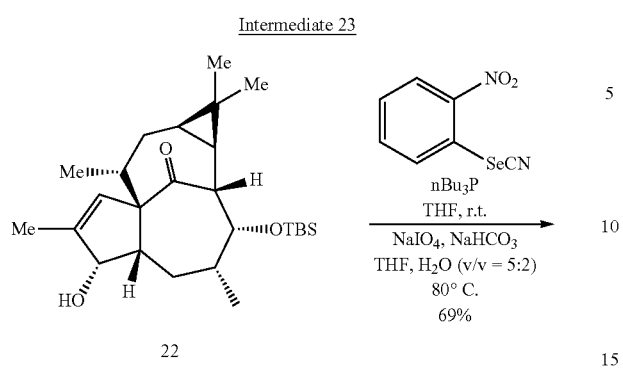

22

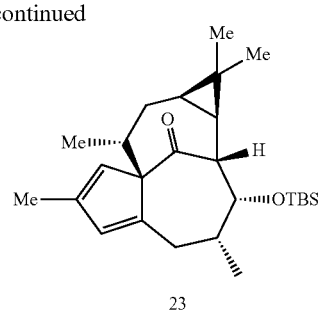

23

To a solution of 22 (46.2 mg, 0.107 mmol, 1.0 equiv) in THF (2 mL) was added 1-nitro-2-selenocyanatobenzene (29.0 mg, 0.127 mmol, 1.2 equiv) at room temperature. Then to this reaction mixture was slowly added n-Bu₃P (53 µL, 0.212 mmol, 2.0 equiv) at room temperature. After 30 minutes, the reaction mixture was filtered through a plug of silica gel (Hexanes/EtOAc=10:1). The solvent was removed under reduced pressure. The crude product was dissolved in THF (5 mL). To this solution was added H₂O (2 mL), NaIO₄ (228.9 mg, 1.070 mmol, 10.0 eq.) and Na₂CO₃ (53.0 mg, 0.639 mmol, 6.0 equiv). The flask was sealed with a plastic cap and the reaction mixture was heated to 80° C. for 2 hours. The reaction mixture was filtered through Buchner funnel. The filter liquor was extracted with Et₂O (3×5 mL) and the combined organic layers were dried over MgSO₄, filtered and concentrated under reduced pressure. Purification of the crude product by flash column chromatography (silica gel, hexanes/EtOAc=20:1) afforded 23 (30.5 mg, 69%).

Intermediate 23

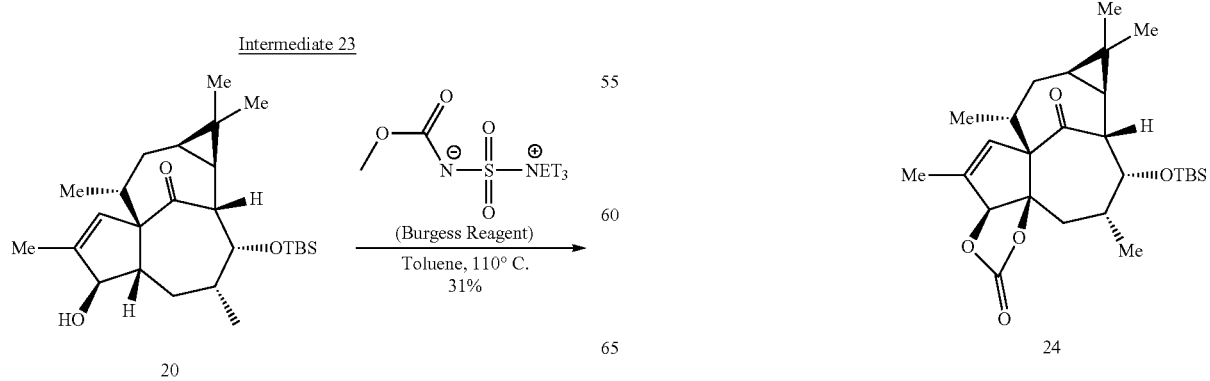

20

23

To a solution of 20 (78.0 mg, 0.18 mmol, 1.0 equiv) in toluene (2 mL) was added Burgess Reagent (56.0 mg, 0.24 mmol, 1.3 equiv) at room temperature under Argon atmosphere. The reaction mixture was stirred at 110° C. for 1 minute. Then solvent was removed under reduced pressure. Purification of the crude product by flash column chromatography (silica gel, hexanes/EtOAc=20:1) afforded 23 (23.3 mg, 31%).

Physical state: pale yellow foam
$R_f$=0.5 (Hex/EtOAc=10:1; anisaldehyde)
HRMS (m/z): calcd for $C_{26}H_{42}NaO_2Si$, $[M+Na]^+$, 437.2852. found, 437.2853.
$[\alpha]_D$=−54.7° (c=0.17, $CH_2Cl_2$)
¹H NMR (600 MHz, Chloroform-d) δ 5.98 (s, 1H), 5.92 (s, 1H), 4.09 (dd, J=8.6, 3.8 Hz, 1H), 3.26 (dd, J=11.5, 3.9 Hz, 1H), 2.71 (d, J=14.5 Hz, 1H), 2.55 (h, J=6.9 Hz, 1H), 2.48 (dd, J=14.5, 5.3 Hz, 1H), 2.43-2.34 (m, 1H), 2.10-2.00 (m, 2H), 1.90 (d, J=1.6 Hz, 3H), 1.21 (s, 3H), 1.11 (dd, J=11.4, 9.1 Hz, 1H), 1.03 (s, 3H), 0.92 (s, 9H), 0.73 (dt, J=8.7, 4.1 Hz, 1H), 0.66 (d, J=7.5 Hz, 3H), 0.62 (d, J=6.5 Hz, 3H), 0.06 (s, 2H), 0.03 (s, 3H).
¹³C NMR (151 MHz, Chloroform-d) δ 208.0, 142.4, 142.3, 136.5, 130.5, 81.1, 71.6, 46.8, 37.7, 36.8, 33.4, 33.1, 29.0, 26.0, 24.8, 24.1, 21.4, 18.5, 18.4, 15.6, 15.4, 13.4, −4.6, −4.7.

Intermediate 24

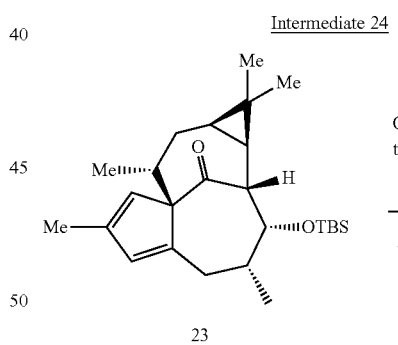

23

24

To a solution of 23 (46.2 mg, 0.107 mmol, 1.0 equiv) in t-BuOH (1 mL) and H$_2$O (1 mL) was added OsO$_4$ (2.5 wt % in t-BuOH, 0.31 mL, 0.0214 mmol 0.2 equiv) and NMO (50% w/w in H$_2$O, 0.15 mL, 0.642 mmol, 6.0 equiv) at room temperature. The reaction mixture was stirred at 80° C. for 4 hours. Saturated Na$_2$SO$_3$ (5 mL) was added and the mixture was extracted with Et$_2$O (3×5 mL) and the combined organic layers were dried over MgSO$_4$, filtered and concentrated under reduced pressure. The crude product was dissolved in toluene (2 mL). To this solution was added CDI (54 mg, 0.333 mmol, 3.1 equiv) at room temperature. The reaction mixture was allowed to stir overnight at room temperature before quenched with H$_2$O (2 mL). The mixture was extracted with Et$_2$O (3×5 mL) and the combined organic layers were dried over MgSO$_4$, filtered and concentrated under reduced pressure. Purification of the crude product by flash column chromatography (silica gel, hexanes/EtOAc=20:1) afforded 24 (38.8 mg, 65%) as a colorless oil.

Physical state: colorless oil $R_f$=0.2 (Hex/EtOAc=20:1; anisaldehyde)

HRMS (m/z): calcd for C$_{27}$H$_{43}$O$_5$Si, [M+H]$^+$, 475.2880. found, 475.2882.

[α]$_D$=+19.6° (c=0.27, CH$_2$Cl$_2$)

$^1$H NMR (600 MHz, Chloroform-d) δ 6.03 (d, J=1.8 Hz, 1H), 4.55 (s, 1H), 3.86 (d, J=3.3 Hz, 1H), 2.72 (d, J=11.8 Hz, 1H), 2.30-2.20 (m, 1H), 2.21-2.11 (m, 1H), 2.01 (ddd, J=15.9, 6.6, 2.7 Hz, 1H), 1.91 (dd, J=15.5, 11.4 Hz, 1H), 1.87 (d, J=1.6 Hz, 3H), 1.81 (ddd, J=16.0, 7.6, 6.5 Hz, 1H), 1.61 (d, J=15.6, 1H), 1.15 (s, 3H), 1.04 (s, 3H), 1.00 (dd, J=11.8, 8.8 Hz, 1H), 0.94 (s, 9H), 0.93 (d, J=6.6 Hz, 3H), 0.85 (d, J=6.8 Hz, 3H), 0.67 (dt, J=8.8, 6.5 Hz, 1H), 0.16 (s, 3H), 0.05 (s, 3H).

$^{13}$C NMR (151 MHz, Chloroform-d) δ 205.0, 154.4, 135.1, 134.7, 95.1, 90.0, 77.1, 72.7, 52.4, 41.7, 39.0, 31.2, 28.8, 26.1, 25.0, 23.6, 23.2, 19.8, 18.4, 15.7, 15.3, −3.6, −4.4.

Intermediate 25

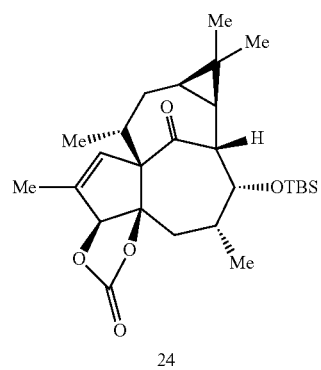

24

A plastic falcon tube was charged with 24 (38.8 mg, 0.082 mmol, 1.0 equiv) and CH$_3$CN (3 mL). 48% aqueous HF (0.15 mL, 3.60 mmol, 43.9 equiv) was added and mixture was heated to 50° C. After 3 hours the reaction mixture was cooled to room temperature and quenched by the slow addition of saturated aqueous Na$_2$SO$_3$ (6 mL). The mixture was extracted with EtOAc (3×8 mL) and the combined organic layers were dried over MgSO$_4$, filtered and concentrated under reduced pressure. Purification of the crude product by flash column chromatography (silica gel, hexanes/EtOAc=4:1) afforded 25 (25.0 mg, 85%) as a colorless crystal.

Physical state: colorless crystal $R_f$=0.25 (Hex/EtOAc=3:1; anisaldehyde)

HRMS (m/z): calcd for C$_{21}$H$_{28}$NaO$_5$, [M+Na]$^+$, 383.1834. found, 383.1848.

[α]$_D$=+12.7° (c=0.15, CH$_2$Cl$_2$)

$^1$H NMR (600 MHz, Chloroform-d) δ 5.92 (d, J=1.6 Hz, 1H), 4.58 (s, 1H), 3.87 (s, 1H), 3.19 (d, J=7.8 Hz, 1H), 2.87 (dd, J=11.3, 1.2 Hz, 1H), 2.34 (ddd, J=9.6, 6.9, 2.5 Hz, 1H), 2.15 (dtq, J=16.9, 6.9, 3.5 Hz, 1H), 2.08-1.99 (m, 1H), 1.90 (d, J=1.5 Hz, 3H), 1.84 (ddd, J=16.1, 9.6, 6.6 Hz, 1H), 1.75 (dd, J=15.8, 11.3 Hz, 1H), 1.69 (dd, J=15.6, 2.4 Hz, 1H), 1.18 (s, 3H), 1.11 (dd, J=11.3, 8.9 Hz, 1H), 1.040 (s, 3H), 1.037 (d, J=7.2 Hz, 3H), 0.81 (d, J=6.8 Hz, 3H), 0.71 (ddd, J=8.9, 6.5, 4.6 Hz, 1H).

$^{13}$C NMR (151 MHz, Chloroform-d) δ 211.9, 154.0, 136.4, 133.1, 94.4, 89.4, 76.8, 72.2, 50.0, 41.7, 38.4, 37.6, 31.7, 29.0, 23.9, 23.7, 22.5, 19.3, 18.7, 15.4, 15.2.

Intermediate 26

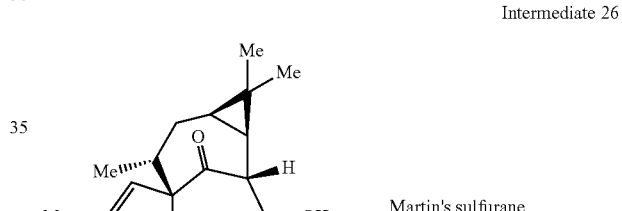

25

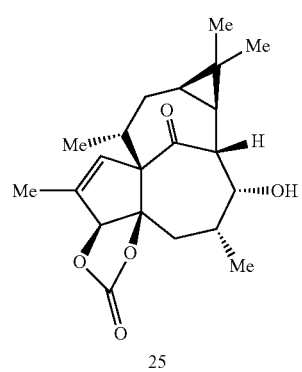

26

To a solution of 25 (23 mg, 0.064 mmol, 1.0 equiv) in toluene (2 mL) was added Martin's sulfurane (86 mg, 0.128 mmol, 2.0 equiv) at room temperature. The solution was heated to 110° C. for 10 minutes. Then toluene was removed under reduced pressure. Purification of the crude product by flash column chromatography (silica gel, hexanes/EtOAc=20:1) afforded 26 (21.1 mg, 96%) as a colorless oil.

Physical state: colorless oil
R$_f$=0.25 (Hex/EtOAc=5:1; anisaldehyde)
HRMS (m/z): calcd for C$_{21}$H$_{27}$O$_4$, [M+H]$^+$, 343.1909. found, 343.1902.
[α]$_D$=−2.8° (c=0.18, CH$_2$Cl$_2$)
$^1$H NMR (600 MHz, Chloroform-d) δ 6.10 (q, J=1.6 Hz, 1H), 5.81-5.71 (m, 1H), 4.53 (s, 1H), 3.65 (d, J=10.9 Hz, 1H), 2.65 (d, J=18.3 Hz, 1H), 2.40 (d, J=18.2, Hz, 1H), 2.25 (td, J=6.8, 2.8 Hz, 1H), 2.14 (ddd, J=16.1, 7.4, 2.9 Hz, 1H), 1.91 (d, J=1.6 Hz, 3H), 1.84 (dt, J=16.1, 6.5 Hz, 1H), 1.67 (s, 1H), 1.16 (s, 3H), 1.06 (s, 3H), 0.99-0.95 (m, 1H), 0.97 (d, J=6.8 Hz, 3H), 0.72 (dt, J=8.4, 7.1 Hz, 1H).
$^{13}$C NMR (151 MHz, Chloroform-d) δ 206.3, 154.0, 135.1, 134.4, 132.9, 124.1, 92.4, 90.9, 77.8, 46.1, 44.9, 39.6, 31.4, 28.8, 24.1, 23.6, 23.5, 18.3, 15.6, 15.5.

Intermediate 27

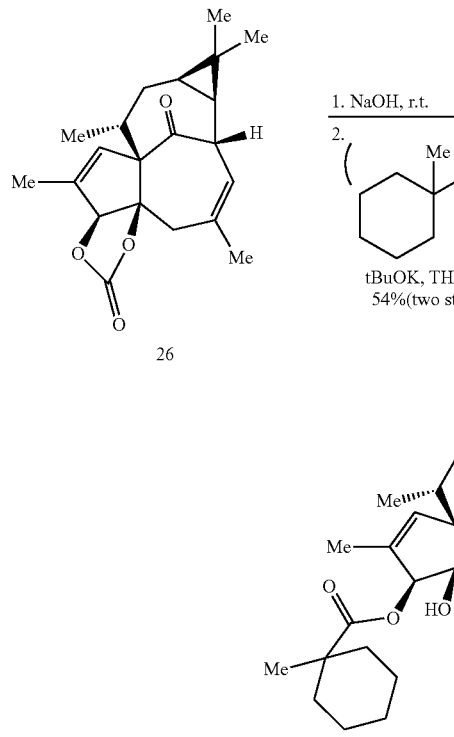

To a solution of 26 (4.2 mg, 0.0123 mmol, 1.0 equiv) in THF (0.5 mL) was added 10% NaOH$_{(aq)}$ (0.5 mL) at room temperature. After 1 hour the reaction mixture was quenched with saturated NH$_4$Cl$_{(aq)}$ (2 mL). The mixture was extracted with Et$_2$O (5×3 mL) and the combined organic layers were dried over MgSO$_4$, filtered and concentrated under reduced pressure. The crude product and 1-methylcyclohexane-1-carboxylic anhydride (32.7 mg, 0.123 mmol, 10.0 equiv) was dissolved in THF (2 mL). To this stirring solution was slowly added t-BuOK (6.9 mg, 0.0616 mmol, 5.0 equiv) at room temperature. The reaction mixture was stirred at room temperature for 2 minutes and quenched by the slow addition of H$_2$O (2 mL). The mixture was extracted with EA (3×3 mL) and the combined organic layers were dried over MgSO$_4$, filtered and concentrated under reduced pressure. Purification of the crude product by flash column chromatography (silica gel, hexanes/EtOAc=14:1) afforded 27 (2.9 mg, 54%) as a colorless oil.

Physical state: colorless oil
R$_f$=0.2 (Hex/EtOAc=14:1; anisaldehyde)
HRMS (m/z): calcd for C$_{28}$H$_{41}$O$_4$, [M+H]$^+$, 441.3005. found, 441.3010.
[α]$_D$=+67.2° (C=0.25, CH$_2$Cl$_2$)
$^1$H NMR (600 MHz, Chloroform-d) δ 5.99 (q, J=1.6 Hz, 1H), 5.71 (s, 1H), 4.92 (s, 1H), 4.06 (d, J=1.6 Hz, 1H), 2.49 (s, 1H), 2.43-2.28 (m, 3H), 2.19 (ddd, J=15.7, 7.9, 3.1 Hz, 1H), 2.09-1.98 (m, 2H), 1.81-1.72 (m, 1H), 1.76 (d, J=1.5 Hz, 3H), 1.64 (s, 3H), 1.62-1.48 (m, 2H), 1.46-1.22 (m, 6H), 1.20 (s, 3H), 1.12 (s, 3H), 1.04 (s, 3H), 0.96 (d, J=7.1 Hz, 3H), 0.91 (dd, J=11.8, 8.4 Hz, 1H), 0.68 (td, J=8.1, 6.2 Hz, 1H).
$^{13}$C NMR (151 MHz, Chloroform-d) δ 209.5, 178.9, 136.1, 134.1, 132.6, 123.8, 85.8, 81.0, 75.1, 48.0, 44.2, 43.8, 37.4, 35.8, 35.7, 31.6, 28.8, 25.8, 24.8, 23.8, 23.7, 23.6, 23.39, 23.35, 18.3, 15.72, 15.67.

Example 6

5-deoxyingenol 3-(1-methyl-cyclohexanecarboxylate) (Compound 6)

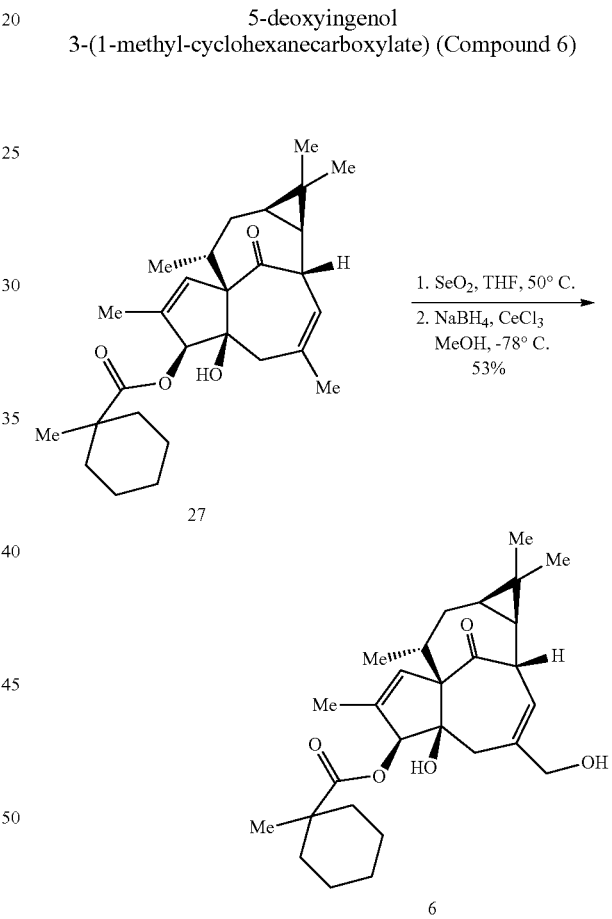

To a solution of 27 (2.0 mg, 0.0045 mmol, 1.0 equiv) in THF (1 mL) was added SeO$_2$ (2.5 mg, 0.023 mmol, 5.0 equiv) at room temperature. The flask was sealed with a plastic cap and the suspension was heated to 50° C. for 1 hour. After cooled to room temperature, the reaction mixture was filtered through a plug of silica gel (hexanes/EtOAc=1:1) to give a clear yellow solution, which was concentrated to yellow oil that was dissolved into MeOH (1 mL) at −78° C. The solution was added CeCl$_3$.7H$_2$O (8.5 mg, in 0.5 mL MeOH, 0.023 mmol, 5.0 equiv), immediately after the addition, the solid NaBH$_4$ (1.7 mg, 0.045 mmol, 10.0 equiv) was slow added to the flask. After 10 minutes at −78° C., H$_2$O (5 mL) was carefully added to quench this reaction which was diluted with Et$_2$O (5 mL). The mixture was extracted with Et$_2$O (3×5 mL) and the combined organic layers were dried over MgSO$_4$, filtered and concentrated under reduced pressure. Purification of the crude product by flash column chromatography (silica gel, hexanes/EtOAc=2:1) afforded 6 (1.1 mg, 53%) as a colorless oil.

Physical state: colorless oil
R$_f$=0.2 (Hex/EtOAc=2:1; anisaldehyde)
HRMS (m/z): calcd for C$_{28}$H$_{40}$NaO$_5$, [M+Na]$^+$, 479.2773. found, 479.2779.
[α]$_D$=+36.0° (c=0.05, CH$_2$Cl$_2$)
$^1$H NMR (600 MHz, Chloroform-d) δ 6.00 (q, J=2.4 Hz, 1H), 5.98 (d, J=1.7 Hz, 1H), 4.97 (s, 1H), 4.11 (d, J=11.7 Hz, 1H), 3.93 (s, 2H), 2.56 (d, J=17.1 Hz, 2H), 2.55 (s, 1H), 2.41 (td, J=6.8, 3.0 Hz, 1H), 2.37 (d, J=18.4 Hz, 1H), 2.18 (ddt, J=17.0, 12.5, 9.1 Hz, 1H), 2.07-2.00 (m, 2H), 1.82-1.77 (m, 1H), 1.76 (d, J=1.6 Hz, 3H), 1.62-1.56 (m, 2H), 1.44-1.27 (m, 6H), 1.20 (s, 3H), 1.12 (s, 3H), 1.05 (s, 3H), 0.96 (d, J=7.0 Hz, 3H), 0.96-0.93 (m, 1H), 0.71 (q, J=7.6 Hz, 1H).
$^{13}$C NMR (151 MHz, Chloroform-d) δ 209.2, 178.9, 137.7, 136.4, 132.3, 125.8, 85.8, 80.7, 75.1, 67.6, 44.2, 43.8, 43.4, 37.2, 35.8, 35.7, 31.7, 28.8, 25.8, 24.0, 23.6, 23.5, 23.4, 23.3, 18.5, 15.72, 15.70.

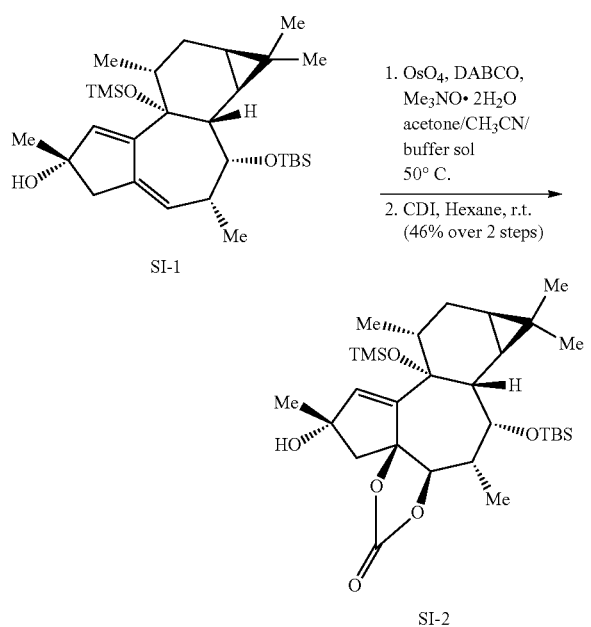

A 100 mL round flask was charged with SI-1 (661 mg, 1.31 mmol, 1.0 equiv), Me$_3$NO.2H$_2$O (1455 mg, 13.1 mmol, 10 equiv) and DABCO (160 mg, 1.31 mmol, 1.0 equiv) in Acetone/CH$_3$CN/*0.5 M buffer solution (26.2 mL, 0.05 M, 4:3:3). Then, OsO$_4$ solution (2.5 wt. % in tert-butanol, 0.65 mL, 0.0655 mmol, 0.05 equiv) was added to this flask and stir vigorously at 50° C. for 18 h, before being quenched by the addition of saturated aqueous Na$_2$SO$_3$ (20 mL). (*After 15 h, the reaction was monitored by TLC every 3 h. If S.M. stop to convert, we will quench the reaction to prevent side-product increase) The reaction mixture was extracted with ether (3×20 mL). The combined organic layers were washed with brine and dried over Na$_2$SO$_4$, filtered and concentrated in vacuo to afford crude diol (R$_f$=0.33 (Hex/EtOAc=7:3; anisaldehyde)). [*0.5 M buffer solution: pH=3, Na$_2$HPO$_4$ (280 mg) and citric acid (840 mg) was dissolved in H$_2$O (10 mL).]

The crude diol was dissolved in hexanes (26.2 mL, 0.05 M) and N,N-carbonyldiimidazole (1.05 g, 6.5 mmol, 5.0 equiv) was added. The solution was stirred at room temperature for 11 hours and quenched with water (20 mL). The aqueous layer was separated and extracted further with hexanes (2×30 mL). The combined organic layers were dried over Na$_2$SO$_4$, filtered and concentrated in vacuo to remove 80% solvent. Purification of the crude product by loading crude solution to flash column chromatography (silica gel, column packed in hexanes, then hexanes/EtOAc=20:1→9:1) afforded desired product SI-2 (342 mg, 46% over 2 steps) as a white foam.

Spectral data were identical to previously reported. (Jørgensen, L.; McKerrall, S. J.; Kuttruff, C. A.; Ungeheuer, F.; Felding J.; Baran, P. S. *Science* 2013, 341, 878-882)

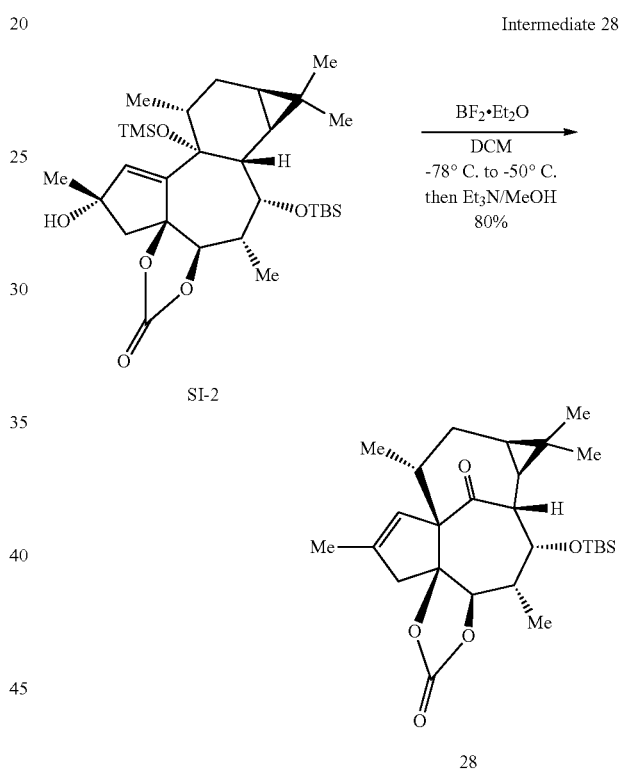

To a solution of SI-2 (191 mg, 0.338 mmol, 1.0 equiv) in CH$_2$Cl$_2$ (7 mL) was added BF$_3$.Et$_2$O (420 μL, 3.38 mmol, 10 equiv) dropwise at −78° C. The reaction mixture was stirred at this temperature for 2 min before being warmed to −50° C. After 30 min, a 1:1 mixture of Et$_3$N/MeOH (3 mL) was added at −40° C., the solution was stirred for 2 min and saturated aqueous NaHCO$_3$ (5 mL) was added. The reaction mixture was warmed to room temperature and extracted with CH$_2$Cl$_2$ (3×25 mL). The combined organic layers were dried over Na$_2$SO$_4$, filtered and concentrated under reduced pressure. Purification of the crude product by flash column chromatography (silica gel, column packed in CH$_2$Cl$_2$, then hexanes/EtOAc=20:1→10:1→5:1) afforded 28 (128 mg, 80%) as a white foam.

Spectral data were identical to previously reported (Jørgensen, L.; McKerrall, S. J.; Kuttruff, C. A.; Ungeheuer, F.; Felding J.; Baran, P. S. *Science* 2013, 341, 878-882)

Intermediate 29

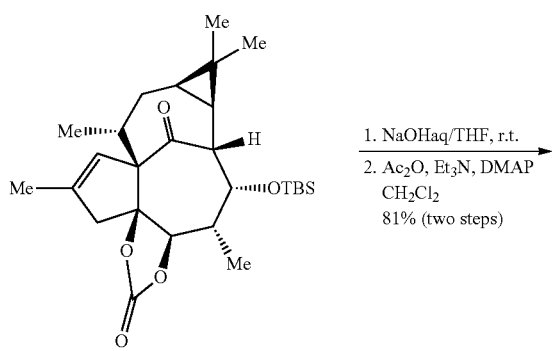

To a solution of 28 (590 mg, 1.24 mmol, 1 equiv) in THF (10 mL) was added 10% NaOH$_{(aq)}$ (10 mL). The reaction mixture was stirred vigorously at room temperature for 1 hour. The reaction mixture was extracted with Et$_2$O (3×20 mL) and the combined organic layers were dried over MgSO$_4$, filtered and concentrated under reduced pressure. The crude product was dissolved in CH$_2$Cl$_2$ (5 mL). To this solution was added Ac$_2$O (0.14 mL, 1.49 mmol, 1.2 equiv), Et$_3$N (0.26 mL, 1.86 mmol, 1.5 equiv) and DMAP (15.0 mg, 0.123 mmol, 0.1 equiv) at room temperature. The reaction mixture was stirred at room temperature for 2 hours before saturated NH$_4$Cl (10 mL) was added. The mixture was extracted with CH$_2$Cl$_2$ (3×10 mL) and the combined organic layers were dried over MgSO$_4$, filtered and concentrated under reduced pressure. Purification of the crude product by flash column chromatography (silica gel, hexanes/EtOAc=5:1) afforded 29 (490 mg, 81%) as a white solid.

Physical state: white solid
R$_f$=0.51 (Hex/EtOAc=7:3; anisaldehyde)
HRMS (m/z): calcd for C$_{28}$H$_{46}$NaO$_5$Si, [M+Na]$^+$, 513.3012. found, 513.3006.
[α]$_D$=+47.7° (c=0.7, CH$_2$Cl$_2$)
This compound is a rotamer (ratio=4:6)
$^1$H NMR (600 MHz, Chloroform-d) δ 5.64 (s, 1H), 5.04 (s, 0.4H), 4.90 (d, J=10.5 Hz, 0.6H), 3.89 (d, J=10.7 Hz, 0.4H), 3.85 (d, J=4.1 Hz, 1H), 3.19 (d, J=12.0 Hz, 0.4H), 3.01 (d, J=12.0 Hz, 0.6H), 2.90 (ddd, J=10.8, 7.0, 4.0 Hz, 0.4H), 2.58 (d, J=15.7 Hz, 0.4H), 2.52-2.39 (m, 1.6H), 2.39-2.31 (m, 0.6H), 2.29-2.20 (m, 1.4H), 2.17-2.12 (m, 0.6H), 2.11 (s, 1.2H), 2.09 (s, 1.8), 2.05 (brs, 0.6H), 1.72 (dq, J=15.4, 5.1, 4.5 Hz, 1H), 1.67 (s, 1.2H), 1.60 (s, 1.8H), 1.09 (s, 3H), 1.03 (s, 3H), 0.94 (s, 9H), 0.93-0.84 (m, 7H), 0.62 (dq, J=13.1, 6.7, 4.7 Hz, 1H), 0.17 (s, 1.2H), 0.16 (s, 1.8H), 0.06 (s, 1.2H), 0.04 (s, 1.8H).
$^{13}$C NMR (151 MHz, Chloroform-d) δ 207.2, 206.2, 174.1, 169.3, 136.0, 135.2, 125.8, 125.7, 86.7, 86.1, 85.6, 74.9, 73.8, 72.7, 72.1, 49.3, 48.8, 48.1, 46.6, 42.9, 40.5, 35.8, 35.5, 30.4, 28.71, 28.65, 26.22, 26.20, 24.9, 24.4, 24.2, 23.12, 23.05, 21.2, 20.7, 18.5, 17.4, 17.3, 17.2, 17.1, 16.5, 15.90, 15.85, 15.7, −3.50, −3.52, −4.5.

Intermediate 30

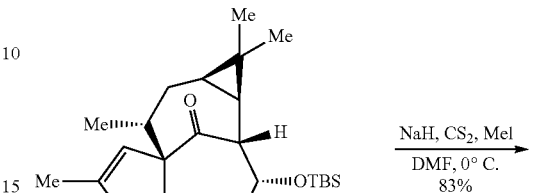

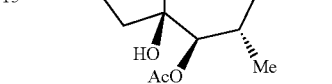

To a stirred solution of 29 (490 mg, 1.0 mmol, 1.0 equiv) in DMF (10 mL) was added NaH (60% in mineral oil, 80 mg, 2.0 mmol, 2.0 equiv) at 0° C. After stirring for 15 minutes, CS$_2$ (0.6 mL, 10.0 mmol, 10 equiv) was added to the suspension at same temperature. The reaction mixture was allowed warm up to room temperature and stirred for 40 minutes. Then MeI (0.62 mL, 10.0 mmol, 10 equiv) was added to the mixture. After stirring for 40 minutes at room temperature, the reaction mixture diluted with Et$_2$O (30 mL) and quenched with H$_2$O (30 mL). The mixture was extracted with Et$_2$O (3×30 mL) and the combined organic layers were dried over MgSO$_4$, filtered and concentrated under reduced pressure. Purification of the crude product by flash column chromatography (silica gel, hexanes/EtOAc=20:1) afforded 30 (483.4 mg, 83%) as a pale yellow foam.

Physical state: pale yellow foam
R$_f$=0.62 (Hex/EtOAc=8:2; anisaldehyde)
HRMS (m/z): calcd for C$_{30}$H$_{48}$NaO$_5$S$_2$Si, [M+Na]$^+$, 603.2610. found, 603.2606.
[α]$_D$=+91.3° (c=0.9, CH$_2$Cl$_2$)
$^1$H NMR (600 MHz, Chloroform-d) δ 5.70 (s, 1H), 5.10 (d, J=10.2 Hz, 1H), 3.86 (d, J=3.5 Hz, 1H), 3.17 (d, J=16.6 Hz, 1H), 2.93 (d, J=16.4 Hz, 1H), 2.86 (d, J=11.9 Hz, 1H), 2.55 (s, 3H), 2.39-2.18 (m, 3H), 2.06 (s, 3H), 1.85 (ddd, J=15.9, 5.9, 3.6 Hz, 1H), 1.20 (s, 3H), 1.06 (s, 3H), 0.99-0.94 (m, 1H), 0.96 (d, J=7.0 Hz, 3H), 0.94 (s, 9H), 0.83 (d, J=7.0 Hz, 3H), 0.72-0.65 (m, 1H), 0.16 (s, 3H), 0.02 (s, 3H).
$^{13}$C NMR (151 MHz, Chloroform-d) δ 212.6, 205.0, 169.0, 136.0, 124.7, 101.2, 77.2, 74.6, 72.0, 50.4, 43.7, 42.8, 36.2, 31.4, 28.7, 26.1, 25.4, 25.1, 22.8, 20.6, 20.5, 18.4, 17.3, 17.2, 16.2, 15.0, −3.5, −4.5.

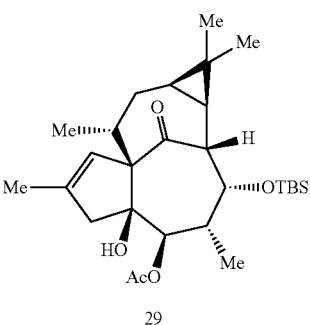

Intermediate 31

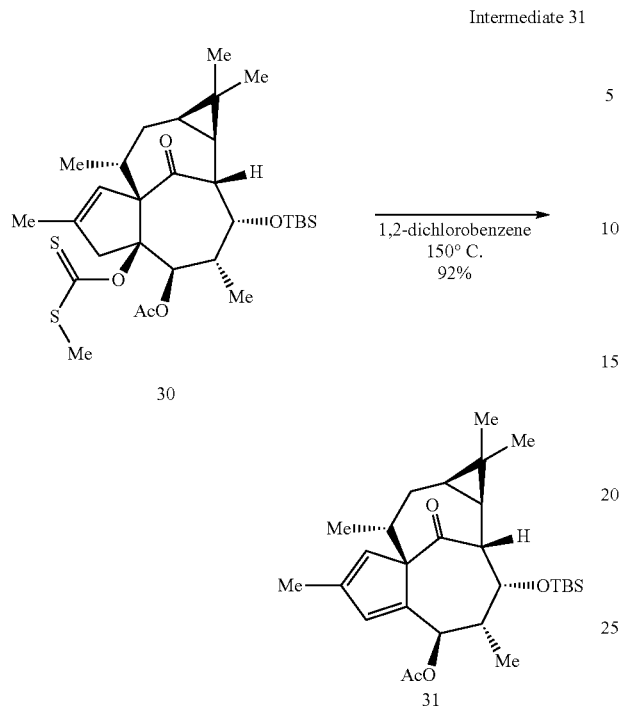
30

31

Compound 30 (483.4 mg, 0.83 mmol, 1.0 equiv) was dissolved in degassed 1,2-dichlorobenzene (15 mL) under an atmosphere of argon. The mixture was heat to 170° C. for 5 minutes. Upon cooling, the reaction mixture was passed through a short plug of silica gel, eluting with hexanes (to remove 1,2-dichlorobenzene), followed by 20:1 hexanes: EtOAc to afford 31 (365.9 mg, 92%) as a yellow foam.

Physical state: pale yellow foam
$R_f$=0.55 (Hex/EtOAc=8:2; anisaldehyde)
HRMS (m/z): calcd for $C_{28}H_{44}NaO_4Si$, $[M+Na]^+$, 495.2907. found, 495.2904.
$[\alpha]_D$=+3.6° (c=0.89, $CH_2Cl_2$)
$^1H$ NMR (600 MHz, Chloroform-d) δ 6.22 (d, J=1.4 Hz, 1H), 6.09 (s, 1H), 5.87 (d, J=5.3 Hz, 1H), 4.17 (dd, J=8.3, 3.8 Hz, 1H), 3.87 (dd, J=11.3, 3.9 Hz, 1H), 2.94 (h, J=7.0 Hz, 1H), 2.70-2.59 (m, 1H), 2.06 (s, 3H), 2.03 (dt, J=5.2, 2.9 Hz, 2H), 1.90 (d, J=1.4 Hz, 3H), 1.26 (s, 3H), 1.16 (dd, J=11.3, 9.3 Hz, 1H), 1.04 (s, 3H), 0.92 (s, 9H), 0.75 (dt, J=8.4, 3.9 Hz, 1H), 0.64 (d, J=7.6 Hz, 3H), 0.61 (d, J=6.7 Hz, 3H), 0.08 (s, 3H), 0.03 (s, 3H).
$^{13}C$ NMR (151 MHz, Chloroform-d) δ 207.5, 169.6, 141.4, 141.0, 138.3, 133.7, 82.9, 79.4, 69.5, 45.9, 40.8, 37.3, 33.0, 29.0, 25.9, 24.8, 24.1, 21.5, 21.2, 18.4, 18.3, 15.4, 15.1, 12.8, −4.6, −4.7.

Intermediate 32

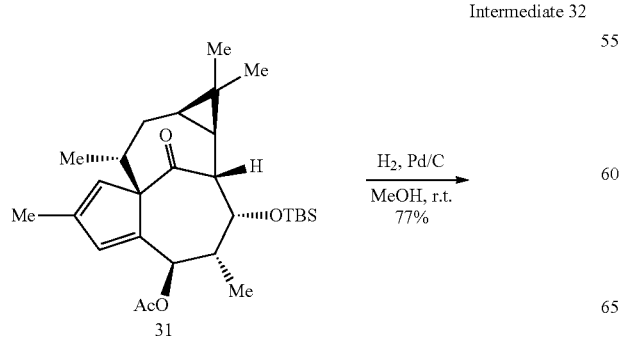
31

32

To a solution of 31 (365.9 mg, 0.77 mmol, 1.0 equiv) in MeOH (10 mL) was added 10% Pd on carbon (82 mg, 0.077 mmol, 0.1 equiv). Through the stirring mixture was bubbled $H_2$ for 20 seconds at room temperature. Then the solvent was concentrated under reduced pressure. Purification of the crude product by flash column chromatography (silica gel, hexanes/EtOAc=80:1→50:1) afforded 32 (282.7 mg, 77%) as a colorless oil.

Physical state: colorless oil
$R_f$=0.5 (Hex/EtOAc=10:1; anisaldehyde)
HRMS (m/z): calcd for $C_{28}H_{46}NaO_4Si$, $[M+Na]^+$, 497.3063. found, 497.3072.
$[\alpha]_D$=+25.8° (c=0.12, $CH_2Cl_2$)
$^1H$ NMR (600 MHz, Chloroform-d) δ 5.66 (s, 1H), 4.70 (s, 1H), 3.88 (d, J=4.3 Hz, 1H), 2.61 (d, J=12.1 Hz, 1H), 2.56-2.44 (m, 2H), 2.05 (s, 3H), 2.04-1.97 (m, 2H), 1.89 (d, J=16.2 Hz, 1H), 1.83 (dt, J=15.7, 5.5 Hz, 1H), 1.68 (ddd, J=14.8, 10.2, 5.5 Hz, 1H), 1.65 (s, 3H), 1.10 (s, 3H), 1.04 (s, 3H), 0.94 (s, 9H), 0.95-0.91 (m, 1H), 0.90 (d, J=7.0 Hz, 3H), 0.88 (d, J=6.9 Hz, 3H), 0.68 (td, J=8.9, 6.1 Hz, 1H), 0.16 (s, 3H), 0.04 (s, 3H).
$^{13}C$ NMR (151 MHz, Chloroform-d) δ 205.6, 169.0, 138.4, 124.2, 74.5, 73.8, 71.5, 51.0, 50.9, 49.2, 37.9, 36.9, 29.6, 28.1, 25.6, 23.7, 23.2, 22.8, 20.3, 17.8, 16.4, 15.6, 15.3, 15.2, −4.2, −5.2.

Intermediate 33

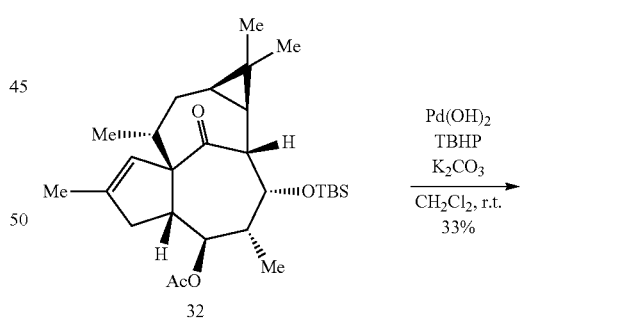
32

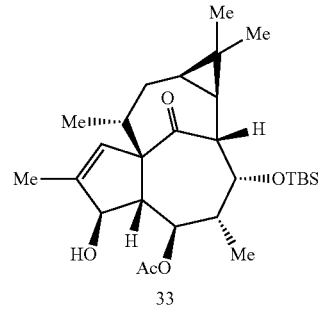
33

To a solution of 32 (282.7 mg, 0.60 mmol, 1.0 equiv) in CH$_2$Cl$_2$ (8 mL) was added 20% Pd(OH)$_2$ on carbon (15.9 mg, 0.03 mmol, 0.05 equiv) and K$_2$CO$_3$ (20.7 mg, 0.15 mmol, 0.25 equiv) at room temperature. The mixture was cooled to 4° C., and TBHP (5.5 M in decane, 0.54 mL, 3.0 mmol, 5.0 equiv) was added with vigorous stirring. Then the reaction mixture was allowed to warm up to room temperature. After 24 hours, the reaction mixture was filtered through a plug of silica gel (washed with CH$_2$Cl$_2$). The solvent was removed under reduced pressure. Purification of the crude product by flash column chromatography (silica gel, hexanes/EtOAc=3:1) afforded 33 (95 mg, 33%) as a colorless crystal.

Physical state: colorless crystal

R$_f$=0.1 (Hex/EtOAc=3:1; anisaldehyde)

HRMS (m/z): calcd for C$_{28}$H$_{46}$NaO$_5$Si, [M+Na]$^+$, 513.3012. found, 513.3018.

[α]$_D$=+32.9° (c=0.14, CH$_2$Cl$_2$)

$^1$H NMR (600 MHz, Chloroform-d) δ 5.89 (s, 1H), 4.71 (brs, 1H), 4.21 (s, 1H), 3.91 (d, J=3.9 Hz, 1H), 2.69 (d, J=11.7 Hz, 1H), 2.38 (s, 1H), 2.25-2.12 (m, 2H), 2.08 (s, 3H), 1.82 (dt, J=15.8, 6.1 Hz, 1H), 1.79-1.73 (m, 1H), 1.76 (d, J=1.1 Hz, 3H), 1.13 (s, 3H), 1.04 (s, 3H), 0.95-0.91 (m, 1H), 0.933 (s, 9H), 0.926 (d, J=5.4 Hz, 3H), 0.86 (d, J=7.1 Hz, 3H), 0.72-0.66 (m, 1H), 0.14 (s, 3H), 0.04 (s, 3H).

$^{13}$C NMR (151 MHz, Chloroform-d) δ 205.5, 169.3, 139.8, 129.7, 82.1, 75.8, 72.4, 70.9, 59.7, 50.4, 47.8, 42.5, 29.9, 28.1, 25.5, 23.5, 22.9, 22.8, 20.4, 17.8, 15.7, 15.0, 14.5, 14.0, −4.4, −5.2.

by the slow addition of H$_2$O (2 mL). The mixture was extracted with EtOAc (3×3 mL) and the combined organic layers were dried over MgSO$_4$, filtered and concentrated under reduced pressure. Purification of the crude product by flash column chromatography (silica gel, hexanes/EtOAc=20:1) afforded 34 (9.7 mg, 76%) as a colorless oil.

Physical state: colorless oil

R$_f$=0.17 (Hex/EtOAc=20:1; anisaldehyde)

HRMS (m/z): calcd for C$_{36}$H$_{58}$NaO$_6$Si, [M+Na]$^+$, 637.3900. found, 637.3893.

[α]$_D$=+100.0° (c=0.17, CH$_2$Cl$_2$)

$^1$H NMR (600 MHz, Chloroform-d) δ 6.03 (s, 1H), 5.37 (s, 1H), 4.64 (brs, 1H), 3.87 (d, J=4.1 Hz, 1H), 2.58 (d, J=11.9 Hz, 1H), 2.36 (s, 1H), 2.26-2.18 (m, 1H), 2.17-2.07 (m, 1H), 2.13 (s, 3H), 2.03-1.95 (m, 2H), 1.81 (dt, J=15.8, 6.0 Hz, 1H), 1.70-1.63 (m, 1H), 1.66 (d, J=1.2 Hz, 3H), 1.59-1.50 (m, 2H), 1.40-1.17 (m, 6H), 1.13 (s, 3H), 1.10 (s, 3H), 1.04 (s, 3H), 0.96-0.92 (m, 1H), 0.94 (d, J=7.2 Hz, 3H), 0.93 (s, 9H), 0.89 (d, J=6.9 Hz, 3H), 0.68 (td, J=8.5, 6.4 Hz, 1H), 0.15 (s, 3H), 0.04 (s, 3H).

$^{13}$C NMR (151 MHz, Chloroform-d) δ 205.2, 177.3, 170.0, 137.6, 132.8, 82.1, 74.3, 73.1, 71.9, 57.4, 51.6, 49.6, 43.3, 41.9, 35.7, 30.2, 28.7, 26.7, 26.1, 25.8, 24.3, 23.6, 23.4, 20.9, 18.4, 16.1, 15.8, 15.7, 14.9, −3.6, −4.5.

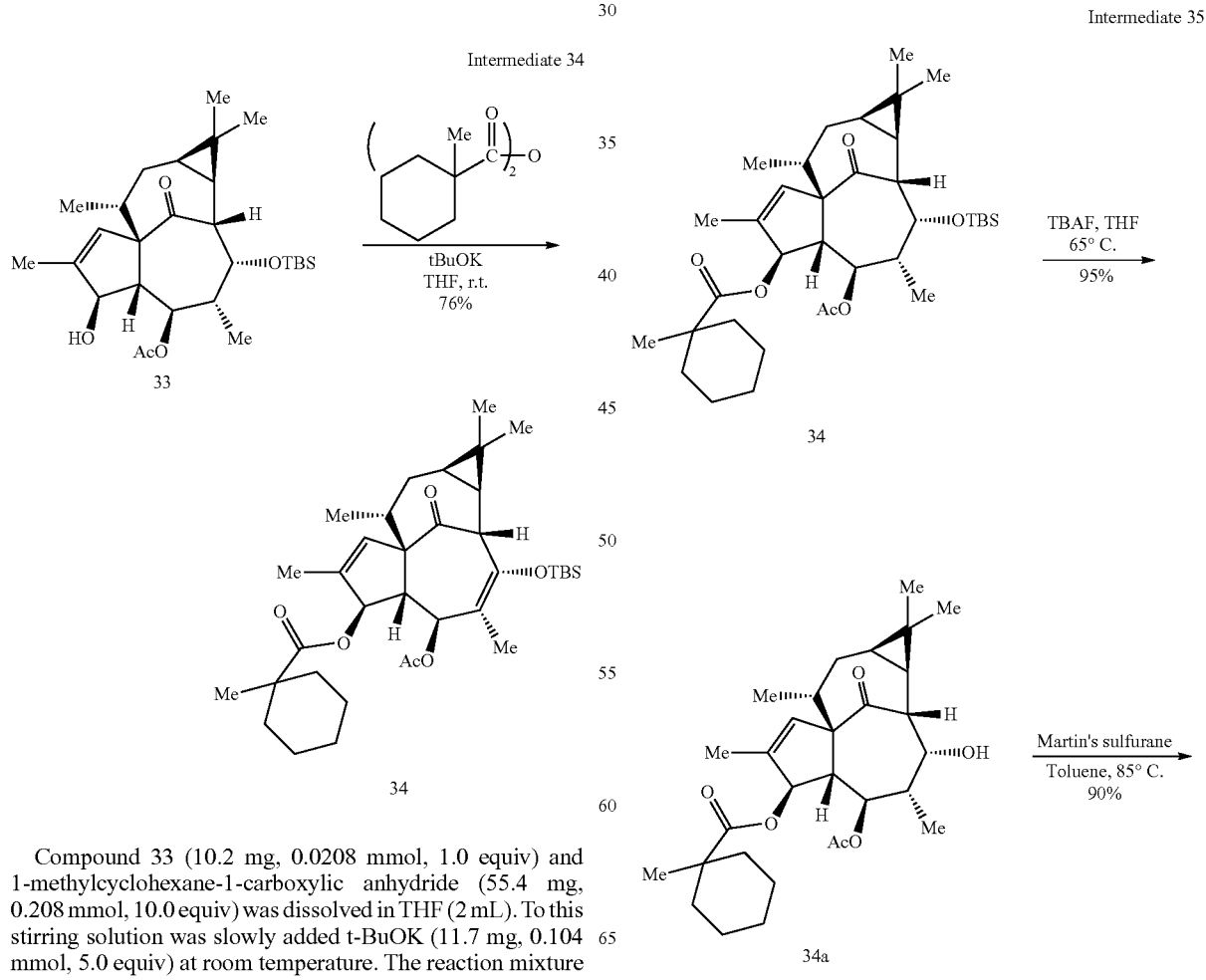

Compound 33 (10.2 mg, 0.0208 mmol, 1.0 equiv) and 1-methylcyclohexane-1-carboxylic anhydride (55.4 mg, 0.208 mmol, 10.0 equiv) was dissolved in THF (2 mL). To this stirring solution was slowly added t-BuOK (11.7 mg, 0.104 mmol, 5.0 equiv) at room temperature. The reaction mixture was stirred at room temperature for 2 minutes and quenched

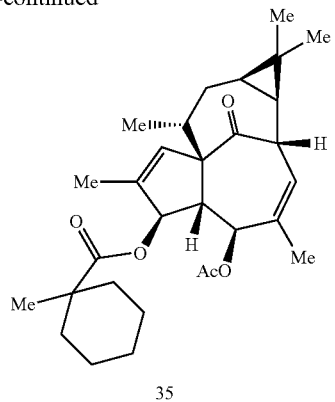

35

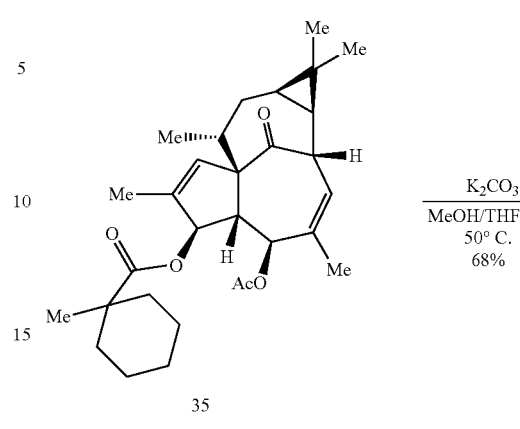

K$_2$CO$_3$
―――――→
MeOH/THF 4:1
50° C.
68%

35

To a solution of 34 (6.6 mg, 0.0107 mmol, 1.0 equiv) in THF (1 mL) was added TBAF (1 M, 0.11 mL, 0.107 mmol, 10.0 equiv) and H$_2$O (2 µL, 0.107 mmol, 10.0 equiv) at room temperature. The flask was sealed with a plastic cap and the reaction mixture was heated to 65° C. After 10 hours, the reaction mixture was cooled to room temperature then water (3 mL) was added. The mixture was extracted with Et$_2$O (5×3 mL) and the combined organic layers were dried over MgSO$_4$, filtered and concentrated under reduced pressure. Purification of the crude product by flash column chromatography (silica gel, hexanes/EtOAc=5:1) afforded 35a (5.1 mg, 95%).

To a solution of 34a (5.1 mg, 0.0102 mmol, 1.0 equiv) in toluene (2 mL) was added Martin's sulfurane (8.9 mg, 0.0132 mmol, 1.3 equiv) at room temperature. The solution was heated to 85° C. for 10 minutes. Then toluene was removed under reduced pressure. Purification of the crude product by flash column chromatography (silica gel, hexanes/EtOAc=20:1) afforded 35 (4.4 mg, 90%).

Physical state: colorless oil

R$_f$=0.3 (Hex/EtOAc=10:1; anisaldehyde)

HRMS (m/z): calcd for C$_{30}$H$_{42}$NaO$_5$, [M+Na]$^+$, 505.2930. found, 505.2932.

[α]$_D$=−21.9° (c=0.27, CH$_2$Cl$_2$)

$^1$H NMR (600 MHz, Chloroform-d) δ 6.01 (s, 1H), 5.80 (d, J=5.7 Hz, 1H), 5.24 (s, 1H), 4.86 (brs, 1H), 3.73 (dd, J=11.4, 5.2 Hz, 1H), 2.82 (s, 1H), 2.32-2.24 (m, 1H), 2.18 (s, 3H), 2.00 (d, J=12.7 Hz, 2H), 1.83 (dt, J=15.8, 5.9 Hz, 1H), 1.77-1.71 (m, 1H), 1.74 (s, 3H), 1.62 (s, 3H), 1.60-1.50 (m, 2H), 1.39-1.16 (m, 6H), 1.141 (s, 3H), 1.138 (s, 3H), 1.05 (s, 3H), 0.99 (d, J=7.0 Hz, 3H), 0.94 (dd, J=11.8, 8.5 Hz, 1H), 0.70 (td, J=8.4, 6.6 Hz, 1H).

$^{13}$C NMR (151 MHz, Chloroform-d) δ 206.0, 177.1, 171.0, 138.7, 136.2, 131.0, 125.5, 81.6, 71.8, 55.9, 44.7, 43.4, 41.5, 35.7, 30.4, 28.7, 26.7, 25.8, 23.8, 23.5, 23.4, 22.8, 21.7, 21.3, 15.7, 15.5, 15.1.

Intermediate 36

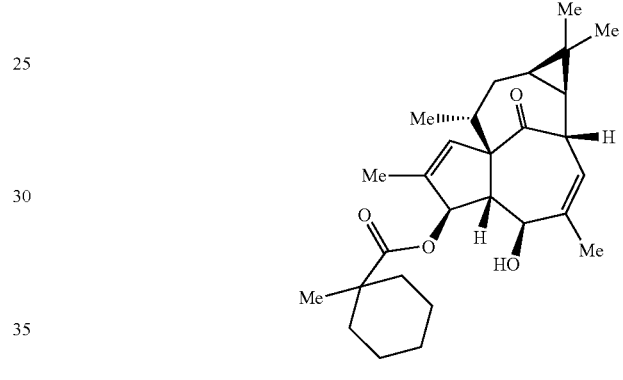

36

To a solution of 35 (4.2 mg, 0.0087 mmol, 1.0 equiv) in MeOH (0.8 mL) and THF (0.2 mL) was added K$_2$CO$_3$ (6.0 mg, 0.0435 mmol, 5.0 equiv) at room temperature. The reaction mixture was stirred for 2 hours at 50° C. before quenched with saturated NH$_4$Cl$_{(aq)}$ (2 mL). The mixture was extracted with Et$_2$O (5×3 mL) and the combined organic layers were dried over MgSO$_4$, filtered and concentrated under reduced pressure. Purification of the crude product by flash column chromatography (silica gel, hexanes/EtOAc=5:1) afforded 36 (2.6 mg, 68%).

Physical state: white foam

R$_f$=0.25 (Hex/EtOAc=7:1; anisaldehyde)

HRMS (m/z): calcd for C$_{28}$H$_{40}$NaO$_4$, [M+Na]$^+$, 463.2824. found, 463.2825.

[α]$_D$=+10.0° (c=0.21, CH$_2$Cl$_2$)

$^1$H NMR (600 MHz, Chloroform-d) δ 6.12 (s, 1H), 5.67 (d, J=5.3 Hz, 1H), 5.20 (s, 1H), 3.83 (s, 1H), 3.72 (d, J=9.9 Hz, 1H), 3.49 (dd, J=11.6, 4.7 Hz, 1H), 2.52 (d, J=10.0 Hz, 1H), 2.09 (ddd, J=7.1, 4.6, 2.8 Hz, 1H), 2.06-1.97 (m, 2H), 1.84-1.80 (m, 1H), 1.80 (d, J=1.1 Hz, 3H), 1.77 (s, 3H), 1.66 (ddd, J=15.6, 9.0, 2.4 Hz, 1H), 1.60-1.51 (m, 2H), 1.42-1.20 (m, 6H), 1.16 (s, 3H), 1.08 (s, 3H), 1.04 (s, 3H), 1.00 (d, J=7.0 Hz, 3H), 0.89 (dd, J=11.9, 8.4 Hz, 1H), 0.69 (td, J=8.7, 6.4 Hz, 1H).

13C NMR (151 MHz, Chloroform-d) δ 205.7, 179.6, 139.4, 137.2, 132.6, 122.1, 85.6, 76.0, 72.2, 59.0, 44.9, 43.5, 42.8, 35.6, 35.5, 30.2, 28.7, 25.8, 23.7, 23.42, 23.36, 23.1, 22.7, 21.8, 15.9, 15.6, 15.2.

Example 7

4-deoxyingenol 3-(1-methyl-cyclohexanecarboxylate) (Compound 7)

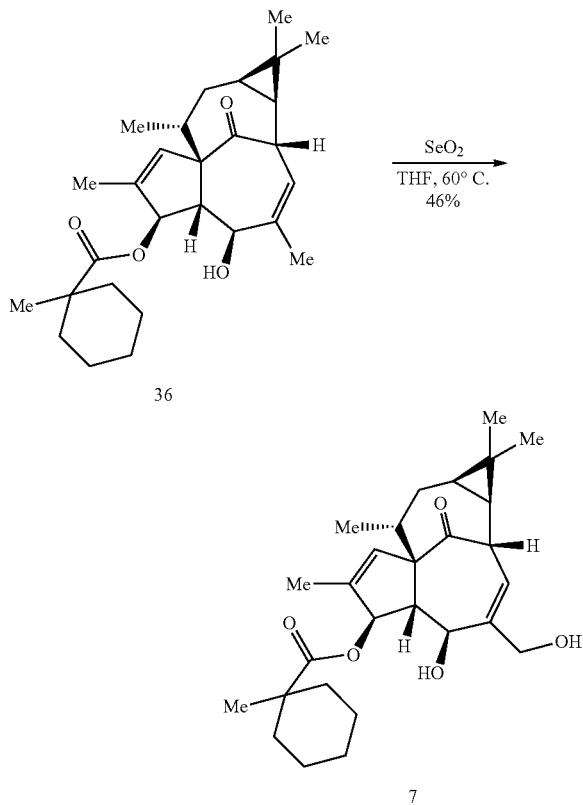

To a solution of 36 (2.5 mg, 0.0057 mmol, 1.0 equiv) in THF (1 mL) was added SeO$_2$ (1.9 mg, 0.0171 mmol, 3.0 equiv) at room temperature. The flask was sealed with a plastic cap and the suspension was heated to 60° C. for 1 hour. The mixture was cooled to room temperature, then H$_2$O (2 mL) was added. The mixture was extracted with Et$_2$O (5×3 mL) and the combined organic layers were dried over MgSO$_4$, filtered and concentrated under reduced pressure. Purification of the crude product by flash column chromatography (silica gel, hexanes/EtOAc=2:1) afforded 7 (1.2 mg, 46%) as a white foam.

Physical state: white foam
R$_f$=0.15 (Hex/EtOAc=2:1; anisaldehyde)
HRMS (m/z): calcd for C$_{28}$H$_{40}$NaO$_5$, [M+Na]$^+$, 479.2773. found, 479.2767.
[α]$_D$=+8.0° (c=0.1, CH$_2$Cl$_2$)
$^1$H NMR (600 MHz, Chloroform-d) δ 6.09 (d, J=1.2 Hz, 1H), 5.98 (d, J=4.5 Hz, 1H), 5.21 (s, 1H), 4.13 (d, J=12.2 Hz, 1H), 4.05 (d, J=12.3 Hz, 1H), 4.04 (d, J=10.8 Hz, 1H), 3.55 (dd, J=11.9, 5.1 Hz, 1H), 2.55 (d, J=10.2 Hz, 1H), 2.14-2.07 (m, 1H), 2.07-1.96 (m, 2H), 1.84 (dt, J=15.8, 5.9 Hz, 1H), 1.81 (d, J=1.3 Hz, 3H), 1.69 (ddd, J=15.9, 8.5, 2.4 Hz, 1H), 1.64-1.49 (m, 2H), 1.41-1.22 (m, 6H), 1.17 (s, 3H), 1.10 (s, 3H), 1.05 (s, 3H), 1.00 (d, J=7.0 Hz, 3H), 0.94 (dd, J=11.9, 8.4 Hz, 1H), 0.72 (td, J=8.5, 6.3 Hz, 1H).
$^{13}$C NMR (151 MHz, Chloroform-d) δ 205.5, 180.0, 141.6, 137.3, 132.3, 125.9, 85.3, 75.6, 72.2, 67.2, 58.7, 45.0, 43.6, 42.8, 35.5, 35.5, 30.4, 28.7, 25.7, 23.7, 23.4, 22.6, 16.2, 15.7, 15.1.

Intermediate SI-4

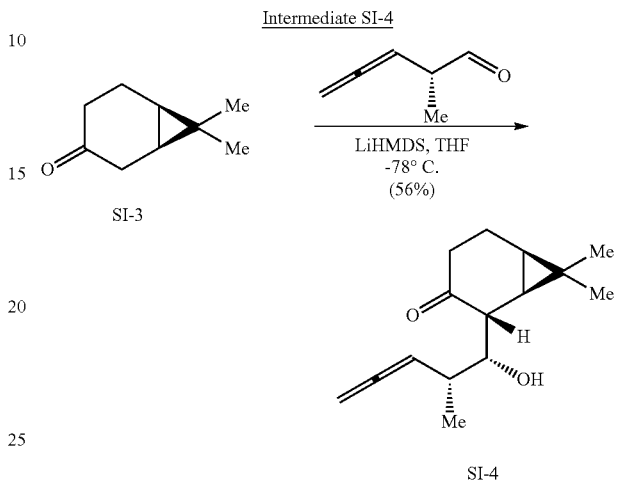

In a 3 L round-bottomed flask, chiral alcohol (92 g, 941 mmol, 2.0 equiv) was dissolved in THF (1720 mL) to give a colorless solution. IBX (395 g, 1411 mmol, 3.0 equiv) was added and the resulting suspension was heated to 80° C. for 2 h (until TLC indicated complete consumption of starting material). The mixture was cooled to room temperature, filtered over sintered funnel and the filter residue was washed with THF (573 mL). The filtrate (aldehyde in THF) was kept under argon atmosphere and dried over sodium sulfate 30 min prior to use for the aldol reaction.

In a another 3 L round-bottomed flask was ketone (Paquette, L. A.; Ross R. J.; Shi, Y. J. Org. Chem. 1990, 55, 1589-1598) (65 g, 471 mmol, 1.0 equiv) in THF (143 mL) under argon and the solution was cooled to –78° C. LiHMDS (1M in THF, 847 mL, 847 mmol, 1.8 equiv) was added drop wise under argon at –78° C. and the solution was stirred at –78° C. for 1 h. Above solution of aldehyde in THF was added drop wise over 50 minutes under argon at –78° C. The mixture was stirred at –78° C. for 2 h then quenched by the addition of saturated aqueous NH$_4$Cl (6 vol. of starting material). Aqueous layer was separated and the aqueous layer was extracted with ethyl acetate (3× (12 vol. of starting material)). The combined organic fractions were dried with sodium sulfate, evaporated under vacuum at 45° C. Purification of the crude product by flash column chromatography afforded SI-4 (68 g, 56%) as a colorless oil.

Physical state: colorless oil
R$_f$=0.26 (Hex/EtOAc=9:1; anisaldehyde)
HRMS (m/z): calc. for C$_{15}$H$_{22}$O$_2$ [M+H]$^+$=235.1698. found, 235.1697.
[α]$_D$=+207.6° (c=1.40, CH$_2$Cl$_2$)
$^1$H NMR (600 MHz, CDCl$_3$) δ 5.24 (p, J=6.9 Hz, 1H), 4.69 (dt, J=6.4, 3.0 Hz, 2H), 3.96-3.91 (m, 2H), 2.40-2.09 (m, 3H), 1.96 (t, J=8.4 Hz, 1H), 1.85 (ddd, J=14.9, 7.7, 2.2 Hz, 1H), 1.66-1.61 (m, 1H), 1.21 (d, J=7.4 Hz, 3H), 1.15 (s, 3H), 1.11 (s, 3H), 0.92 (td, J=9.1, 7.7 Hz, 1H), 0.41 (t, J=8.3 Hz, 1H).
$^{13}$C NMR (151 MHz, CDCl$_3$) δ 219.9, 209.1, 86.5, 74.7, 71.8, 50.2, 41.3, 32.9, 27.9, 25.5, 23.3, 20.7, 19.7, 17.4, 14.9.

Intermediate SI-6

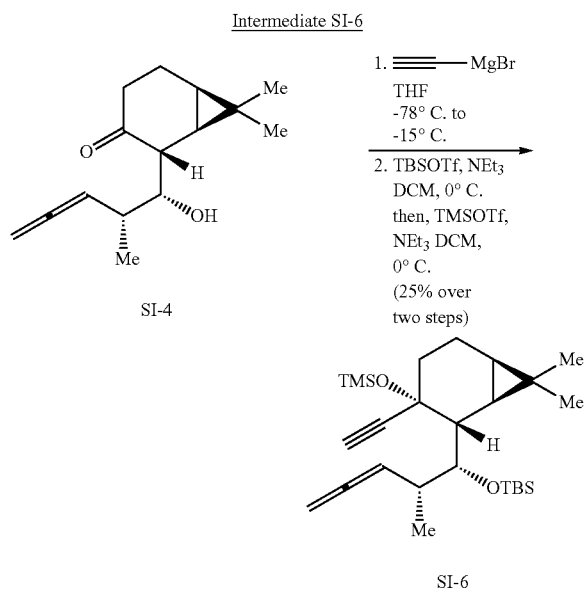

In a 2 L round-bottomed flask, ethynylmagnesium bromide (0.5M in THF, 2321 mL, 1161 mmol, 4.0 equiv) was cooled to −78° C. SI-4 (68 g, 290 mmol, 1.0 equiv) in THF (288 mL) was added over 35 min at −78° C. The reaction mixture was stirred at this temperature for 10 min, warmed to −15° C. and stirring was continued for 4 h. Saturated aqueous NH$_4$Cl was added, THF layer separated and distilled completely. The aqueous layer was extracted with EtOAc and the combined organic layers were filter through bed of silica gel and dried over Na$_2$SO$_4$, concentrated under vacuum to give crude dsmehtyl ethynyl pdt SI-5 (77 g).

To a solution of crude SI-5 in DCM (568 mL) was added distilled triethylamine (165 ml, 1183 mmol, 4.0 equiv) and then TBSOTf (136 ml, 591 mmol, 2.0 equiv) was added drop wise at 0° C. After 1.5 h, the starting material was judged as consumed by TLC. Then, distilled triethylamine (165 mL, 1183 mmol, 4.0 equiv) and TMSOTf (108 mL, 591 mmol, 2.0 equiv) were added drop wise at 0° C. and stirred for further 1.5 h. Then the reaction was quenched with saturated aqueous NaHCO$_3$ (500 mL) and was diluted with DCM (500 mL). After aqueous layer separated, DCM layer was washed with saturated aqueous NaHCO$_3$ (500 mL) again and 500 mL water (×3) (to remove triethylamine). All aqueous layers extracted with 700 mL (×3) ethyl acetate. Combined organic layers were dried over Na$_2$SO$_4$, filtered and concentrated under reduced pressure. Purification of the crude product by flash column chromatography afforded SI-6 (33 g, 25%) as a colorless oil.

Spectroscopic data for SI-5:
Physical state: colorless oil
$R_f$=0.19 (Hex/EtOAc=4:1; anisaldehyde)
HRMS (m/z): calc. for C$_{17}$H$_{24}$O$_2$ [M+H]$^+$=261.1855. found, 261.1856.
$[\alpha]_D$=−27.8° (c=0.80, CH$_2$Cl$_2$)
$^1$H NMR (600 MHz, CDCl$_3$) δ 5.54-5.02 (m, 1H), 4.73 (dt, J=6.3, 2.9 Hz, 2H), 4.16-4.13 (m, 1H), 3.09 (s, 1H), 2.68 (s, 1H), 2.64-2.51 (m, 3H), 1.70 (dd, J=14.9, 7.0 Hz, 1H), 1.59-1.47 (m, 2H), 1.35-1.28 (m, 1H), 1.08 (d, J=6.6 Hz, 3H), 1.06 (s, 3H), 0.96 (s, 3H), 0.73 (t, J=8.8 Hz, 1H), 0.38 (dd, J=9.4, 5.2 Hz, 1H).
$^{13}$C NMR (151 MHz, CDCl$_3$) δ 209.3, 87.6, 86.6, 76.1, 75.1, 74.8, 67.0, 46.2, 38.9, 34.8, 28.8, 24.2, 21.6, 19.9, 17.6, 16.8, 15.4.

Spectroscopic data for SI-6:
Physical state: colorless oil
$R_f$=0.66 (Hex; anisaldehyde)
HRMS (m/z): calc. for C$_{26}$H$_{46}$O$_2$Si$_2$ [M+Na]$^+$=469.2934. found, 469.2943.
$[\alpha]_D$=+25.8° (c=0.58, CH$_2$Cl$_2$)
$^1$H NMR (600 MHz, CDCl$_3$) δ 5.49 (q, J=7.0 Hz, 1H), 4.60-4.58 (m, 2H), 4.36 (dd, J=4.0, 1.4 Hz, 1H), 3.04-3.00 (m, 1H), 2.51 (s, 1H), 1.88-1.79 (m, 2H), 1.50-1.42 (m, 1H), 1.38 (dd, J=5.6, 3.8 Hz, 1H), 1.33-1.23 (m, 1H), 1.15-1.08 (m, 4H), 1.00 (s, 3H), 0.92 (s, 9H), 0.88 (s, 3H), 0.60-0.49 (m, 1H), 0.18 (s, 9H), 0.07 (s, 3H), 0.04 (s, 3H).
$^{13}$C NMR (151 MHz, CDCl$_3$) δ 208.4, 93.5, 88.1, 76.4, 74.1, 73.5, 68.4, 49.2, 38.6, 35.6, 29.1, 26.0, 21.2, 18.5, 18.1, 18.1, 16.8, 15.8, 15.0, 1.7, −3.8, −4.6.

Intermediate 2'

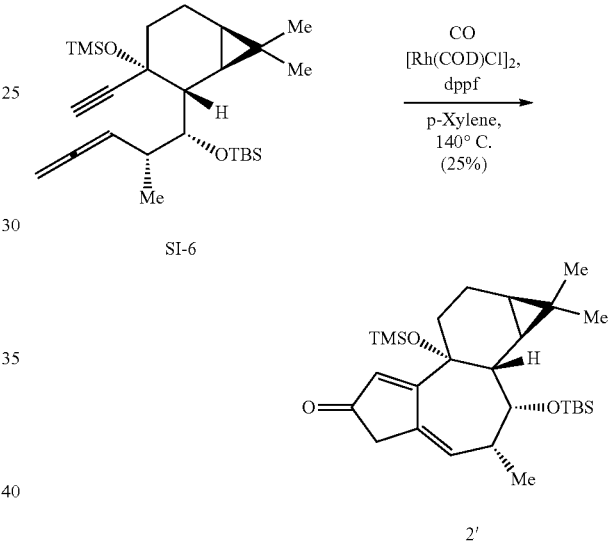

In a round-bottomed flask was SI-6 (20 g, 44.8 mmol, 1.0 equiv) in anhydrous p-Xylene (4454 ml), the solution was degassed using carbon monoxide for 5 h. 1, 5-Cyclooctadienerhodium(I) chloride dimer (2.208 g, 4.48 mmol, 0.1 equiv) and dppf (4.89 g, 8.95 mmol, 0.2 equiv) were added and the reaction mixture was transferred into a preheated oil bath and stirred at 140° C. under 1 atm of CO for 18 h. The reaction mixture was cooled to room temperature and concentrated under reduced pressure. Purification of the crude product by flash column chromatography afforded 2' (5.3 g, 25%) as a yellow solid.

Physical state: yellow solid (m.p. 101-104° C.)
$R_f$=0.38 (Hex/EtOAc=10:1; anisaldehyde)
HRMS (m/z): calc. for C$_{27}$H$_{46}$O$_3$Si$_2$ [M+H]$^+$=475.3064. found, 475.3065.
$[\alpha]_D$=−118.6° (c=0.86, CH$_2$Cl$_2$)
$^1$H NMR (600 MHz, CDCl$_3$) δ 6.06 (d, J=1.6 Hz, 1H), 5.88 (d, J=8.8 Hz, 1H), 4.12 (dd, J=8.3, 3.1 Hz, 1H), 3.17-2.95 (ABq, J=19.9, 2H), 2.59-2.53 (m, 1H), 2.08-1.84 (m, 2H), 1.71-1.53 (m, 2H), 1.42 (d, J=7.4 Hz, 3H), 1.35-1.20 (m, 2H), 1.08 (s, 3H), 0.91 (s, 9H), 0.86 (s, 3H), 0.66 (td, J=9.1, 1.5 Hz, 1H) 0.01 (s, 15H).

$^{13}$C NMR (151 MHz, CDCl$_3$) δ 205.3, 176.9, 134.8, 133.3, 129.9, 73.5, 73.3, 48.2, 45.0, 43.8, 35.7, 28.4, 25.9, 22.6, 18.5, 17.9, 17.7, 16.4, 15.3, 12.6, 2.0, −4.2, −5.1.

Intermediate 37

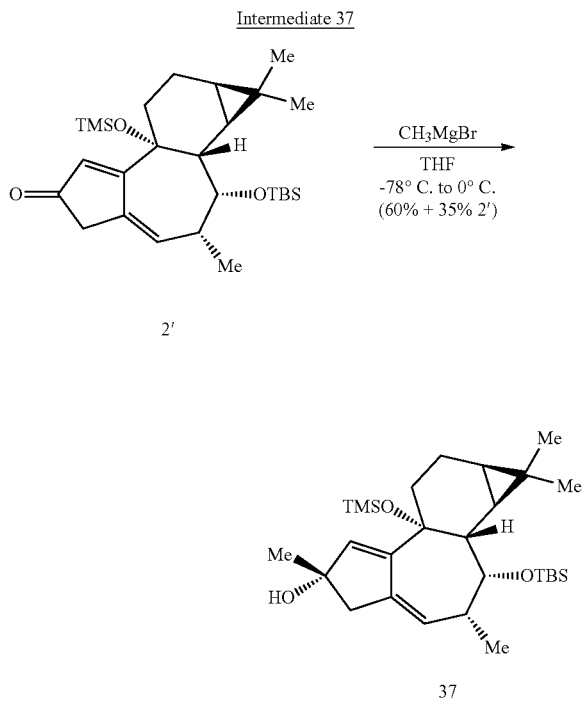

To a solution of 2' (602 mg, 1.27 mmol, 1.0 equiv) in THF (64 mL, 0.02 M) was added methyl magnesium bromide (3.0 M in Et$_2$O, 2.5 mL, 7.62 mmol, 6.0 equiv) over 5 min at −78° C. The reaction mixture was stirred at this temperature for 5 min before being warmed to 0° C. After 15 min, the reaction mixture was cooled back to −78° C. and carefully quenched with NH$_4$Cl$_{(aq)}$ (30 mL). The mixture was extracted with EtOAc (3×50 mL) and the combined organic layers were dried over Na$_2$SO$_4$, filtered and concentrated under reduced pressure. Purification of the crude product by flash column chromatography (silica gel, hexanes/EtOAc=20:1→4:1) afforded 37 (373 mg, 60%) as a colorless foam and recovered 2' (212 mg, 35%).

Physical state: colorless foam

R$_f$=0.50 (Hex/EtOAc=4:1; anisaldehyde)

HRMS (m/z): calc. for C$_{28}$H$_{50}$O$_3$Si$_2$ [M+H]$^+$=461.2718. found, 461.2722.

[α]$_D$=−131.3° (c=0.75, CH$_2$Cl$_2$)

$^1$H NMR (600 MHz, CDCl$_3$) δ 5.67 (s, 1H), 5.47 (d, J=8.4 Hz, 1H), 4.06 (dd, J=8.4, 3.0 Hz, 1H), 2.64 (ABq, J=14.4 Hz, 2H), 2.42-2.37 (m, 1H), 1.95 (dt, J=14.9, 9.7 Hz, 1H), 1.82 (dd, J=13.5, 9.7 Hz, 1H), 1.57 (dd, J=14.9, 8.7 Hz, 1H), 1.42 (t, J=8.0 Hz, 1H), 136-1.29 (m, 6H), 1.25-0.96 (m, 5H), 0.90 (s, 9H), 0.83 (s, 3H), 0.60 (t, J=8.4 Hz, 1H), 0.05 (s, 9H), −0.01 (s, 6H).

$^{13}$C NMR (151 MHz, CDCl$_3$) δ 149.7, 139.3, 137.0, 125.3, 79.8, 73.9, 72.8, 52.2, 49.1, 44.0, 35.4, 28.5, 26.7, 25.9, 22.7, 18.7, 18.0, 17.5, 16.5, 15.4, 12.6, 2.3, −4.3, −5.1.

Intermediate 38

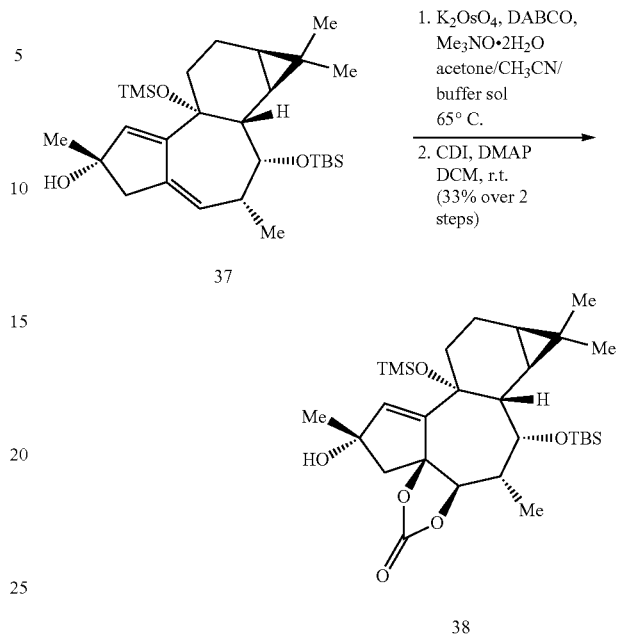

A 100 mL round flask was charged with 37 (246 mg, 0.5 mmol, 1.0 equiv), Me$_3$NO.2H$_2$O (556 mg, 5.0 mmol, 10 equiv) and DABCO (305 mg, 5 mmol, 2.5 equiv) in Acetone/CH$_3$CN/*0.5 M buffer solution (10.0 mL, 0.05 M, 4:3:3). Then, K$_2$OsO$_4$.H$_2$O (18.4 mg, 0.05 mmol, 0.1 equiv) was added and the flask was sealed with a plastic cap and stir vigorously at 65° C. After 12 h, another portion of K$_2$OsO$_4$.H$_2$O (18.4 mg, 0.05 mmol, 0.1 equiv) was added and stir for 8 h before being quenched by the addition of saturated aqueous Na$_2$SO$_3$ (10 mL). The reaction mixture was extracted with ether (3×20 mL). The combined organic layers were washed with brine and dried over Na$_2$SO$_4$, filtered and concentrated in vacuo to afford crude diol.

[*0.5 M buffer solution: pH=3, Na$_2$HPO$_4$ (280 mg) and citric acid (840 mg) was dissolved in H$_2$O (10 mL).]

The crude diol was dissolved in DCM (10.0 mL, 0.05 M) and N,N-carbonyldiimidazole (305 mg, 2.5 mmol, 5.0 equiv) and DMAP (6.1 mg, 0.05 mol, 0.1 equiv) were added. was added. The solution was stirred at room temperature for 7 hours and quenched with water (20 mL). The aqueous layer was separated and extracted further with hexane (2×30 mL). The combined organic layers were dried over Na$_2$SO$_4$, filtered and concentrated in vacuo to remove solvent. Purification of the crude product by loading to flash column chromatography (silica gel, hexanes/EtOAc=20:1→15:1→9:1) afforded desired product 38 (91 mg, 33% over 2 steps) as a colorless oil.

Physical state: colorless oil

R$_f$=0.32 (Hex/EtOAc=7:3; anisaldehyde)

HRMS (m/z): calc. for C$_{29}$H$_{50}$O$_6$Si$_2$ [M+Na]$^+$=573.3038. found, 573.3041.

[α]$_D$=+2.5° (c=0.52, CH$_2$Cl$_2$)

$^1$H NMR (600 MHz, CDCl$_3$) δ 5.97 (s, 1H), 4.76 (d, J=5.1 Hz, 1H), 4.23 (dd, J=7.6, 4.8 Hz, 1H), 2.81-2.75 (m, 1H), 2.56 (d, J=14.5 Hz, 1H), 2.33 (d, J=14.5 Hz, 1H), 1.94-1.87 (m, 1H), 1.67-1.47 (m, 2H), 1.45 (s, 3H), 1.32 (ddd, J=15.2, 10.8, 8.0 Hz, 1H), 1.24-1.20 (m, 1H), 1.15 (d, J=7.7 Hz, 3H), 1.11-1.05 (m, 1H), 1.03 (s, 3H), 0.94 (s, 9H), 0.91 (s, 3H), 0.63 (t, J=9.0 Hz, 1H), 0.21 (s, 9H), 0.07 (s, 3H), 0.06 (s, 3H).

$^{13}$C NMR (151 MHz, CDCl$_3$) δ 153.7, 151.6, 140.7, 93.7, 87.2, 78.3, 75.3, 72.0, 57.1, 41.2, 41.1, 38.2, 28.9, 28.7, 26.0, 19.6, 19.1, 18.3, 17.4, 15.8, 15.1, 11.7, 2.9, −4.1, −5.1.

Intermediate 39 and 39′

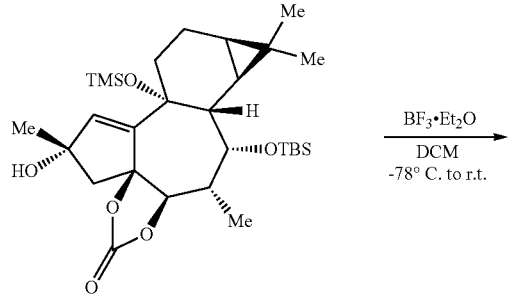

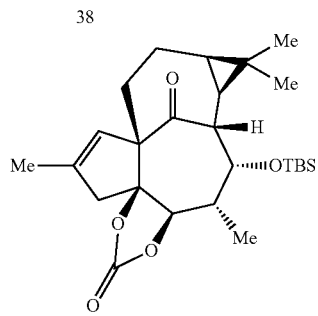

39 (14%)

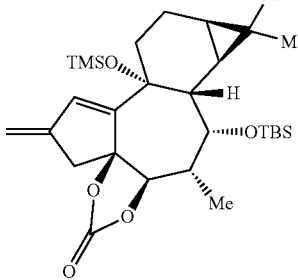

39′ (27%)

To a solution of 38 (50 mg, 0.091 mmol, 1.0 equiv) in DCM (3.7 mL, 0.025 M) was added BF$_3$·Et$_2$O (112 μL, 3.38 mmol, 10 equiv) dropwise at −78° C. The reaction mixture was stirred at this temperature for 2 min before being warmed to room temperature. After 5 min, the reaction was transferred back to −78° C. and a 1:1 mixture of Et$_3$N/MeOH (0.5 mL) was added. The reaction mixture was warmed to room temperature and concentrated under reduced pressure. Purification of the crude product by flash column chromatography (silica gel, hexanes/EtOAc=30:1→45:1) afforded 39 (6.0 mg, 14%) and 39′ (12.9 mg, 27%).

Spectroscopic data for 39:
Physical state: colorless oil
R$_f$=0.53 (Hex/EtOAc=4:1; anisaldehyde)
HRMS (m/z): calc. for C$_{26}$H$_{40}$O$_5$Si [M+H]$^+$=461.2718. found, 461.2722.
[α]$_D$=+39.6° (c=0.5; CH$_2$Cl$_2$)
$^1$H NMR (600 MHz, CDCl$_3$) δ 5.44 (d, J=1.7 Hz, 1H), 4.88 (d, J=5.2 Hz, 1H), 4.20 (dd, J=7.6, 3.8 Hz, 1H), 3.16 (d, J=18.4 Hz, 1H), 2.88-2.82 (m, 1H), 2.62 (d, J=18.2 Hz, 1H), 2.32 (dd, J=11.4, 3.8 Hz, 1H), 2.20-1.99 (m, 2H), 1.71 (s, 3H), 1.56-1.43 (m, 2H), 1.10 (s, 3H), 1.04 (s, 3H), 1.00-0.92 (m, 10H) 0.85 (d, J=8.0 Hz, 3H), 0.71-0.62 (m, 1H), 0.11 (s, 3H), 0.05 (s, 3H).
$^{13}$C NMR (151 MHz, CDCl$_3$) δ 208.0, 153.2, 134.1, 127.2, 93.3, 91.4, 75.3, 67.4, 54.9, 49.2, 38.2, 36.6, 28.3, 25.7, 25.1, 24.9, 23.6, 23.3, 18.2, 16.2, 15.1, 9.5, −4.9, −4.9.

Spectroscopic data for 39′:
Physical state: colorless foam
R$_f$=0.65 (Hex/EtOAc=4:1; anisaldehyde)
HRMS (m/z): calc. for C$_{29}$H$_{48}$O$_5$Si$_2$ [M+H]$^+$=533.3118. found, 533.3121.
[α]$_D$=+18.0° (c=1, CH$_2$Cl$_2$)
$^1$H NMR (600 MHz, CDCl$_3$) δ 6.42 (s, 1H), 5.03 (s, 1H), 4.90 (s, 1H), 4.70 (d, J=5.2 Hz, 1H), 4.24 (dd, J=7.8, 4.8 Hz, 1H), 3.20 (dt, J=17.0, 2.2 Hz, 1H), 2.81 (dt, J=17.0, 1.7 Hz, 1H), 2.78-2.72 (m, 1H), 1.94-1.87 (m, 1H), 1.67-1.48 (m, 2H), 1.40-1.35 (m, 1H), 1.25-1.23 (m, 1H), 1.09 (dd, J=9.7, 6.1 Hz, 1H), 1.04 (s, 3H), 0.98 (d, J=7.6 Hz, 3H), 0.93-0.92 (m, 12H), 0.65-0.62 (m, 1H), 0.21 (s, 9H), 0.07 (s, 3H), 0.05 (s, 3H).
$^{13}$C NMR (151 MHz, CDCl$_3$) δ 155.9, 153.5, 144.9, 136.9, 106.9, 93.0, 87.7, 76.1, 72.0, 48.2, 41.1, 40.2, 37.6, 28.8, 26.0, 19.5, 19.1, 18.2, 17.4, 15.7, 15.2, 11.0, 2.8, −4.2, −5.1.

Intermediate 38 and 38′

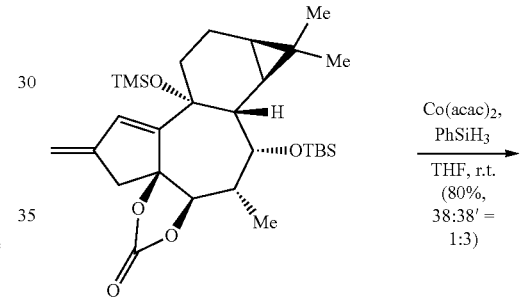

38

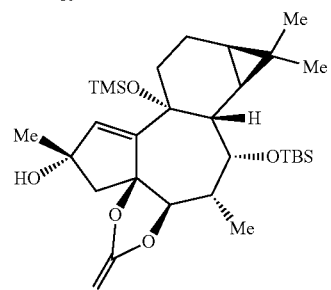

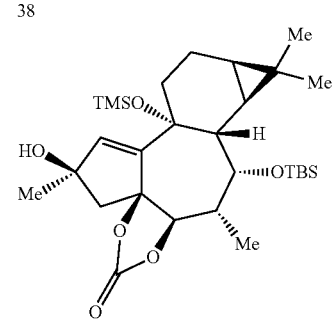

38′

To a solution of 39' (87.5 mg, 0.16 mmol, 1 equiv) in THF (3.3 mL, 0.05 M) was added Co(acac)$_2$ (8.5 mg, 0.033 mmol, 0.2 equiv) and molecular sieves (4 Å, 0.44 g, 5 wt equiv). PhSiH$_3$ (81 μL, 0.66 mmol, 4 equiv) was added slowly while bubbling O$_2$ through the stirred solution. Then the stirring was continued under an O$_2$ atmosphere (no bubbling) at ambient temperature for 10 min. The suspension was then filtered over celite, to remove the molecular sieves and to the resulting solution was concentrated under reduced pressure. Purification of the crude product by flash column chromatography (silica gel, hexanes/EtOAc=20:1→45:1→9:1-4:1) afforded mixture of 38 and 38' as a colorless oil (72.3 mg, 80% (38:38'=1:3, the ratio was determined by crude $^1$H NMR spectrum).

Spectroscopic data for 38':

Physical state: colorless oil

R$_f$=0.27 (Hex/EtOAc=7:3; anisaldehyde)

HRMS (m/z): calc. for C$_{29}$H$_{50}$O$_6$Si$_2$ [M+Na]$^+$=573.3038. found, 573.3041.

[α]$_D$=+1.5° (c=0.39, CH$_2$Cl$_2$)

$^1$H NMR (600 MHz, CDCl$_3$) δ 6.07 (s, 1H), 4.67 (d, J=5.3 Hz, 1H), 4.22 (dd, J=7.6, 4.8 Hz, 1H), 2.78-2.72 (m, 1H), 2.63 (d, J=15.1 Hz, 1H), 2.34 (d, J=15.1 Hz, 1H), 1.97-1.85 (m, 1H), 1.73-1.52 (m, 2H), 1.43 (s, 3H), 1.36 (ddd, J=15.1, 11.0, 8.0 Hz, 1H), 1.22 (t, J=5.4 Hz, 1H), 1.11-1.01 (m, 7H), 0.93 (s, 9H), 0.91 (s, 3H), 0.63 (t, J=7.8 Hz, 1H), 0.20 (s, 9H), 0.07 (s, 3H), 0.06 (s, 3H).

$^{13}$C NMR (151 MHz, CDCl$_3$) δ 153.4, 151.9, 141.6, 93.2, 86.6, 77.3, 75.2, 72.1, 57.8, 41.5, 41.1, 38.1, 28.9, 27.0, 26.0, 19.6, 19.0, 18.3, 17.4, 15.9, 15.1, 11.1, 2.9, −4.1, −5.1.

Intermediate 39 and 39'

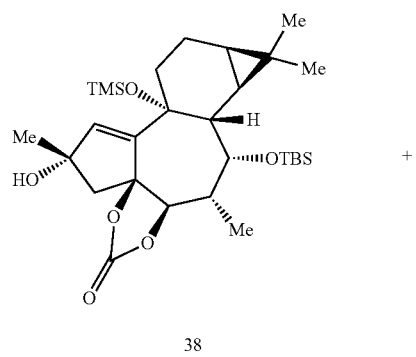

38

39 (16%)

39' (51%)

Synthesis of 39 (synthesis via recovered 38 and 38'): To a solution of mixture of 38 and 38'(54 mg, 0.098 mmol, 1.0 equiv) in DCM (3.9 mL, 0.025 M) was added BF$_3$·Et$_2$O (120 μL, 0.98 mmol, 10 equiv) dropwise at −78° C. The reaction mixture was stirred at this temperature for 2 min before being warmed to −40° C. After 5 min, the reaction was transferred back to −78° C. and a 1:1 mixture of Et$_3$N/MeOH (0.5 mL) was added. The reaction mixture was warmed to room temperature and concentrated under reduced pressure. Purification of the crude product by flash column chromatography (silica gel, hexanes/EtOAc=30:1→45:1) afforded 39 (12.1 mg, 16%) and 39' (26.8 mg, 51%).

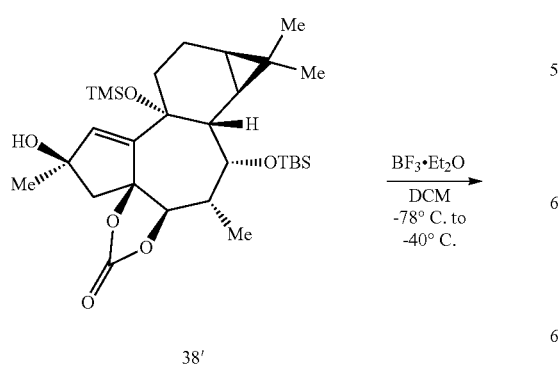

38'

Intermediate 40

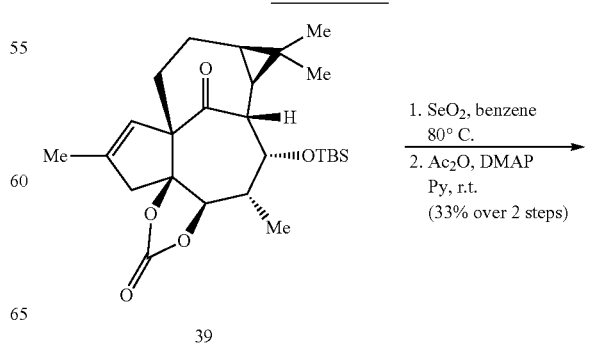

39

-continued

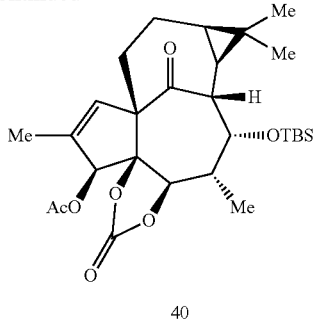

40

Synthesis of SI-3: To a solution of 39 (45.4 mg, 0.099 mmol, 1.0 equiv) in benzene (5 mL, 0.02 M) was added SeO$_2$ (55 mg, 0.49 mmol, 5.0 equiv). The flask was sealed with a plastic cap and the suspension was heated to 80° C. for 21 h. The suspension was cooled to room temperature and was filtered through celite, washed with EtOAc, and then concentrated under reduced pressure. Purification of the crude product by flash column chromatography (silica gel, hexanes/EtOAc=9:1→4:1) afforded alcohol SI-3 (22.0 mg, 47%) as a colorless oil.

Synthesis of 40: To a solution of SI-3 (20.7 mg, 0.043 mmol, 1.0 equiv) in pyridine (1.4 mL, 0.03 M) was added Ac$_2$O (20 μL, 0.22 mmol, 5.0 equiv) and DMAP (20.7 mg, 4.3 μmol, 1.0 equiv). After 10 min stirring, the mixture was quenched with saturated aqueous NaHCO$_3$ (2.0 mL), extracted with EtOAc (3×2 mL) and the combined organic layers were washed with brine (2 mL), dried over Na$_2$SO$_4$, filtered and concentrated under reduced pressure. Purification of the crude product by flash column chromatography (silica gel, hexanes/EtOAc=15:1→9:1) afforded 40 (15.6 mg, 70%) as a colorless oil.

Spectroscopic data for SI-3:
Physical state: colorless oil
R$_f$=0.43 (Hex/EtOAc=7:3; anisaldehyde)
HRMS (m/z): calc. for C$_{26}$H$_{40}$O$_6$Si [M+H]$^+$=477.2667. found, 477.2665.
[α]$_D$=+92.2° (c=0.37, CH$_2$Cl$_2$)
$^1$H NMR (600 MHz, CDCl$_3$) δ 5.63-5.58 (m, 1H), 4.99 (d, J=5.1 Hz, 1H), 4.26-4.18 (m, 2H), 2.94-2.88 (m, 1H), 2.47 (dd, J=11.4, 3.8 Hz, 1H), 2.15-2.06 (m, 2H), 1.79 (s, 3H), 1.62-1.47 (m, 2H), 1.12 (s, 3H), 1.05 (s, 3H), 0.97-0.92 (s, 10H), 0.85 (d, J=8.0 Hz, 3H), 0.74-0.66 (m, 1H), 0.12 (s, 3H), 0.06 (s, 3H).
$^{13}$C NMR (151 MHz, CDCl$_3$) δ 207.1, 152.8, 137.9, 129.3, 90.8, 89.1, 86.3, 73.1, 67.3, 49.9, 38.2, 37.8, 28.2, 25.7, 25.0, 24.7, 23.2, 23.1, 18.2, 15.1, 13.8, 10.2, −4.9.

Spectroscopic data for 40
Physical state: colorless oil
R$_f$=0.54 (Hex/EtOAc=4:1; anisaldehyde)
HRMS (m/z): calc. for C$_{28}$H$_{42}$O$_7$Si [M+H]$^+$=519.2772. found, 519.2763.
[α]$_D$=+42.9° (c=0.17, CH$_2$Cl$_2$)
$^1$H NMR (600 MHz, CDCl$_3$) δ 5.91 (s, 1H), 5.35 (d, J=4.9 Hz, 1H), 5.16 (s, 1H), 4.21 (dd, J=7.5, 3.9 Hz, 1H), 2.90-2.84 (m, 1H), 2.22 (dd, J=11.4, 4.0 Hz, 1H), 2.18 (s, 3H), 2.10-1.99 (m, 2H), 1.75 (s, 3H), 1.57-1.52 (m, 2H), 1.08 (s, 3H), 1.04 (s, 3H), 0.97 (dd, J=11.3, 8.6 Hz, 1H), 0.94 (s, 9H), 0.81 (d, J=8.0 Hz, 3H), 0.71-0.62 (m, 1H), 0.11 (s, 3H), 0.06 (s, 3H).

$^{13}$C NMR (151 MHz, CDCl$_3$) δ 206.9, 172.3, 152.7, 133.4, 133.0, 90.8, 89.0, 88.9, 73.0, 67.1, 50.0, 38.7, 37.7, 28.2, 25.7, 25.2, 25.0, 23.4, 23.2, 20.5, 18.2, 15.1, 14.2, 9.6, −4.9.

Intermediate 41

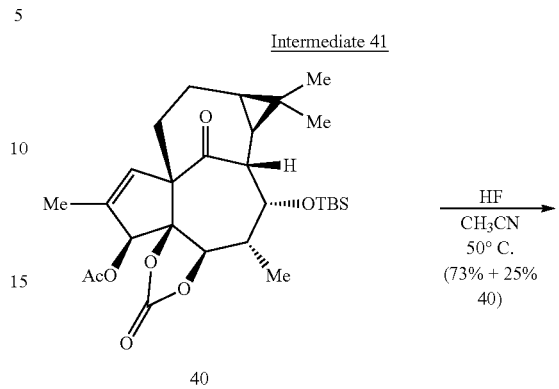

40

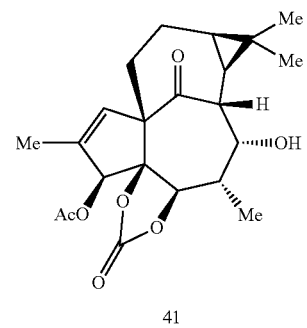

41

A plastic falcon tube was charged with 40 (16.6 mg, 0.032 mmol, 1.0 equiv) and CH$_3$CN (0.64 mL, 0.05 M). 47% aqueous HF (70 μL, 1.92 mmol, 60 equiv) was added and the mixture was heated to 50° C. After 16 h, the reaction was cooled to room temperature and quenched by the slow addition of saturated aqueous NaHCO$_3$ (4 mL). EtOAc (5 mL) was added, the layers were separated, and the aqueous layer was extracted with EtOAc (3×5 mL). The combined organic fractions were dried over Na$_2$SO$_4$, filtered, and concentrated in vacuo. Purification of the crude product by flash column chromatography (silica gel, hex/EtOAc=9:1→4:1→7:3) afforded recovered 40 (4.1 mg, 25%) and 41 (9.4 mg, 73%) as a colorless oil.

Physical state: colorless oil
R$_f$=0.32 (Hex/EtOAc=3:2; anisaldehyde)
HRMS (m/z): calc. for C$_{22}$H$_{28}$O$_7$ [M+H]$^+$=405.1913. found, 405.1920.
[α]$_D$=+18.8° (c=0.51, CH$_2$Cl$_2$)
$^1$H NMR (600 MHz, CDCl$_3$) δ 5.82 (s, 1H), 5.39 (d, J=4.7 Hz, 1H), 5.15 (s, 1H), 4.18 (d, J=8.2 Hz, 1H), 3.12-3.03 (m, 1H), 2.40 (dd, J=11.3, 3.8 Hz, 1H), 2.18 (s, 3H), 2.16-2.01 (m, 2H), 1.77 (s, 3H), 1.65-1.51 (m, 2H), 1.09 (s, 3H), 1.06 (s, 3H), 0.95 (dd, J=11.4, 8.5 Hz, 1H), 0.83 (d, J=8.1 Hz, 3H), 0.74-0.70 (s, 1H).
$^{13}$C NMR (151 MHz, CDCl$_3$) δ 210.7, 172.2, 152.4, 134.0, 132.3, 91.0, 89.0, 88.4, 72.3, 67.4, 48.7, 37.7, 37.0, 28.4, 25.3, 25.1, 23.0, 22.3, 20.4, 14.9, 14.2, 9.7.

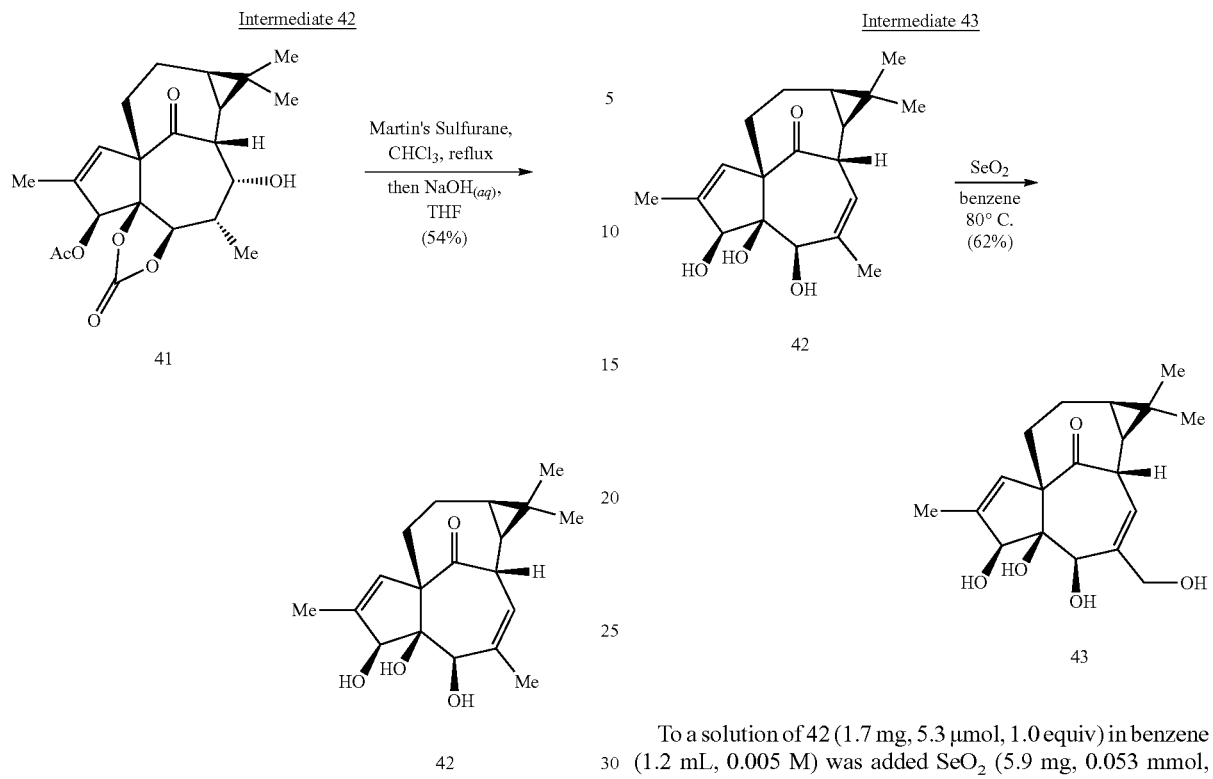

To a solution of 41 (19.1 mg, 0.047 mmol, 1.0 equiv) in CHCl$_3$ (200 μL), was added Martin's sulfurane (100 mg, 0.15 mmol, 3.2 equiv). The solution was heated to reflux for 1 h. Additional Martin's sulfurane (150 mg, 0.23 mmol, 4.8 equiv) was added portion-wise over 2 h until all starting material was consumed. The CHCl$_3$ was removed under reduced pressure and THF (500 μL) and 10% aqueous NaOH (500 μL) were added. The mixture was stirred for 1 hour. EtOAc was added and the layers were separated. The aqueous layer was extracted with EtOAc (5×2 mL). The combined organic fractions were dried over Na$_2$SO$_4$, filtered, and concentrated to give crude product. The crude material was purified by column chromatography (Hex/EtOAc=10:1→6: 1→2:1→4:1) to give 42 (7.1 mg, 54%) as white solid.

Physical state: white solid (m.p.=192-195° C., decomp.)

R$_f$=0.38 (Hex/EtOAc=1:1; anisaldehyde)

HRMS (m/z): calc. for C$_{19}$H$_{26}$O$_4$ [M+H]$^+$=319.1904. found, 319.1904.

[α]$_D$=−10.0° (c=0.2, CH$_2$Cl$_2$)

$^1$H NMR (600 MHz, CDCl$_3$) δ 5.83 (d, J=1.7 Hz, 1H), 5.77 (dt, J=4.9, 1.6 Hz, 1H), 4.44 (d, J=4.4 Hz, 1H), 4.09 (s, 1H), 4.04-4.00 (m, 1H), 3.47 (d, J=10.2 Hz, 1H), 2.53 (d, J=11.4 Hz, 1H), 2.18-1.87 (m, 4H), 1.83 (d, J=1.5 Hz, 3H), 1.78 (s, 3H), 1.63 (ddd, J=14.2, 12.7, 3.8 Hz, 1H), 1.11 (s, 3H), 1.05 (s, 3H), 0.93 (dd, J=12.0, 8.3 Hz, 1H), 0.69-0.62 (m, 1H).

$^{13}$C NMR (151 MHz, CDCl$_3$) δ 208.4, 138.3, 131.5, 123.2, 83.8, 81.6, 76.2, 69.3, 44.2, 37.0, 28.4, 25.5, 24.5, 23.5, 23.2, 22.1, 15.4, 15.1 (one signal does not appear due to incidental overlap).

To a solution of 42 (1.7 mg, 5.3 μmol, 1.0 equiv) in benzene (1.2 mL, 0.005 M) was added SeO$_2$ (5.9 mg, 0.053 mmol, 10.0 equiv) and heated to 80° C. for 9 h. The suspension was cooled to room temperature and was filtered through celite, washed with EtOAc, and then concentrated under reduced pressure. Purification by PTLC (DCM/MeOH=9:1) yielded 43 (1.1 mg, 62%) as a colorless oil.

Physical state: colorless oil

R$_f$=0.38 (DCM/MeOH=9:1; anisaldehyde)

HRMS (m/z): calc. for C$_{19}$H$_{26}$O$_5$ [M+Na]$^+$=357.1678. found, 357.1670.

[α]$_D$=−12.7° (c=0.11, CH$_2$Cl$_2$)

$^1$H NMR (600 MHz, CDCl$_3$) δ 6.07 (d, J=4.8 Hz, 1H), 5.81 (d, J=1.6 Hz, 1H), 4.43 (s, 1H), 4.22-4.08 (m, 3H), 3.85 (s, 1H), 2.10-1.89 (m, 4H), 1.83 (d, J=1.5 Hz, 3H), 1.66-1.61 (m, 1H), 1.11 (s, 3H), 1.06 (s, 3H), 0.95 (dd, J=12.0, 8.3 Hz, 1H), 0.71-0.67 (m, 1H).

$^{13}$C NMR (151 MHz, CDCl$_3$) δ 208.0, 140.4, 138.7, 130.9, 127.0, 83.7, 81.0, 75.2, 69.3, 67.1, 44.3, 36.7, 28.4, 25.6, 24.6, 23.2, 23.1, 15.5, 15.1.

Intermediate 44

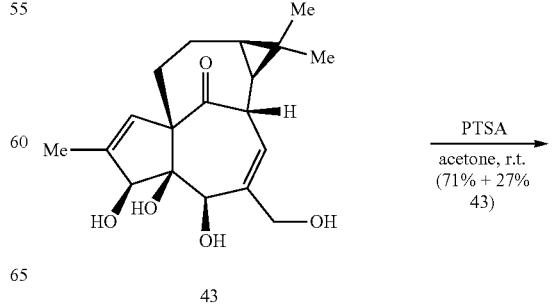

43

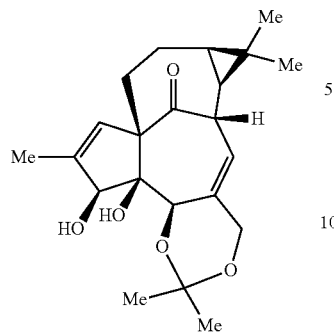

44

43 (1.5 mg, 4.5 μmol) was dissolved in a solution of p-toluenesulfonic acid monohydrate in acetone (0.2 mg/mL, 0.5 mL) and stirred at room temperature for 0.5 h. The reaction was quenched by few drops of saturated aqueous NaHCO$_3$ and concentrated under reduced pressure. The residue was dissolved in EtOAc (1.0 mL), washed with brine and concentrated to give crude product. Purification by PTLC (Hex/EtOAc=7:3) to afforded recovered 44 (0.4 mg, 27%) and 44 (1.2 mg, 71%) as a colorless oil.

Physical state: colorless oil $R_f$=0.71 (Hex/EtOAc=7:3; anisaldehyde)

HRMS (m/z): calc. for C$_{22}$H$_{30}$O$_5$ [M+Na]$^+$=397.1997. found, 397.1997.

[α]$_D$=−19.3° (c=0.15, CH$_2$Cl$_2$)

$^1$H NMR (600 MHz, CDCl$_3$) δ 5.82 (dd, J=3.9, 1.9 Hz, 1H), 5.79 (d, J=1.6 Hz, 1H), 4.26 (s, 1H), 4.22-4.06 (m, 3H), 3.95 (s, 1H), 2.19-2.13 (m, 1H), 2.05-1.90 (m, 2H), 1.83 (d, J=1.5 Hz, 3H), 1.66-1.57 (m, 1H), 1.42 (s, 3H), 1.35 (s, 3H), 1.11 (s, 3H), 1.05 (s, 3H), 0.92 (dd, J=12.0, 8.3 Hz, 1H), 0.70-0.66 (m, 1H).

$^{13}$C NMR (151 MHz, CDCl$_3$) δ 208.5, 139.4, 136.1, 130.4, 122.0, 100.5, 82.8, 80.4, 73.6, 69.5, 64.1, 44.3, 35.7, 28.4, 26.6, 25.8, 24.5, 23.3, 23.2, 21.0, 15.5, 15.4.

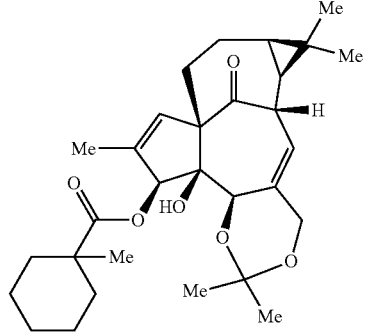

45

To a solution of 44 (1.5 mg, 4 μmol, 1.0 equiv) and 1-methylcyclohexane-1-carboxylic anhydride (3.2 mg, 12 μmol, 3.0 equiv) in THF (0.4 mL) was added a solution of LHMDS in THF (1.0 M, 22 μL, 22 μmol, 5.0 equiv) at room temperature. The solution was stirred at room temperature for 10 min, diluted with Et$_2$O (1 mL), and washed with H$_2$O. The aqueous phase was extracted with Et$_2$O (3×1 mL). The combined organic phases were concentrated under reduced pressure. Purification by PTLC (Hex/EtOAc=4:1) to afforded 45 (1.1 mg, 51%) as a white oil.

Physical state: white oil $R_f$=0.63 (Hex/EtOAc=7:3; anisaldehyde)

HRMS (m/z): calc. for C$_{30}$H$_{42}$O$_6$ [M+H]$^+$=521.2879. found, 521.2875.

[α]$_D$=+2.4° (c=0.21, CH$_2$Cl$_2$)

$^1$H NMR (600 MHz, CDCl$_3$) δ 5.91 (d, J=1.6 Hz, 1H), 5.81-5.77 (m, 1H), 5.56 (s, 1H), 4.26-4.10 (m, 3H), 4.03 (s, 1H), 2.25 (dt, J=14.3, 3.7 Hz, 1H), 2.11-1.86 (m, 3H), 1.73 (d, J=1.6 Hz, 3H), 1.62-1.53 (m, 5H), 1.47 (s, 3H), 1.41 (s, 3H), 1.36-1.21 (m, 5H), 1.19 (s, 3H), 1.08 (s, 3H), 1.04 (s, 3H), 0.94-0.85 (m, 1H), 0.69-0.65 (m, 1H).

$^{13}$C NMR (151 MHz, CDCl$_3$) δ 208.7, 178.2, 136.4, 136.1, 132.9, 121.7, 100.3, 83.8, 81.8, 73.7, 68.9, 64.3, 44.0, 43.6, 35.7, 35.6, 35.4, 34.9, 28.4, 26.7, 26.0, 25.8, 25.6, 24.8, 23.3, 23.2, 23.1, 20.8, 15.6, 15.4.

Example 8

11-desmethyl-ingenol 3-(1-methyl-cyclohexanecarboxylate) (Compound 8)

Intermediate 45

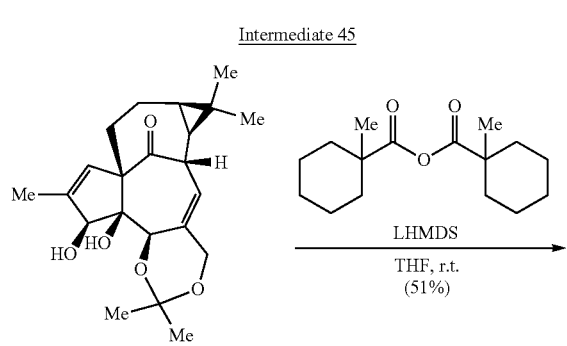

44

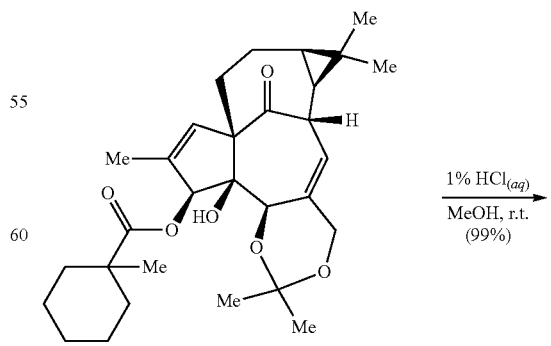

45

-continued

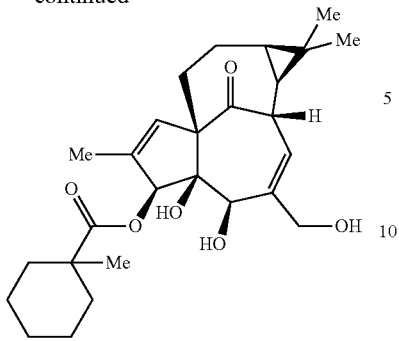

8

Synthesis of 8: A solution of 45 (0.4 mg, 0.8 µmol) in methanol (0.2 mL), which contained 1% of concentrated aqueous hydrochloric acid solution, was stirred at room temperature for 1 h. The solution was concentrated under reduced pressure. Purification by PTLC (Hex/EtOAc=5:5) to afforded 8 (0.4 mg, 99%) as a colorless oil.

Physical state: colorless oil $R_f$=0.33 (Hex/EtOAc=1:1; anisaldehyde)

HRMS (m/z): calc. for $C_{27}H_{38}O_6$ [M+Na]$^+$=481.2566. found, 481.2559.

$[\alpha]_D$=+5.4°(c=0.13, $CH_2Cl_2$)

$^1$H NMR (600 MHz, $CDCl_3$) δ 6.07 (d, J=4.0 Hz, 1H), 5.90 (d, J=1.6 Hz, 1H), 5.43 (s, 1H), 4.18-4.12 (m, 3H), 4.08 (s, 1H), 2.15 (dt, J=14.2, 3.8 Hz, 1H), 2.09-1.88 (m, 3H), 1.75 (d, J=1.5 Hz, 3H), 1.67-1.24 (m, 10H), 1.21 (s, 3H), 1.08 (s, 3H), 1.05 (s, 3H), 0.93 (dd, J=12.0, 8.3 Hz, 1H), 0.70-0.66 (m, 1H).

$^{13}$C NMR (151 MHz, $CDCl_3$) δ 207.6, 179.0, 139.1, 135.4, 132.8, 128.2, 84.5, 82.9, 77.0 (verify by HSQC), 68.7, 67.5, 43.8, 43.7, 36.0, 35.6, 35.6, 28.3, 25.8, 25.7, 24.8, 23.3, 23.3, 23.2, 23.1, 15.6, 15.2 (one signal does not appear due to incidental overlap).

Example 1

Neutrophil Oxidative Burst

PMN's (polymorphonuclear leukocytes) were isolated and purified from fresh buffy coats by sequential sedimentation, density centrifugation and lysis of contaminating erythrocytes. Buffy coats were incubated with 2% methocel for 30-45 min to differentially sediment red blood cells. The leukocyte-rich supernatant was transferred to lymphoprep tubes to remove mononuclear cells by density centrifugation (400×g, 30 min). The pellet was resuspended and any remaining erythrocytes lysed using 0.2% NaCl for 30 sec before restoring isotonicity by the addition of 1.2% NaCl. This step was repeated until the cell pellet appears relatively free of red blood cells. Cells were resuspended in DPBS (Dulbecco's Phosphate Buffered Saline) (w.o. $Ca^{2+}$, $Mg^{2+}$) and the concentration adjusted to 1.4×10$^6$ cells/ml in HBSS (Hanks Balanced Salt solution) (w $Ca^{2+}$, $Mg^{2+}$) containing 0.1% BSA (Bovine Serum Albumin) and 5 mM glucose just prior to assay initiation. Titrated reference and test compounds were pre-mixed with HE (Hydroethidine) (10 µM final assay concentration) before addition to 96-well plates containing 2.5× 10$^5$ cells. Following 40 min incubation at RT, changes in the respiratory burst was estimated by measuring fluorescence at 579 nm (excitation: 485 nm) using an Envision plate reader.

Test compound titration curves were fitted to a four-parameter sigmoidal curve after normalizing the effect of the test compound to the effect of the positive control (5×10$^{-7}$ M PEP0005). Rel $EC_{50}$ (relative $EC_{50}$) denotes the concentration of test compound producing an effect that is midway between the fitted top and bottom.

Example 2

HeKa Cytokine Release (IL-8)

Primary human epidermal keratinocytes, HeKa, were seeded (10.000 cells/well) in 96-well plates the day before the assay. Test compounds were diluted in DMSO (dimethyl sulfoxide) and further diluted in assay medium and pipetted into wells of 96 well-plates containing HeKa cells. The plates were incubated for 6 h at 37° C. in humidified air with 5% $CO_2$. Plates were centrifuged briefly to spin down cells at 4° C., the supernatant was removed and analysed by Meso Scale Discovery (MSD) 4-spot cytokine assay (Pro-inflammatory II Ultra Sensitive kit, MSD, MD, USA). The MSD assay employs a sandwich immunoassay format where capture antibodies are coated in a patterned array on the bottom of the wells of a 4-Spot-Multi-MSD plate. Standard samples were incubated in the MULTI-SPOT plates as well, and the cytokine (IL-8) binds to its corresponding capture antibody spot. The cytokine level was quantitated on a SECTOR™ Imager using a cytokine-specific Detection Antibody labelled with MSD SULFO-TAG™ reagent.

Test compound titration curves were fitted to a four-parameter sigmoidal curve after normalizing the effect of the test compound to the effect of the positive control (1.5×10$^{-7}$ M PEP0005). Rel $EC_{50}$ (relative $EC_{50}$) denotes the concentration of test compound producing an effect that is midway between the fitted top and bottom.

Example 3

Necrosis Assay

HeLa cells (ATCC CCL-002) were grown in minimal essential medium (Invitrogen catalog no. 42360) containing 10% fetal bovine serum, 100 IU/ml penicillin and 100 µg/ml streptomycin. 4,000-6,000 cells were seeded into 96-well black ViewPlates-plates, clear bottom, (Perkin Elmer) in 100 µl medium and incubated overnight. Compounds were dissolved and pre-diluted in DMSO in 96-well polypropylene plates (Greiner) in a concentration range of 15 µM to 600 µM. At the time of the experiment cell plates were placed on heating blocks at 37° C., medium was removed and 40 µl fresh, pre-warmed medium was added per well. Cells were incubated for 15 min before addition of compounds. In parallel, 3 µl of compounds were diluted with 197 µl growth medium on a Tecan freedom-EVO pipetting station using 250 µl/s pipetting speed, in order to ensure effective mixing of the highly concentrated compound solutions with the aqueous phase. These pre-dilution plates were then equilibrated on heating blocks at 37° C. for 10 min. 80 µl pre-diluted compound were transferred manually to the corresponding wells containing HeLa cells yielding compound concentrations of 10 µM to 400 µM. Control conditions were 1% DMSO in growth medium (100% viability) and 400 µM ingenol mebutate in growth medium (0% viability). Plates were incubated on the heating blocks at 37° C. for 30 min. At the end of the incubation 10 µl PrestoBlue reagent (Invitrogen) were added to each well, plates were sealed with black seal, followed by incubation at 37° C. for 10 min with gentle shaking (150 rpm).

Subsequently, plates were placed at room temperature for 20-30 min. Plates were read immediately after on an Envision Fluorescence reader (Perkin Elmer) with excitation at 535 nm and emission at 630 nm. Test compound titration curves were fitted to a four-parameter sigmoidal curve after normalizing the effect of the test compound to the effect of the positive control (4 $10^{-4}$ M PEP0005/ingenol mebutate). AbsEC$_{50}$ (absolute EC$_{50}$) denotes the concentration of test compound producing 50% effect.

Example 4

PKC δ Binding Assay

On the day at experiment Human Protein Kinase C delta (PKCδ, Millipore cat#14-504) was diluted in 20 mM HEPES, 0.03% Triton X-100. Amount of enzyme in each assay was 7.25 ng (final assay volume is 25 µL). All compounds for testing were diluted to 1 mM in 100% DMSO as an intermediary dilution. The compounds were then diluted further to 50 µM, and then serially diluted in 100% DMSO in semi-logarithmic decrements for 12 points. 0.5 µL of each concentration, in duplicate, was pipetted into a dry 96 well assay plate using a TTP Mosquito. Control and blank wells received 0.5 µL of 100% DMSO instead of compound. The assay was built with the addition of 14.5 µL of assay mixture, containing appropriately diluted enzyme and 20 mM HEPES pH 7.4, 0.03% Triton X-100, 0.05 mg/mL phosphatidylserine, and 50 µM ERMRPRKRQGSVRRRV. The assay was started with the addition of 10 µL ATP containing γ-33P-ATP] (specific activity approx. 500 cpm/pmol), to a final assay concentration of 15 µM. The reaction was allowed to proceed at room temperature for 40 minutes before the addition of 5 µL 3% ortho-phosphoric acid. Blank wells were acid blanks, and had 5 µL 3% ortho-phosphoric acid added before the addition of ATP. 10 µL of the stopped reaction products was transferred to a P30 filtermat which was then washed 4 times in 75 mM ortho-phosphoric acid, and once in methanol before drying. The filter was read by liquid scintillation counting using a Wallac Trilux. Rel EC$_{50}$ (relative EC$_{50}$) denotes the concentration of test compound that produces a response half-way between the fitted top and the fitted bottom of the curve when activities are normalized to the effect of DMSO.

Example 9

PKCbetaII Activity Assay

On the day at experiment Human Protein Kinase C betaII (PKCbII, Millipore cat#14-496) was incubated with 20 mM HEPES pH 7.4, 0.03% Triton X-100, 0.1 mM CaCl2, 0.1 mg/mL phosphatidylserine, 0.1 mg/mL histone H1, 10 mM MgAcetate. Amount of enzyme in each assay was 1.8 ng (final assay volume is 25 µL). The compounds were then diluted to 500 µM, and then serially diluted in 100% DMSO in semi-logarithmic decrements for 12 points. 0.5 µL of each concentration, in duplicate, was pipetted into a dry 96 well assay plate using a TIP Mosquito. Control and blank wells received 0.5 µL of 100% DMSO instead of compound. 14.5 µl kinase in assay buffer was added to each well. The assay was started with the addition of 10 µL ATP containing γ-33P-ATP] (specific activity approx. 500 cpm/pmol), to a final assay concentration of 70 µM. The reaction was allowed to proceed at room temperature for 40 minutes before the addition of 5 µL 3% ortho-phosphoric acid. Blank wells were acid blanks, and had 5 µL 3% ortho-phosphoric acid added before the addition of ATP. 10 µL of the stopped reaction products was transferred to a P30 filtermat which was then washed 4 times in 75 mM ortho-phosphoric acid, and once in methanol before drying. The filter was read by liquid scintillation counting using a Wallac Trilux. Rel EC$_{50}$ (relative EC$_{50}$) denotes the concentration of test compound that produces a response half-way between the fitted top and the fitted bottom of the curve when activities are normalized to the effect of DMSO.

Compounds of the present invention were tested in the neutrophil oxidative burst assay according to the description in example 1, in the HeKa cytokine release assay according to the description in example 2, in the PKC δ binding assay according to the description in example 4 and in the PKC βII binding assay according to the description in example 9.

Results are shown in the table below.

| Compound No. | Neutrophil oxidative burst Rel EC$_{50}$ (nM) | HeKa cytokine release (IL-8) Rel EC$_{50}$ (nM) | PKC-δ binding Rel EC$_{50}$ (nM) | PKC-β binding Rel EC$_{50}$ (nM) |
|---|---|---|---|---|
| 5 | 13 | 130 | 1110 | 6 |
| 6 | 7 | 26 | 80 | 0.8 |
| 7 | 9 | 35 | 154 | 0.2 |
| 8 | 4 | 4 | 7 | 0.1 |

The invention claimed is:
1. A compound according to formula I

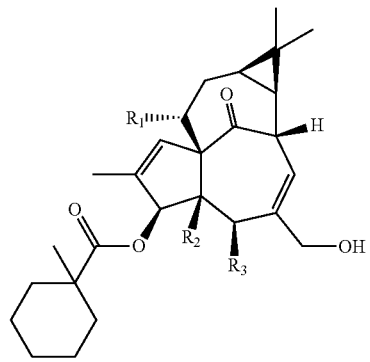

I wherein
R$_1$ represents hydrogen, R$_2$ represents hydroxyl and R$_3$ represents hydroxyl;
or
R$_1$ represents methyl, R$_2$ represents hydroxyl and R$_3$ represents hydrogen;
or
R$_1$ represents methyl, R$_2$ represents hydrogen and R$_3$ represents hydroxyl;
or
R$_1$ represents methyl, R$_2$ represents hydrogen and R$_3$ represents hydrogen;
or hydrates or solvates thereof.

2. The compound according to claim 1, wherein R$_1$ represents hydrogen, R$_2$ represents hydroxyl and R$_3$ represents hydroxyl.

3. The compound according to claim 1, wherein R$_1$ represents methyl, R$_2$ represents hydrogen and R$_3$ represents hydroxyl.

4. The compound according to claim 1, wherein R$_1$ represents methyl, R$_2$ represents hydroxyl and R$_3$ represents hydrogen.

5. The compound according to claim 1, wherein $R_1$ represents methyl, $R_2$ represents hydrogen and $R_3$ represents hydrogen.

6. The compound according to claim 1, wherein the compound is selected from the list consisting of
- 11-desmethyl-ingenol 3-(1-methyl-cyclohexanecarboxylate),
- 4-deoxyingenol 3-(1-methyl-cyclohexanecarboxylate),
- 5-deoxyingenol 3-(1-methyl-cyclohexanecarboxylate) and
- 4,5-dideoxyingenol 3-(1-methyl-cyclohexanecarboxylate).

7. The compound according to claim 1 for use as a medicament.

8. The compound according to claim 1 for use in treatment of physiological disorders or diseases associated with hyperplasia or neoplasia.

9. The compound according to claim 8 wherein the disorder or disease is selected from cutaneous warts, genital warts, actinic keratosis, squamous cell carcinoma (SCC), basal cell carcinoma (BCC), lentigo maligna, cervical intraepithelial neoplasia, anal intraepithelial neoplasia or vulva intraepithelial neoplasia.

10. The pharmaceutical composition comprising a compound according to claim 1 together with a pharmaceutically acceptable vehicle or excipient or pharmaceutically acceptable carrier(s).

11. The pharmaceutical composition according to claim 10 together with one or more other therapeutically active compound(s).

12. A compound selected from the group consisting of:

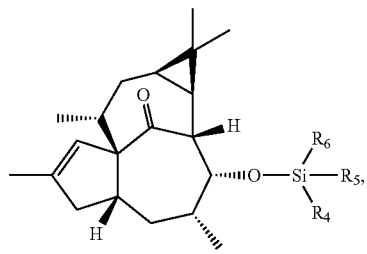
11'

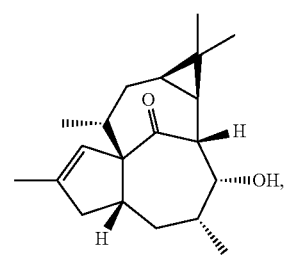
11a

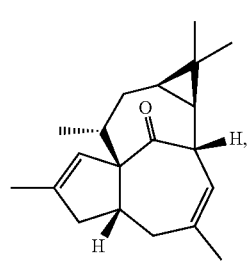
16

-continued

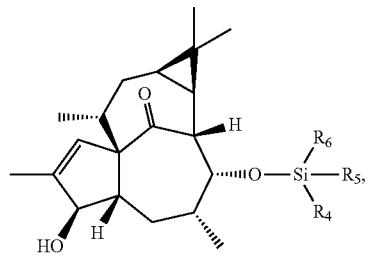
20'

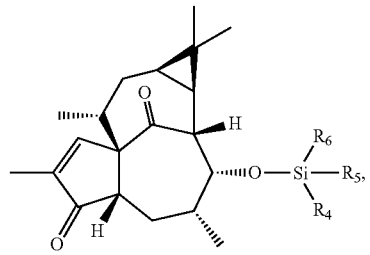
21'

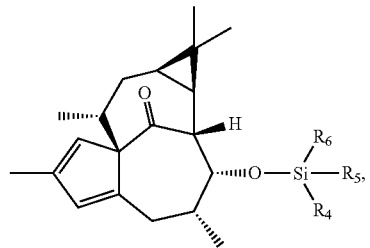
23'

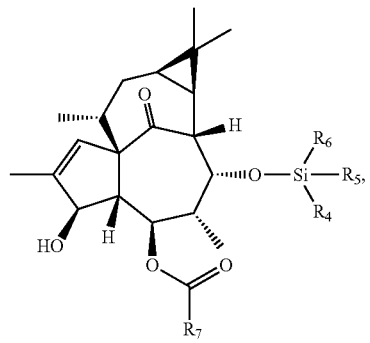
33'

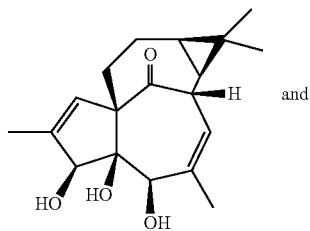
42
and

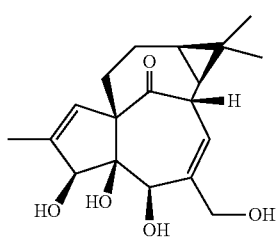
43 wherein $R_4$, $R_5$, $R_6$ and $R_7$ each independently are selected from the group consisting of $(C_1\text{-}C_6)$alkyl.
13. The compound according to claim 12 selected from the group consisting of:
11
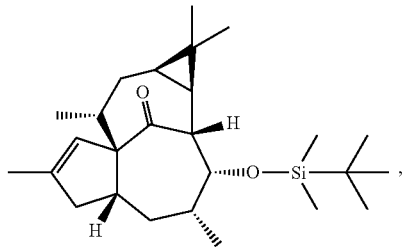
11a
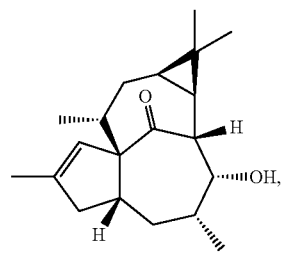
16
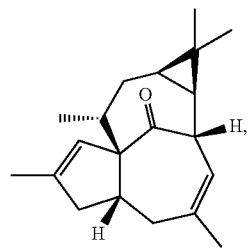
20
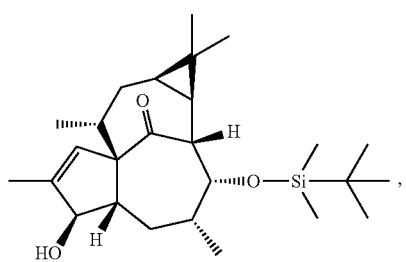
21
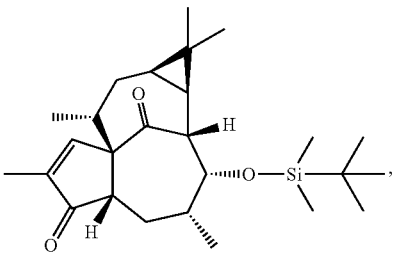
23
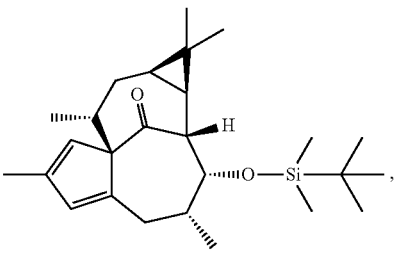
33
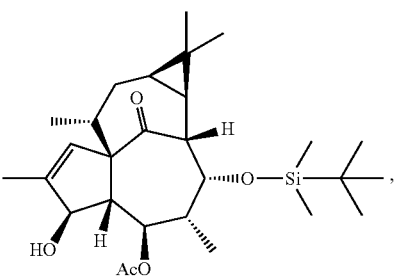
42
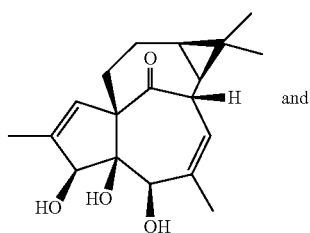
43
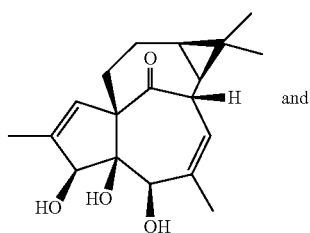
* * * * *